(12) United States Patent
Gamsey et al.

(10) Patent No.: US 11,866,588 B2
(45) Date of Patent: Jan. 9, 2024

(54) POLYMERIZABLE NEAR-IR DYES

(71) Applicant: Profusa, Inc., South San Francisco, CA (US)

(72) Inventors: Soya Gamsey, San Francisco, CA (US); Alex Kutyavin, Lake Stevens, WA (US); Jacob William Clary, Moss Beach, CA (US)

(73) Assignee: Profusa, Inc., Emeryville, CA (US)

( * ) Notice: Subject to any disclaimer, the term of this patent is extended or adjusted under 35 U.S.C. 154(b) by 840 days.

(21) Appl. No.: 16/448,186

(22) Filed: Jun. 21, 2019

(65) Prior Publication Data

US 2020/0140690 A1    May 7, 2020

Related U.S. Application Data

(63) Continuation of application No. PCT/US2017/067847, filed on Dec. 21, 2017.

(60) Provisional application No. 62/437,599, filed on Dec. 21, 2016.

(51) Int. Cl.
| | |
|---|---|
| *C09B 69/10* | (2006.01) |
| *C09B 23/00* | (2006.01) |
| *C09B 23/08* | (2006.01) |
| *C09B 23/10* | (2006.01) |
| *C09K 11/06* | (2006.01) |
| *C09B 23/01* | (2006.01) |

(52) U.S. Cl.
CPC ........ *C09B 69/105* (2013.01); *C09B 23/0066* (2013.01); *C09B 23/083* (2013.01); *C09B 23/107* (2013.01); *C09K 11/06* (2013.01); *C09K 2211/1466* (2013.01)

(58) Field of Classification Search
None
See application file for complete search history.

(56) References Cited

U.S. PATENT DOCUMENTS

| | | | |
|---|---|---|---|
| 4,925,268 A | 5/1990 | Iyer et al. | |
| 5,220,036 A | 6/1993 | King | |
| 5,242,835 A | 9/1993 | Jensen | |
| 5,371,122 A | 12/1994 | Kawahara et al. | |
| 5,487,885 A | 1/1996 | Sovak et al. | |
| 5,496,903 A | 3/1996 | Watanabe et al. | |
| 5,837,865 A | 11/1998 | Vinogradov et al. | |
| 6,011,984 A | 1/2000 | Van et al. | |
| 6,013,122 A | 1/2000 | Klitzman et al. | |
| 6,207,461 B1 | 3/2001 | Baumann et al. | |
| 6,274,086 B1 | 8/2001 | Wilson et al. | |
| 6,362,175 B1 | 3/2002 | Vinogradov et al. | |
| 6,485,703 B1 | 11/2002 | Cote et al. | |
| 6,671,527 B2 | 12/2003 | Petersson et al. | |
| 6,682,938 B1 | 1/2004 | Satcher, Jr. et al. | |
| 6,747,159 B2 | 6/2004 | Caputo et al. | |
| 6,794,195 B2 | 9/2004 | Colvin, Jr. | |
| 6,858,403 B2 | 2/2005 | Han et al. | |
| 7,060,503 B2 | 6/2006 | Colvin, Jr. | |
| 7,078,554 B2 | 7/2006 | Daniloff et al. | |
| 7,358,094 B2 | 4/2008 | Bell et al. | |
| 7,388,110 B2 | 6/2008 | Ochiai et al. | |
| 7,473,551 B2 | 1/2009 | Warthoe | |
| 7,524,985 B2 | 4/2009 | Ochiai et al. | |
| 7,939,332 B2 | 5/2011 | Colvin, Jr. | |
| 8,772,279 B2 | 7/2014 | Mirizzi et al. | |
| 9,375,494 B2 | 6/2016 | Gamsey et al. | |
| 9,410,958 B2 | 8/2016 | Bertozzi et al. | |
| 9,650,566 B2 | 5/2017 | Gamsey et al. | |
| 9,850,566 B2 | 12/2017 | Zimmermann et al. | |
| 9,867,560 B2 | 1/2018 | Gamsey et al. | |
| 10,156,573 B2 | 12/2018 | Tian et al. | |
| 10,383,557 B2 | 8/2019 | Gamsey et al. | |
| 10,494,385 B2 | 12/2019 | Gamsey et al. | |
| 10,662,333 B2 | 5/2020 | Colvin | |
| 10,717,751 B2 | 7/2020 | Gamsey et al. | |
| 10,772,546 B2 | 9/2020 | Balaconis et al. | |
| 10,874,337 B2 | 12/2020 | Gamsey et al. | |
| 11,534,503 B2 | 12/2022 | Balaconis et al. | |
| 2002/0119581 A1 | 8/2002 | Daniloff et al. | |
| 2003/0082663 A1 | 5/2003 | Daniloff et al. | |
| 2004/0224021 A1 | 11/2004 | Omidian et al. | |
| 2007/0036682 A1 | 2/2007 | Gu et al. | |
| 2007/0110672 A1 | 5/2007 | Bellott et al. | |
| 2008/0075752 A1 | 3/2008 | Ratner et al. | |
| 2008/0311304 A1 | 12/2008 | Thompson et al. | |
| 2010/0303772 A1 | 12/2010 | McMillan et al. | |

(Continued)

FOREIGN PATENT DOCUMENTS

| | | |
|---|---|---|
| CA | 2843950 A1 | 2/2013 |
| CN | 1355802 A | 6/2002 |

(Continued)

OTHER PUBLICATIONS

Extended European Search Report for European Application No. 18200504.1, dated Apr. 8, 2019, 13 pages.
Extended European Search Report dated Jul. 3, 2020, for European Application No. 17887567.0, 6 pages.
Extended European Search Report dated Jan. 25, 2021, for European Application No. 17884465.0, 11 pages.
International Search Report and Written Opinion for International Application No. PCT/US2014/026183, dated Jul. 14, 2014, 11 pages.

(Continued)

*Primary Examiner* — Fred M Teskin

(74) *Attorney, Agent, or Firm* — COOLEY LLP

(57) ABSTRACT

The present invention is directed, in certain embodiments, to polymerizable near-IR dyes and polymers comprising said dyes as monomeric residues. In other embodiments, the present invention also relates to methods for the preparation of polymerizable near-IR dyes, and to the use of polymerizable near-IR dyes in the preparation of fluorescent polymers.

20 Claims, 3 Drawing Sheets

(56) References Cited

U.S. PATENT DOCUMENTS

| | | |
|---|---|---|
| 2012/0165435 A1 | 6/2012 | Santhanam et al. |
| 2012/0168697 A1 | 7/2012 | Thompson et al. |
| 2012/0214780 A1 | 8/2012 | Crapo et al. |
| 2012/0265034 A1 | 10/2012 | Wisniewski et al. |
| 2013/0004785 A1 | 1/2013 | Carlson et al. |
| 2013/0041200 A1 | 2/2013 | Sorokin et al. |
| 2014/0088383 A1 | 3/2014 | Colvin et al. |
| 2014/0148596 A1 | 5/2014 | Dichtel et al. |
| 2014/0275869 A1 | 9/2014 | Kintz et al. |
| 2014/0286875 A1 | 9/2014 | Gamsey et al. |
| 2014/0316224 A1 | 10/2014 | Sato |
| 2014/0357964 A1 | 12/2014 | Wisniewski et al. |
| 2014/0364707 A1 | 12/2014 | Kintz et al. |
| 2015/0246141 A1* | 9/2015 | David .............. C08F 122/36 424/9.6 |
| 2015/0353585 A1 | 12/2015 | Nagano et al. |
| 2016/0154001 A1 | 6/2016 | Strongin et al. |
| 2016/0213288 A1 | 7/2016 | Wisniewski et al. |
| 2016/0374556 A1 | 12/2016 | Colvin, Jr. et al. |
| 2016/0374601 A1 | 12/2016 | Gamsey et al. |
| 2016/0376501 A1 | 12/2016 | Gamsey et al. |
| 2017/0087376 A1 | 3/2017 | McMillan et al. |
| 2017/0319137 A1 | 11/2017 | Tsubouchi et al. |
| 2017/0325722 A1 | 11/2017 | Wisniewski et al. |
| 2018/0179233 A1 | 6/2018 | Gamsey et al. |
| 2018/0184956 A1 | 7/2018 | Gamsey et al. |
| 2019/0010170 A1 | 1/2019 | Gamsey et al. |
| 2019/0352510 A1 | 11/2019 | Colvin |
| 2020/0000383 A1 | 1/2020 | Gamsey et al. |
| 2020/0008719 A1 | 1/2020 | Bremer et al. |
| 2020/0023079 A1 | 1/2020 | Balaconis et al. |
| 2020/0107762 A1 | 4/2020 | Gamsey et al. |
| 2021/0093239 A1 | 4/2021 | Gamsey et al. |
| 2021/0101915 A1 | 4/2021 | Gamsey et al. |

FOREIGN PATENT DOCUMENTS

| | | |
|---|---|---|
| CN | 1529815 A | 9/2004 |
| CN | 1638810 A | 7/2005 |
| CN | 1720250 A | 1/2006 |
| CN | 1784601 A | 6/2006 |
| CN | 1900212 A | 1/2007 |
| CN | 101305012 A | 11/2008 |
| CN | 101360987 A | 2/2009 |
| CN | 101522815 A | 9/2009 |
| CN | 101845116 A | 9/2010 |
| CN | 102735667 A | 10/2012 |
| CN | 104788433 A | 7/2015 |
| CN | 105263936 A | 1/2016 |
| CN | 105602276 A | 5/2016 |
| EP | 0352610 A2 | 1/1990 |
| JP | H0853467 A | 2/1996 |
| JP | 2003508186 A | 3/2003 |
| JP | 2004528537 A | 9/2004 |
| JP | 2005500512 A | 1/2005 |
| JP | 2006036664 A | 2/2006 |
| JP | 2006104140 A | 4/2006 |
| WO | WO-8904476 A1 | 5/1989 |
| WO | WO 02/054067 A2 | 7/2002 |
| WO | WO-02057788 A2 | 7/2002 |
| WO | WO 03/078424 A1 | 9/2003 |
| WO | WO-03074091 A2 | 9/2003 |
| WO | WO-2004096817 A1 | 11/2004 |
| WO | WO-2005065241 A2 | 7/2005 |
| WO | WO-2007028037 A1 | 3/2007 |
| WO | WO 2008/014280 A2 | 1/2008 |
| WO | WO 2008/066921 A2 | 6/2008 |
| WO | WO-2010116142 A2 | 10/2010 |
| WO | WO-2011089509 A1 | 7/2011 |
| WO | WO 2012/027593 A1 | 3/2012 |
| WO | WO-2012048150 A1 | 4/2012 |
| WO | WO 2013/130761 A1 | 9/2013 |
| WO | WO 2014/106957 A1 | 7/2014 |
| WO | WO 2014/160258 A1 | 10/2014 |
| WO | WO-2014197786 A2 | 12/2014 |
| WO | WO 2017/218903 A1 | 12/2017 |
| WO | WO-2018119204 A1 | 6/2018 |
| WO | WO 2018/125913 A1 | 7/2018 |
| WO | WO-2019194875 A2 | 10/2019 |
| WO | WO 2020/006248 A1 | 2/2020 |

OTHER PUBLICATIONS

International Search Report and Written Opinion dated Sep. 11, 2017, for International Application No. PCT/US2017/037890, 5 pages.

International Search Report and Written Opinion for International Application No. PCT/US2018/067850, dated Sep. 24, 2019, 9 pages.

International Search Report and Written Opinion for International Application No. PCT/US2019/039530, dated Nov. 5, 2019, 11 pages.

Office Action for U.S. Appl. No. 15/855,555, dated Oct. 9, 2019, 9 pages.

Office Action for U.S. Appl. No. 16/038,657, dated Jan. 22, 2019, 11 pages.

Supplementary European Search Report for European Application No. 14775010.3, dated Sep. 30, 2016, 11 pages.

Alexeev et al., "High ionic strength glucose-sensing photonic crystal," Anal. Chem., 75:2316-2323 (2003).

Badylak et al., "Immune response to biologic scaffold materials," Seminars in Immunology, 20(2):109-116 (2008).

Borisov, S. M. et al., "Red light-excitable oxygen sensing materials based on platinum(II) and palladium(II) benzoporphyrins," Analytical Chemistry, 80(24):9435-9442 (Dec. 2008).

Braun et al., "Comparison of tumor and normal tissue oxygen tension measurements using oxylite or microelectrodes in rodents," Am. J. Physiol. Heart Circ. Physiol., 280(6):H2533-H2544 (2001).

Bridges et al., "Chronic inflammatory responses to microgel-based implant coatings," J Biomed. Mater. Res. A., 94(1):252-258 (2010).

Butkevich et al., "Hydroxylated Fluorescent Dyes for Live-Cell Labeling: Synthesis, Spectra and Super-Resolution STED," Chemistry. Sep. 7, 2017;23(50):12114-12119.

Cherevatskaya, M. et al. "Visible-Light-Promoted Stereoselective Alkylation by Combining Heterogeneous Photocatalysis with Organocatalysis," Angew. Chem. Int. Ed., 51(17), 4062-4066, 2012.

Cui, J. et al., "Design, Synthesis and Biological Evaluation of Rose Bengal Analogues as SecA Inhibitors," ChemMedChem 2013, 8 (8), 1384-1393.

Dunphy, I. et al., "Oxyphor R2 and G2: phosphors for measuring oxygen by oxygen-dependent quenching phosphorescence," Anal. Biochem., 310:191-198 (2002).

Everson et al., "Nickel-Catalyzed Cross-Coupling of Aryl Halides with Alkyl Halides: Ethyl 4-(4-(4-methylphenylsulfonamido)-phenyl)butanoate," Organic Synth. 2013;90:200-214.

Grimm, J. B. et al., "General Synthetic Method for Si-Fluoresceins and Si-Rhodamines," ACS Cent. Sci. 2017, 3 (9), 975-985.

Hutter, L. H. et al., "Robust optical oxygen sensors based on polymer-bound NIR-emitting platinum(II)-benzoporphyrins," J. Mat. Chem. C., 36:7589-7598 (Jul. 2014).

Isenhath et al., "A mouse model to evaluate the interface between skin and a percutaneous device," J Biomed. Mater. Research, 83A:915-922 (2007).

Jokic, T. et al., "Highly Photostable Near-Infrared Fluorescent pH Indicators and Sensors Based on BF2-Chelated Tetraarylazadipyrromethene Dyes," Anal. Chem. 2012, 84 (15), 6723-6730.

Ju et al., "A novel porous collagen scaffold around an implantable biosensor for improving biocompatibility. I. In vitro/in vivo stability of the scaffold and in vitro glucose sensitivity of the glucose sensor with scaffold," Journal of Biomedical Materials Research Part A., 2008, vol. 87, pp. 136-146.

Kaehr et al., "Multiphoton fabrication of chemically responsive protein hydrogels for microactuation," PNAS USA, 105(26):8850-8854 (2008).

Kasibhatla et al, "AMP deaminase inhibitors. 3. SAR of 3-(carboxyarylalkyl)coformycin aglycon analogues," J Med Chem. Apr. 20, 2000;43(8):1508-18.

(56) References Cited

OTHER PUBLICATIONS

Kasprzak, S. E., "Small-scale polymer structures enabled by thiol-ene copolymer systems," Doctoral Dissertation, Georgia Institute of Technology, May 2009, 170 pages.
Klonoff, "Overview of Fluorescence Glucose Sensing: A Technology with a Bright Future," Journal of Diabetes Science and Technology, vol. 6, Issue 6, Nov. 2012, 1242-1250.
Kloxin, A. M. et al., "Photodegradable hydrogels for dynamic tuning of physical and chemical properties," Science, 324:59-63 (2009).
Koide, et al., "Development of NIR Fluorescent Dyes Based on Si-rhodamine for in Vivo Imaging," J. Am. Chem. Soc., 2012, 134(11), 5029-5031.
Kumar A. et al., "Smart polymers: Physical forms and bioengineering applications," Prog. Polym. Sci. 32 (2007) 1205-1237.
Marshall et al., "Biomaterials with tightly controlled pore size that promote vascular in-growth," ACS Polymer Preprints, 45(2):100-101 (2004).
Menard et al., "Synthesis of tetraglucosyl- and tetrapolyamine-tetrabenzoporphyrin conjugates for an application in PDT," Bioorganic & Medicinal Chemistry, 17 (2009) 7647-7657, 11 pages.
Musial et al. "Morphological patterns of poly(N-isopropylacrylamide) derivatives synthesized with EGDMA, DEGDMA, and TEGDMA crosslinkers for application as thermosensitive drug carriers," Chemical Papers 64 (6) 791-798, Jun. 19, 2010.
Myochin, T. et al., "Development of a Series of Near-Infrared Dark Quenchers Based on Si-rhodamines and Their Application to Fluorescent Probes," J. Am. Chem. Soc. 2015, 137 (14), 4759-4765.
Nielson, R. et al., "Microreplication and design of biological architectures using dynamicmask multiphoton lithography," Small, 5(1):120-125 (2009).
Ostendorf, A. et al., "Two-photon polymerization: a new approach to micromachining," Photonics Spectra, 40(10):72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Quaranta et al., "Indicators for optical oxygen sensors," Bioanal Rev. Dec. 2012; 4(2-4): 115-157.
Rietveld, I. B. et al., "Dendrimers with tetrabenzoporphyrin cores: near infra-red phosphors for in vivo oxygen imaging," Tetrahedron, 59, 3821-3831, 2003.
Sanders et al., "Tissue response to single-polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Tian et al., "Influence of matrices on oxygen sensing of three-sensing films with chemically conjugated platinum porphyrin probes and preliminary application for monitoring of oxygen consumption of *Escherichia coli* (*E. coli*)," Sensors and Actuators B, 150:579-587 (2010).
Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chemistry Materials, 22(6):2069-2078 (2010).
Umezawa, K. et al., "Rational design of reversible fluorescent probes for live-cell imaging and quantification of fast glutathione dynamics," Nat. Chem. 2016, 9 (3), 279-286.
Vinogradov, S. A. et al., "Pd tetrabenzoporphyrin-dendrimers: near-infrared phosphors for oxygen measurements by phosphorescense quenching," Proc. SPIE, 4626:193-200 (2002).
Wang et al., "Recent Developments in Blood Glucose Sensors," Journal of Food and Drug Analysis 23 (2015) 191-200.
Wikipedia, "N,N'-Methylenebisacrylamide", Aug. 19, 2017 (Aug. 19, 2017), retrieved on Sep. 4, 2019 from https://en.wikipedia.org/w/index.php?title=N,N%27-Methylenebisacrylamide&oldid=796249249; entire document, 2 pages, especially p. 1 para 1.
Zhou et al., "Nebraska Red: a phosphinate-based near-infrared fluorophore scaffold for chemical biology applications," Chem Commun (Camb). Oct. 11, 2016;52(83):12290-12293.
Brito-Bensimon, A., et al., "Revisiting in Vivo Staining With Alizarin Red S—a Valuable Approach to Analyse Zebrafish Skeletal Mineralization During Development and Regeneration," BMC developmental biology, Jan. 19, 2016, vol. 16(2).
Chinese Office Action for Application No. CN201810435907 dated Jan. 4, 2022, 12 pages.
Extended European Search Report for European Application No. 20193383.5, dated Feb. 19, 2021, 13 pages.
Hansen et al., "Recent Advances in Fluorescent Arylboronic Acids for Glucose Sensing", Biosensors, 2013, vol. 3, p. 400-418 (Publication date: Oct. 12, 2013).
Indian Office Action for Application No. 202117001183 dated Aug. 1, 2022, 6 Pages.
Japanese Office Action for Application No. JP20190531268 dated Jan. 21, 2022, 11 pages.
Non-Final Office Action for U.S. Appl. No. 16/883,355, dated Jun. 9, 2022, 11 pages.
Notice of Allowance for U.S. Appl. No. 16/235,278 dated Aug. 8, 2022, 08 pages.
Office Action for Australian application No. AU20170388213, dated Sep. 13, 2022, 4 pages.
Office Action dated Oct. 9, 2021 for Chinese Application No. 201780079401.2, 23 pages.
Tian et al., "Dually fluorescent sensing of PH and dissolved oxygen using a membrane made from polymerizable sensing monomers," Sensors and Actuators B, 147:714-722 2010).
Alexandre, et al., "7-Hydroxycoumarin-Hemicyanine Hybrids: A New Class of Far-Red Emitting Fluorogenic Dyes". Organic Letters, 10(19): 4175-4178 (2008).
Andersen, et al., "Etiology and therapeutic approach to elevated lactate". Mayo Clin Proc, 88(10): 1127-1140 (Oct. 2013).
Extended European Search Report dated Feb. 28, 2022, for European Application No. 19826139.8, 8 pages.
Goncalves, "Fluorescent labeling of biomolecules with organic probes". Chem. Rev. 109(1): 190-212 (2009).
Gu, et al., "2-Styrylindolium based fluorescent probes visualize neurofibrillary tangles in Alzheimer's disease". Bioorganic & Medicinal Chemistry Letters, 22(24): 7667-7671 (2012).
Kukrer, et al., "Red to near IR fluorescent signalling of carbohydrates". Tet. Lett., 40(51): 9125-9128 (Dec. 1999).
Mishra, A., et al., "Cyanines during the 1990s: a review". Chem. Rev. 100(6): 1973-2011 (2000).
Park, et al., "Novel Cyanine Dyes with Vinylsulfone Group for Labeling Biomolecules". Bioconjugate Chem. 23(3): 350-362 (2012).
Staudinger et al., "Long-wavelength analyte-sensitive luminescent probes and optical bio)sensors," Methods and Applications in Fluorescence, vol. 3, pp. 1-37, Oct. 2015.
Zhang, L., "A Polymer-based Ratiometric Intracellular Glucose Sensor", Chemical communications, 2014, vol. 50(52), pp. 6920-6922.

* cited by examiner

POLYMERIZABLE NEAR-IR DYES

CROSS-REFERENCE TO RELATED APPLICATION

The present application is a continuation of International Application No. PCT/US2017/067847, filed Dec. 21, 2017, which claims priority to U.S. Provisional Application No. 62/437,599 filed Dec. 21, 2016, each of which is incorporated herein by reference in their entireties for all purposes.

BACKGROUND

Fluorescent polymers are functionalized macromolecules that find numerous applications in the fields of materials and life sciences and can be used as fluorescent probes, smart polymeric sensors, drug delivery carriers, and the like. Various methods of design and synthesis of fluorescent polymers have been developed in the art. Traditionally, fluorescent polymers are synthesized by chemical conjugation between activated fluorescent dye compounds and polymers bearing modifiable or reactive groups. This approach has several drawbacks: the activated dye derivatives are usually unstable and are prone to decomposition or side reactions, and the degree of polymer modification could be hard to control. To overcome these issues, methods of fluorescent polymer synthesis via direct polymerization of fluorescent functional monomers or fluorescent chain transfer agents have been developed. Although these methods have certain advantages, such as the ability to easily produce fluorescent polymers of defined architecture and degree of modification by varying the feed ratio of fluorescent to non-fluorescent monomers, they cannot be used to synthesize polymers bearing fluorescent groups that are incompatible with the polymerization conditions. For example, in some applications it is advantageous to use cyanine dyes because of their favorable spectral properties, such as high extinction coefficients and near-IR emission maxima; however, cyanine dyes are incompatible with radical polymerization conditions, for instance, those typically used to produce ethylenic-backbone polymers via controlled polymerization reactions such as RAFT.

Thus, until the present disclosure there remains a clear need in the art to provide near-IR, e.g., cyanine dye monomers, that are compatible with radical polymerization conditions and can form polymers, e.g., hydrogels, with fluorescent properties substantially similar to those of the monomers.

SUMMARY

In a first aspect, the disclosure features a compound having a structure of formula (I):

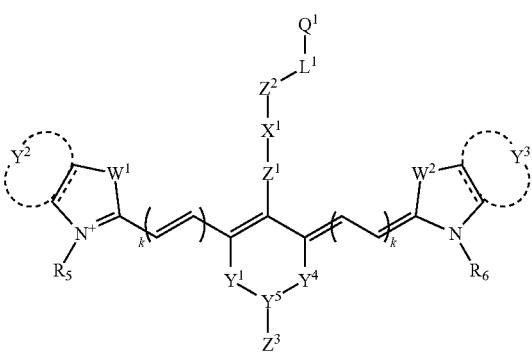

and its tautomers, isomers, salts, hydrates or solvates, wherein:

$Z^1$ is absent, O, $NR^{Z1}$, or S;

$R^{Z1}$ is H, optionally substituted $C_1$-$C_{10}$ alkyl, or optionally substituted $C_2$-$C_{10}$ heteroalkyl;

$X^1$ is absent, an optionally substituted $C_6$-$C_{10}$ arylene or an optionally substituted $C_1$-$C_{10}$ heteroarylene;

$Z^2$ is absent, $NR^{X1}$, O, S, $NR^{X2}C(O)$, OC(O), SC(O), C(O)O, C(O)$NR^{X3}$, C(S)O or C(O)S;

$Z^3$ is absent or H;

$R^{X1}$, $R^{X2}$ and $R^{X3}$ are each independently H, optionally substituted $C_1$-$C_{10}$ alkyl or optionally substituted $C_1$-$C_{10}$ heteroalkyl;

$L^1$ is absent, optionally substituted $C_6$-$C_{30}$ alkylene or optionally substituted $C_1$-$C_{30}$ heteroalkylene;

$Q^1$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$;

$R^{Z3}$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

$R^{Q1}$ is H, Me, Et, or n-Pr;

each of $Y^1$ and $Y^4$, independently, is absent or optionally substituted $C_1$-$C_4$ alkylene or optionally substituted $C_2$-$C_4$ heteroalkylene;

each of $Y^2$ and $Y^3$, independently, is absent or, together with the carbon atoms to which each is attached, form optionally substituted $C_6$-$C_{10}$ aryl or optionally substituted $C_2$-$C_{10}$ heteroaryl;

$Y^5$ is absent or N or $CR^7$;

$R^7$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

each of $W^1$ and $W^2$, independently, is $NR^2$, S, O, Se, or $CR^3R^4$;

$R^2$, $R^3$ and $R^4$ are independently H, optionally substituted $C_1$-$C_{30}$ alkyl, optionally substituted $C_1$-$C_{30}$ heteroalkyl, or -$L^2$-$Q^2$;

$L^2$ is optionally substituted $C_1$-$C_{30}$ alkylene or optionally substituted $C_1$-$C_{30}$ heteroalkylene;

$Q^2$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$;

each of $R^5$ and $R^6$, independently, is -$L^3$-$Q^3$, optionally substituted $C_1$-$C_{30}$ alkyl, or optionally substituted $C_6$-$C_{10}$ aryl;

$X^3$ is absent or $L^3$-$Q^3$;

$L^3$ is optionally substituted $C_1$-$C_{30}$ alkylene or optionally substituted $C_1$-$C_{30}$ heteroalkylene;

$Q^3$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$; and each k is independently 0 or 1;

with the proviso that the compound comprises at least one polymerizable group.

In some embodiments of formula (I), $Z^1$ is absent. In certain embodiments of formula (I), $Z^1$ is O. In other embodiments of formula (I), $Z^1$ is $NR^{Z1}$. In yet other embodiments of formula (I), $Z^1$ is S.

In certain embodiments of formula (I), $W^1$ is $NR^2$. In other embodiments of formula (I), $W^1$ is S. In yet other embodiments of formula (I), $W^1$ is O. In still other embodiments of formula (I), $W^1$ is Se. In alternative embodiments of formula (I), $W^1$ is $CR^3R^4$.

In some embodiments of formula (I), $W^2$ is $NR^2$. In other embodiments of formula (I), $W^2$ is S. In yet other embodiments of formula (I), $W^2$ is O. In still other embodiments of formula (I), $W^2$ is Se. In alternative embodiments of formula (I), $W^2$ is $CR^3R^4$.

In some embodiments of formula (I), the compound has a structure of formula (IA):

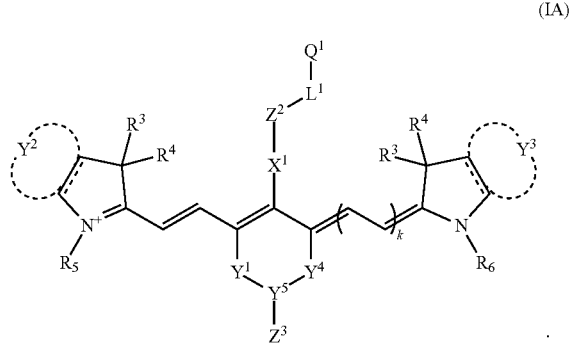

(IA)

In some embodiments of formula (I) or (IA), each of $R^3$ is, independently, H, optionally substituted $C_1$-$C_{30}$ alkyl, or optionally substituted $C_1$-$C_{30}$ heteroalkyl. In certain embodiments of formula (I) or (IA), each of $R^3$ is, independently, optionally substituted $C_1$-$C_5$ alkyl. In certain embodiments of formula (I) or (IA), each of $R^3$ is methyl. In yet other embodiments of formula (I) or (IA), each of $R^3$ is, independently, $C_1$-$C_5$ alkyl substituted with $SO_3H$ or $C_1$-$C_5$ alkyl substituted with $B(OH)_2$.

In some embodiments of formula (I) or (IA), each of $R^4$ is, independently, H, optionally substituted $C_1$-$C_{30}$ alkyl, or optionally substituted $C_1$-$C_{30}$ heteroalkyl. In certain embodiments of formula (I) or (IA), each of $R^4$ is, independently, optionally substituted $C_1$-$C_5$ alkyl. In certain embodiments of formula (I) or (IA), each of $R^4$ is methyl. In yet other embodiments of Formula (I) or Formula (IA), formula (I) or (IA), each of $R^4$ is, independently, $C_1$-$C_5$ alkyl substituted with $SO_3H$ or $C_1$-$C_5$ alkyl substituted with $B(OH)_2$.

In some embodiments of formula (I) or (IA), the compound has a structure of Formula (IB):

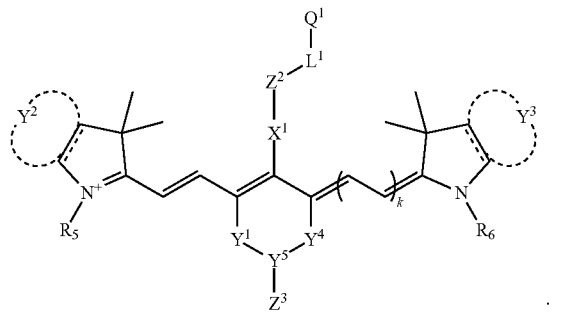

(IB)

In some embodiments of formula (I), (IA), or (IB), $Y^2$, together with the carbon atoms to which it is attached, form optionally substituted $C_6$-$C_{10}$ arylene or optionally substituted $C_2$-$C_{10}$ heteroarylene. In certain embodiments of formula (I), (IA), or (IB), $Y^2$, together with the carbon atoms to which it is attached, form an optionally substituted $C_6$ arylene or an optionally substituted $C_{10}$ arylene. In other embodiments of formula (I), (IA), or (IB), $Y^2$, together with the carbon atoms to which it is attached, form a $C_6$ arylene substituted with 1 or 2 sulfo groups or a $C_{10}$ arylene substituted with 1 or 2 sulfo groups.

In some embodiments of formula (I), (IA), or (IB), $Y^3$, together with the carbon atoms to which it is attached, form optionally substituted $C_6$-$C_{10}$ arylene or optionally substituted $C_2$-$C_{10}$ heteroarylene. In certain embodiments of formula (I), (IA), or (IB), $Y^3$, together with the carbon atoms to which it is attached, form an optionally substituted $C_6$ arylene or an optionally substituted $C_{10}$ arylene. In other embodiments of formula (I), (IA), or (IB), $Y^3$, together with the carbon atoms to which it is attached, form a $C_6$ arylene substituted with 1 or 2 sulfo groups or a $C_{10}$ arylene substituted with 1 or 2 sulfo groups.

In some embodiments of formula (I), (IA), or (IB), the compound has a structure of formula (IC):

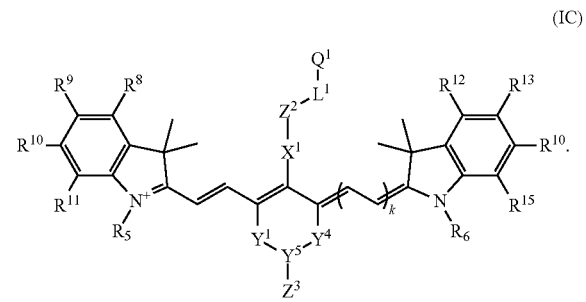

(IC)

wherein each of $R^8$-$R^{15}$ is, independently, H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, hydroxy; or, any two $R^8$-$R^{15}$ in the ortho position to each other, together with the carbon atoms to which each is attached, form an optionally substituted benzylene.

In some embodiments of formula (I), (IA), (IB), or (IC), $R^{10}$ is H. In certain embodiments of formula (I), (IA), (IB), or (IC), $R^{11}$ is H. In other embodiments of formula (I), (IA), (IB), or (IC), $R^{14}$ is H. In yet other embodiments of formula (I), (IA), (IB), or (IC), $R^{15}$ is H.

In some embodiments of formula (I), (IA), (IB), or (IC), the compound has a structure of Formula (ID):

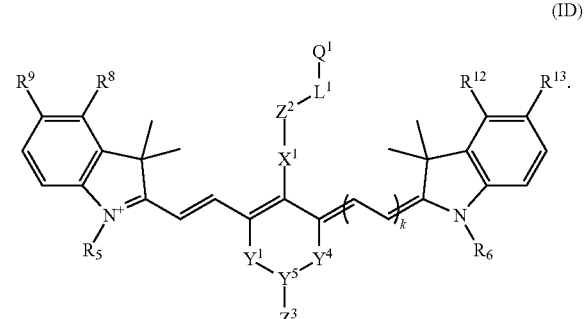

(ID)

In some embodiments of formula (I), (IA), (IB), (IC), or (ID), $R^8$ is H. In certain embodiments of formula (I), (IA), (IB), (IC), or (ID), $R^{12}$ is H. In other embodiments of formula (I), (IA), (IB), (IC), or (ID), $R^{13}$ is sulfo group. In yet other embodiments of formula (I), (IA), (IB), (IC), or (ID), $R^9$ is sulfo group.

In particular embodiments of formula (I), (IA), (IB), (IC), or (ID), $R^8$ and $R^9$, together with the carbon atoms to which each is attached, form optionally substituted benzylene (e.g., a benzylene substituted with 1 or 2 sulfo groups). In other embodiments of formula (I), (IA), (IB), (IC), or (ID), $R^{12}$ and $R^{13}$, together with the carbon atoms to which each is attached, form optionally substituted benzylene (e.g., a benzylene substituted with 1 or 2 sulfo groups).

In certain embodiments of formula (I), (IA), (IB), (IC), or (ID), $R^{10}$ is H. In other embodiments of formula (I), (IA), (IB), (IC), or (ID), $R^{11}$ is H. In further embodiments of formula (I), (IA), (IB), (IC), or (ID), $R^{14}$ is H. In yet alternative embodiments of formula (I), (IA), (IB), (IC), or (ID), $R^{15}$ is H.

In some embodiments of formula (I), (IA), (IB), (IC), or (ID), the compound has a structure of Formula (IE):

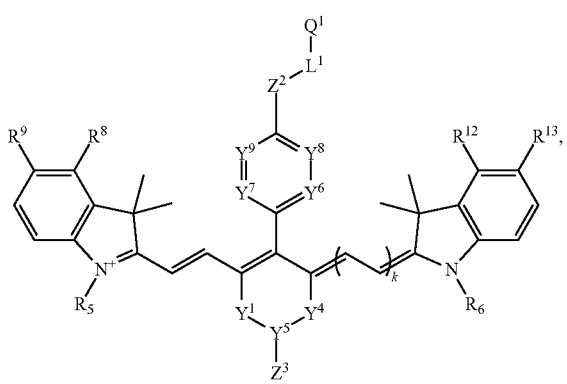

(IE)

wherein each of $Y^6$, $Y^7$, $Y^8$, and $Y^9$ is, independently, N or $CR^{16}$; and $R^{16}$ is H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, or hydroxy.

In some embodiments of formula (I), (IA), (IB), (IC), (ID), or (IE), $Y^6$ is N. In other embodiments of embodiments of formula (I), (IA), (IB), (IC), (ID), or (IE), $Y^7$ is $CR^{16}$. In yet other embodiments of formula (I), (IA), (IB), (IC), (ID), or (IE), $Y^8$ is $CR^{16}$. In still other embodiments of formula (I), (IA), (IB), (IC), (ID), or (IE), $Y^9$ is $CR^{16}$.

In certain embodiments of formula (I), (IA), (IB), (IC), (ID), or (IE), $Q^1$ is $Y^{10}C(O)CR^{Q1}CH_2$, wherein $Y^{10}$ is O, S, or $NR^{Z3}$.

In some embodiments of formula (I), (IA), (IB), (IC), (ID), or (IE), the compound has a structure of formula (IF):

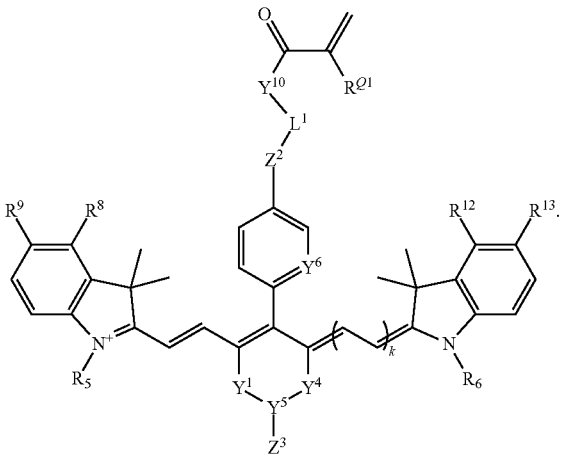

(IF)

In some embodiments of formula (I), (IA), (IB), (IC), (ID), (IE), or (IF), $Y^{10}$ is absent. In other embodiments of formula (I), (IA), (IB), (IC), (ID), (IE), or (IF), $Y^{10}$ is O. In yet other embodiments of formula (I), (IA), (IB), (IC), (ID), (IE), or (IF), $Y^{10}$ is NH.

In certain embodiments of formula (I), (IA), (IB), (IC), (ID), (IE), or (IF), $R^{Q1}$ is H or $C_1$-$C_3$ alkyl. In other embodiments of formula (I), (IA), (IB), (IC), (ID), (IE), or (IF), $R^{Q1}$ is H or methyl. In particular embodiments of formula (I), (IA), (IB), (IC), (ID), (IE), or (IF), $R^{Q1}$ is methyl.

In some embodiments of formula (I), (IA), (IB), (IC), (ID), (IE), or (IF), the compound has a structure of Formula (IG):

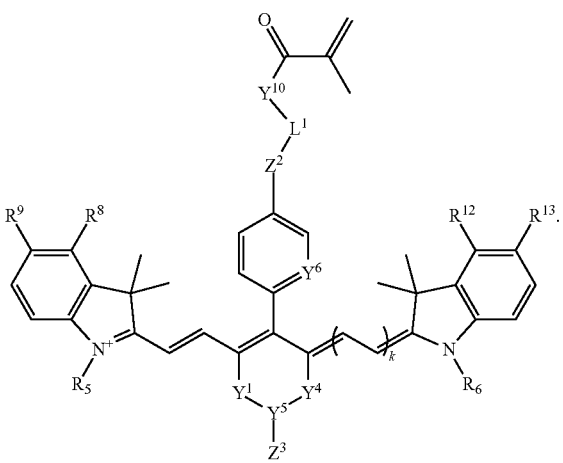

(IG)

In certain embodiments of formula (I), (IA), (IB), (IC), (ID), (IE), (IF), or (IG), $R^5$ is optionally substituted $C_1$-$C_{30}$ alkyl, or optionally substituted $C_6$-$C_{10}$ aryl. In other embodiments of formula (I), (IA), (IB), (IC), (ID), (IE), (IF), or (IG), $R^5$ is $C_1$-$C_6$ alkyl substituted with $SO_3H$ or $C_1$-$C_6$ alkyl substituted with $B(OH)_2$.

In certain embodiments of formula (I), (IA), (IB), (IC), (ID), (IE), (IF), or (IG), $R^6$ is optionally substituted $C_1$-$C_{30}$ alkyl, or optionally substituted $C_6$-$C_{10}$ aryl. In other embodiments of formula (I), (IA), (IB), (IC), (ID), (IE), (IF), or (IG), $R^6$ is $C_1$-$C_6$ alkyl substituted with $SO_3H$ or $C_1$-$C_6$ alkyl substituted with $B(OH)_2$.

In some embodiments of formula (I), (IA), (IB), (IC), (ID), (IE), (IF), or (IG), the compound is listed in Table 1.

In a second aspect, the disclosure features a polymer comprising the residue of the compound of any of formulas (I), (IA), (IB), (IC), (ID), (IE), (IF), or (IG) as a monomeric unit.

In certain embodiments, the polymer comprises at least one monomer selected from HEMA (hydroxyethyl methacrylate), DMA (N,N-Dimethylacrylamide), HPA (Hydroxypropyl acrylate), methyl methacrylate, acrylamide, PEGMA (polyethyleneglycol methacrylate), methacrylic acid, hydroxyethyl acrylate, N-vinyl pyrrolidone, acrylamide, methacryloylaminopropyl trimethylammonium chloride, diallyl dimethyl ammonium chloride, vinyl benzyl trimethyl ammonium chloride, and sodium sulfopropyl methacrylate.

In other embodiments, the polymer is a homopolymer. In alternative embodiments, the polymer is a copolymer. In some embodiments, the polymer is crosslinked. In yet other embodiments, the polymer is a hydrogel. In some embodiments, the polymer is a tissue-integrating hydrogel.

In some embodiments, the polymer is a luminescent polymer. In other embodiments, the polymer is a near-IR fluorescent polymer and has an emission wavelength between about 600 and 1000 nm, about 650 nm and 900 nm, or between about 650 nm and 850 nm. In some embodiments, the emission and absorption maxima of the monomer are unchanged upon incorporation into the polymer.

In some embodiments, the polymer is a component of an interpenetrating network.

DETAILED DESCRIPTION

Figure 1:
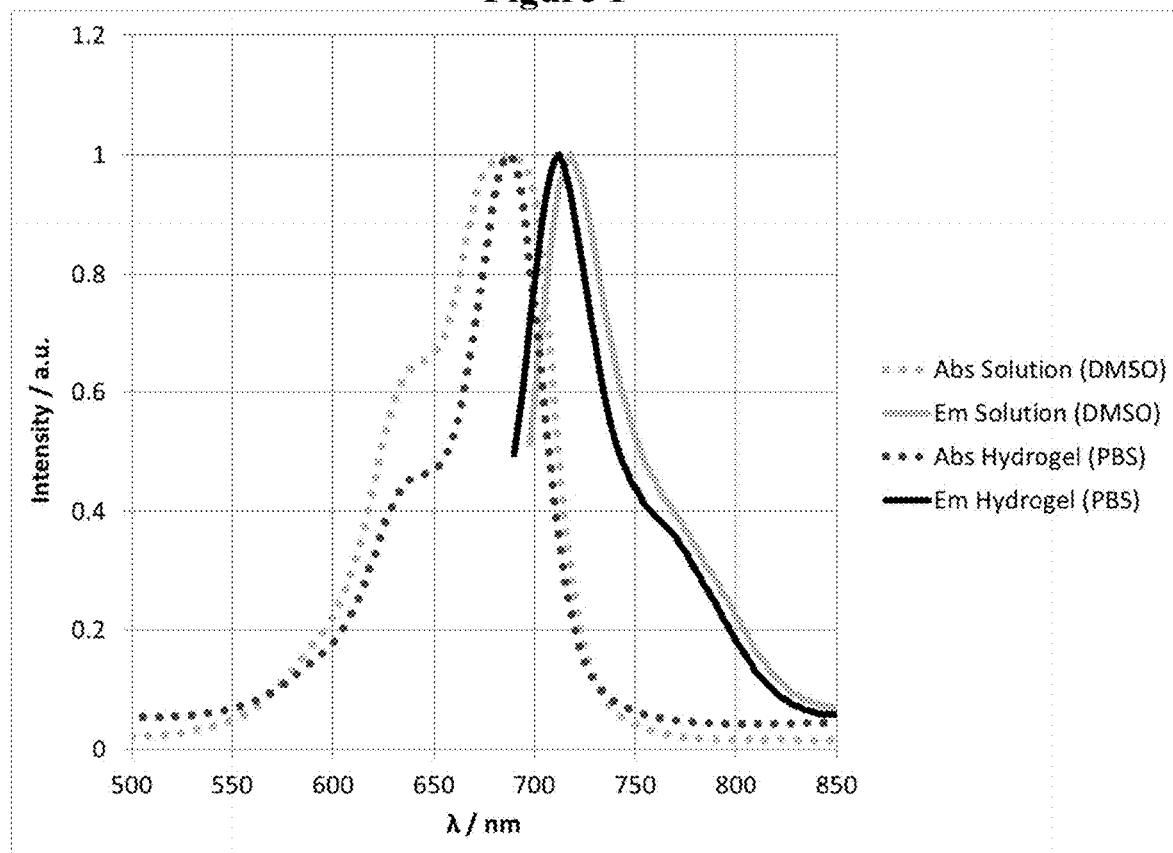
FIG. 1 depicts the absorbance/emission spectra of a polymerizable near-IR dye (compound 36; Cy5.5-2SA-L1) in DMSO compared to the absorbance/emission of an aqueous hydrogel comprising (compound 36; Cy5.5-2SA-L1) and pHEMA in PBS.
Figure 2:
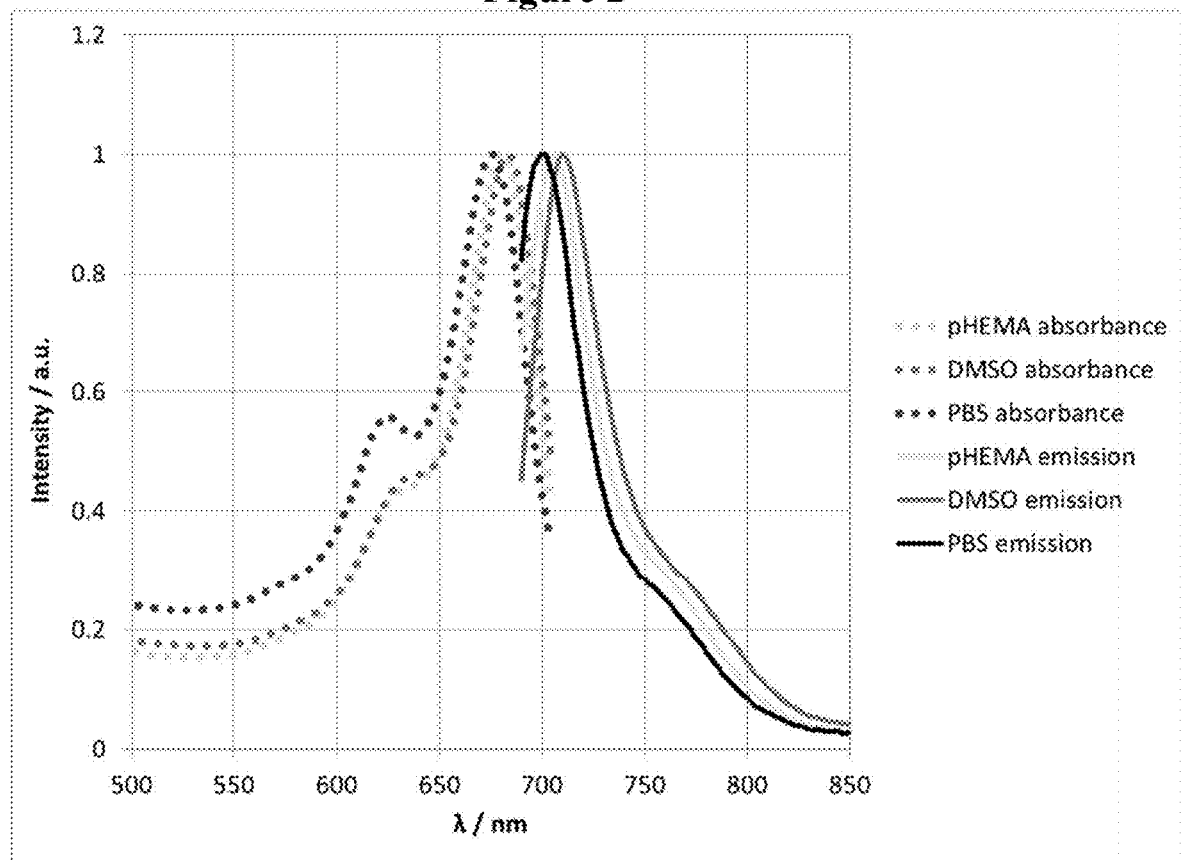
FIG. 2 depicts the absorbance/emission spectra of a polymerizable near-IR dye (compound 17; Cy5.5-6SA-L1) in DMSO and in PBS, compared to the absorbance/emission spectra of a hydrogel comprising said polymerizable near-IR dye and pHEMA in DMSO and PBS.

Described herein are polymerizable near-IR fluorescent dyes useful for incorporation into polymers and polymers comprising as monomeric units residues of the dyes of the present disclosure. The dyes and the polymers are useful, for example, in sensing and imaging applications, such as but not limited to, accurate and optionally long term measurements of pH both in vivo and in vitro.

It must be noted that, as used in this specification and the appended claims, the singular forms "a", "an", and "the" include plural referents unless the content clearly dictates otherwise. Thus, for example, reference to a polymer comprising "a fluorescent moiety" includes polymers comprising one or two or more fluorescent moieties. Likewise, reference to "a monomer" may refer to two or more monomers.

Advantages of the dyes and fluorescent polymers provided herein include, but are not limited to: (1) excitation and emission wavelengths in the near-IR region (approximately 550 nm to 1000 nm) allowing detection of analytes deep within a tissue or an organ; (2) high signal-to-noise ratio; (3) compatibility with polymerization conditions used to produce polymers with ethylenic backbones.

Definitions

Unless defined otherwise, all technical and scientific terms used herein have the same meaning as commonly understood by one of ordinary skill in the art to which this disclosure is related. The following terms are defined for the purposes of understanding the present disclosure.

The term "hydrogel" is meant to describe a material that absorbs a solvent (e.g., water), undergoes swelling without discernible dissolution, and maintains three-dimensional networks capable of reversible deformation.

The term "tissue integrating" refers to a material (e.g., scaffold) which, when integrated into living tissue remains in close proximity with the blood vessels of the tissue (e.g., capillaries). By "close proximity," is meant that the average distance from any point within the material (scaffold) implanted into the tissue to the nearest blood vessel is no greater than 100 microns more than the average distance from any point in the native (original) tissue to the nearest blood vessel.

The term "cyanine dye" as used herein refers to a fluorogenic or a luminescent compound that comprises 1) an optionally substituted benzazolium moiety, 2) a polymethine bridge and 3) an optionally substituted benzazolium, pyridinium or quinolinium moiety.

The term "polymerizable group" refers to a moiety that is capable of reacting with a second moiety to form a polymer. In some embodiments, the "polymerizable group" refers to a moiety which is capable of undergoing free radical polymerization with a second moiety to form a polymer. Moieties which react to form polymers according to the present disclosure can be the same or different. Examples of polymerizable groups include, but are not limited to, vinyl groups, such as acrylates (e.g., acrylic acid derivatives, methylacrylate, acrylamide, etc). Non-limiting examples of acrylate groups which can be used in the present disclosure include HEMA (hydroxyethyl methacrylate), DMA (N,N-Dimethylacrylamide), HPA (Hydroxypropyl acrylate), methyl methacrylate, acrylamide, PEGMA (polyethyleneglycol methacrylate), methacrylic acid, hydroxyethyl acrylate, N-vinyl pyrrolidone, acrylamide, methacryloylaminopropyl trimethylammonium chloride, diallyl dimethyl ammonium chloride, vinyl benzyl trimethyl ammonium chloride, and sodium sulfopropyl methacrylate. In some embodiments, the polymerizable groups is bound (directly or indirectly through a linker group) to a near-IR dye (e.g., cyanine dye).

The term "polymerizable near-IR dye" refers to monomeric unit comprising a near-IR dye (e.g., cyanine dye) and a polymerizable group.

Polydispersity refers to the distribution of molecular mass in a polymer. In some embodiments, the polymers described herein can have a polydispersity index of 1 to 2, e.g., 1.1, 1.2, 1.3, 1.4, 1.5, 1.6, 1.7, 1.8, and 1.9.

"Tacticity" refers to the relative stereochemistry of adjacent chiral centers in a polymer. In some embodiments, the polymers described herein can be isotactic, syndiotactic, or actactic.

A. Polymerizable Fluorescent Dyes

In one aspect, this disclosure provides a polymerizable dye of formula (I):

(I)

and its tautomers, isomers, salts, hydrates or solvates, wherein:

$Z^1$ is absent, O, $NR^{Z1}$, or S;

$R^{Z1}$ is H, optionally substituted $C_1$-$C_{10}$ alkyl, or optionally substituted $C_2$-$C_{10}$ heteroalkyl;

$X^1$ is absent, an optionally substituted $C_6$-$C_{10}$ arylene or an optionally substituted $C_1$-$C_{10}$ heteroarylene;

$Z^2$ is absent, $NR^{X1}$, O, S, $NR^{X2}C(O)$, OC(O), SC(O), C(O)O, $C(O)NR^{X3}$, C(S)O or C(O)S;

$Z^3$ is absent or H;

$R^{X1}$, $R^{X2}$ and $R^{X3}$ are each independently H, optionally substituted $C_1$-$C_{10}$ alkyl or optionally substituted $C_1$-$C_{10}$ heteroalkyl;

$L^1$ is absent, optionally substituted $C_1$-$C_{30}$ alkylene or optionally substituted $C_1$-$C_{30}$ heteroalkylene;

$Q^1$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$;

$R^{Z3}$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

$R^{Q1}$ is H, Me, Et, or n-Pr;

each of $Y^1$ and $Y^4$, independently, is absent or optionally substituted $C_1$-$C_4$ alkylene or optionally substituted $C_2$-$C_4$ heteroalkylene;

each of $Y^2$ and $Y^3$, independently, is absent or, together with the carbon atoms to which each is attached, form optionally substituted $C_6$-$C_{10}$ aryl or optionally substituted $C_2$-$C_{10}$ heteroaryl;

$Y^5$ is N or $CR^7$;

$R^7$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

each of $W^1$ and $W^2$, independently, is $NR^2$, S, O, Se, or $CR^3R^4$;

$R^2$, $R^3$ and $R^4$ are independently H, optionally substituted $C_1$-$C_{30}$ alkyl, optionally substituted $C_1$-$C_{30}$ heteroalkyl, or -$L^2Q^2$;

$L^2$ is optionally substituted $C_1$-$C_{30}$ alkylene or optionally substituted $C_1$-$C_{30}$ heteroalkylene;

$Q^2$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$;

each of $R^5$ and $R^6$, independently, is -$L^3$-$Q^3$, optionally substituted $C_1$-$C_{30}$ alkyl, or optionally substituted $C_6$-$C_{10}$ aryl;

$X^3$ is absent or $L^3$-$Q^3$;

$L^3$ is optionally substituted $C_1$-$C_{30}$ alkylene or optionally substituted $C_1$-$C_{30}$ heteroalkylene;

$Q^3$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$; and each k is independently 0 or 1;

with the proviso that the compound comprises at least one polymerizable group.

In some embodiments of formula (I), $Z^1$ is absent. In certain embodiments of formula (I), $Z^1$ is O. In other embodiments of formula (I), $Z^1$ is $NR^{Z1}$. In yet other embodiments of formula (I), $Z^1$ is S.

In certain embodiments of formula (I), $W^1$ is $NR^2$. In other embodiments of formula (I), $W^1$ is S. In yet other embodiments of formula (I), $W^1$ is O. In still other embodiments of formula (I), $W^1$ is Se. In alternative embodiments of formula (I), $W^1$ is $CR^3R^4$.

In some embodiments of formula (I), $W^2$ is $NR^2$. In other embodiments of formula (I), $W^2$ is S. In yet other embodiments of formula (I), $W^2$ is O. In still other embodiments of formula (I), $W^2$ is Se. In alternative embodiments of formula (I), $W^2$ is $CR^3R^4$.

In some embodiments, the polymerizable near-IR dyes described herein can be of any molecular weight provided that said polymerizable near-IR dyes are soluble in the solution in which the polymerization reaction is performed. In some embodiments, the polymerizable near-IR dyes have a molecular weight in the range of from about 250 Da to about 10,000 Da, or of from about 300 Da to about 9,000 Da, or about 300 Da to about 8,000 Da, or about 300 Da to about 7,000 Da, or about 300 Da to about 6,000 Da, or about 300 Da to about 5,000 Da, or about 300 Da to about 4,000 Da, or about 300 Da to about 3,000 Da, or about 300 Da to about 2,000 Da, or about 300 Da to about 1,900 Da, or about 300 Da to about 1,800 Da, or about 300 Da to about 1,700 Da, or about 300 Da to about 1,600 Da, or about 300 Da to about 1,500 Da, or about 300 Da to about 1,400 Da, or about 300 Da to about 1,300 Da, or about 300 Da to about 1,200 Da, or about 300 Da to about 1,100, or about 300 Da to about 1,000 Da, or about 300 Da to about 900 Da, or about 300 Da to about 800 Da, or about 300 Da to about 700 Da, or about 300 Da to about 600 Da, or about 300 Da to about 500 Da, or about 500 Da to about 2,000 Da, or about 500 Da to about 1,900 Da, or about 500 Da to about 1,800 Da, or about 500 Da to about 1,700 Da, or about 500 Da to about 1,600 Da, or about 300 Da to about 1,500 Da, or about 500 Da to about 1,400 Da, or about 500 Da to about 1,300 Da, or about 500 Da to about 1,200 Da, or about 500 Da to about 1,100, or about 500 Da to about 1,000 Da, or about 500 Da to about 900 Da, or about 500 Da to about 800 Da, or about 500 Da to about 700 Da, or about 500 Da to about 600 Da, or about 800 Da to about 2,000 Da, or about 800 Da to about 1,900 Da, or about 800 Da to about 1,800 Da, or about 800 Da to about 1,700 Da, or about 800 Da to about 1,600 Da, or about 800 Da to about 1,500 Da, or about 800 Da to about 1,400 Da, or about 800 Da to about 1,300 Da, or about 800 Da to about 1,200 Da, or about 800 Da to about 1,100, or about 800 Da to about 1,000 Da, or about 800 Da to about 900 Da, or about 1,000 Da to about 2,000 Da, or about 1,000 Da to about 1,900 Da, or about 1,000 Da to about 1,800 Da, or about 1,000 Da to about 1,700 Da, or about 1,000 Da to about 1,600 Da, or about 1,000 Da to about 1,500 Da, or about 1,000 Da to about 1,400 Da, or about 1,000 Da to about 1,300 Da, or about 1,000 Da to about 1,200 Da, or about 1,000 Da to about 1,100.

In some embodiments, the polymerizable near-IR dyes of the present disclosure are compatible with the conditions of radical polymerization of vinyl compounds, e.g., styrene, acrylamide, or acrylic acid esters. In certain embodiments, the dye moiety of the polymerizable dyes does not undergo decomposition upon being subjected to the conditions of radical ethylenic polymerization.

In some embodiments, the polymerizable near-IR dyes of this disclosure exhibit absorption maxima in the range between about 500 nm and about 1000 nm, between about 600 nm and about 1000 nm, between about 700 nm and about 1000 nm, between about 600 nm and about 900 nm, between about 638 nm and about 822 nm, between about 638 nm and about 684 nm, or between about 772 nm and about 822 nm. In some embodiments, the polymerizable near-IR dyes this disclosure exhibit emission maxima in the range between about 600 nm and about 1000 nm, about 600 nm and about 950 nm, about 650 nm and about 900 nm, about 660 nm and about 850 nm, about 660 nm and about 706 nm, or about 796 nm and about 850 nm. In some embodiments, the polymerizable near-IR dyes are polymethine dyes, e.g., cyanine dyes. The spectral parameters of the polymerizable dyes, e.g., cyanine dyes, can be altered and/or tuned to the desired absorption/emission wavelengths by varying the structure of the dye, e.g., using either trimethine, or pentamethine linkages. For example, where the remainder of the compound is held constant, shifting from a trimethine linkage, to a pentamethine or to a heptamethine linkage typically results in a shifting of the absorption and emission wavelengths of the resulting compounds to progressively longer wavelengths, e.g. in the near IR region. The absorption maxima can be further fine-tuned by introduction of functional groups, e.g., electron donor or electron acceptor groups.

The polymerizable near-IR dyes of the present disclosure can be prepared in any suitable manner by any combination of standard chemical synthetic steps using methods readily known in the art. The synthetic schemes shown herein can be modified if necessary by routine measures to prepare dyes having different types of substitution.

In some embodiments, the polymerizable near-IR dyes of the present disclosure are polymethine dyes, e.g., cyanine dyes that comprise a methylene base and one or more aromatic rings. The synthesis of the polymerizable near-IR dyes of the present disclosure is achieved in a multi-step fashion, starting with the synthesis of a methylene base. Generally, the spectral properties of the dyes, including excitation and emission wavelengths, may be strongly dependent on the type of methylene base and/or types of substituents incorporated into the aromatic moieties. Non-limiting examples of the starting materials for the synthesis of the dyes include optionally substituted quarternized indolenines, optionally substituted benzthiazoles, optionally substituted benzoxazoles, optionally substituted benzimidazoles, N,N'-diphenylformamidine, and malonaldehyde bis (phenylimine) monohydrochloride. In particular embodiments, the synthesis of these methylene-bases is achieved via a Fischer indole synthesis using substituted phenyl-hydrazines and substituted aliphatic ketones. The resulting indolenine intermediates are subsequently quarternized with alkylating agents (e.g., methyl iodide, propanesultone, butanesultone or bromo-hexanoic acid), and then converted into cyanine dyes via methods known in the art. The synthesis of various classes of cyanine dyes is described in Gupta R R, Strekowski L (eds.) (2008) Heterocyclic polymethine dyes. Topics in Heterocyclic Chemistry, Vol. 14. Springer-Verlag, Berlin, Heidelberg; A. Mishra et al., Cyanines during the 1990s: a review. Chem. Rev. 100, 1973-2011 (2000); and Goncalves et al., Fluorescent labeling of biomolecules with organic probes. Chem. Rev. 109, 190-212, (2009), which are all incorporated herein by reference.

To further increase and facilitate water-solubility of the dyes and the polymers comprising the dye residues, ionizable or permanently charged groups such as sulfonic acid, quaternary ammonium, boronic acid, carboxyl, and phosphate, among others, may be introduced into the heterocyclic ring systems, in the bridging unit and/or the side chains. Polyether-containing groups, such as PEG, can be also used to increase water solubility and biocompatibility.

In a non-limiting example, one method of preparation of the dyes of the present disclosure involves conversion of intermediate A to a bromide intermediate B, which can undergo palladium-catalyzed Suzuki coupling to form a polymerizable dye having the formula (I), as depicted in Scheme 1A:

Scheme 1A

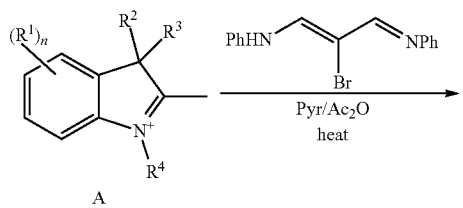

-continued

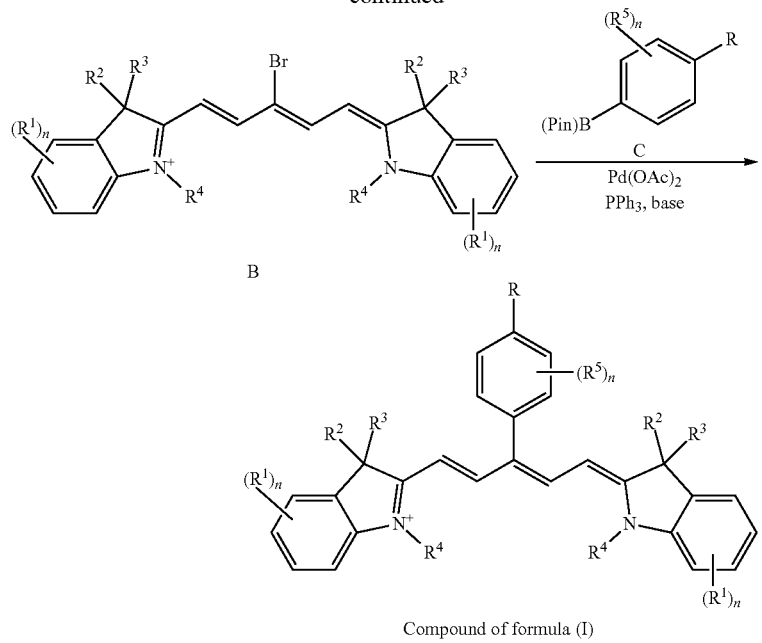

B

Compound of formula (I)

The polymerizable near-IR dyes, e.g., cyanine dyes of the present disclosure can be symmetrical and non-symmetrical. An example of preparation of the non-symmetrical cyanine dye is shown in the Scheme 1B:

Scheme 1B

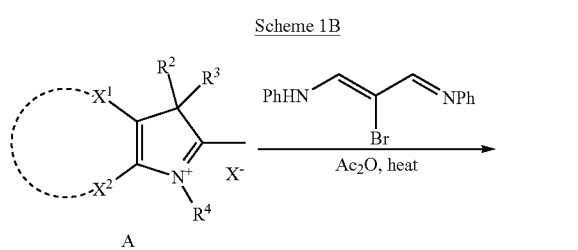

A

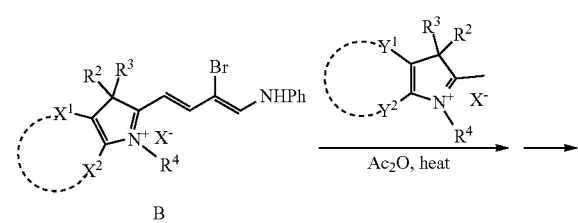

B

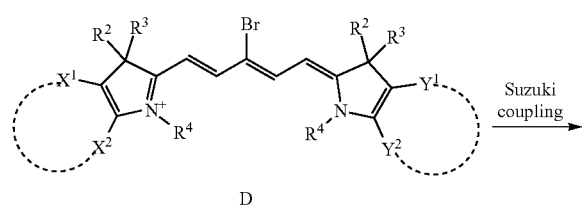

D

-continued

Compound of formula (I)

In some embodiments, the polymerizable near-IR dyes of the present disclosure can be used for the detection of an analyte, in vitro, or for diagnostic applications, in vitro and in vivo. For example, the polymerizable near-IR dye can be introduced to a composition comprising an analyte. In some embodiments, the analyte can functionalized with a compatible polymerizable group as described herein. In some embodiment, a recognition element which binds to an analyte can be functionalized with a compatible polymerizable group as described herein. The polymerization reaction can be performed, and the resulting fluorescent signal detected can be used to determine the presence/absence of the analyte.

B. Polymers

In a second aspect of the disclosure, provided herein are fluorescent polymers. The fluorescent dyes of the present disclosure comprise polymerizable groups, e.g., residue of acrylic, methacrylic, or ethacrylic acid, and can be co-polymerized with other monomers to provide polymers comprising fluorescent groups, e.g., near-IR fluorescent groups and/or having fluorescent properties. When the compounds have two or more polymerizable groups, the polymers obtained from their co-polymerization with other monomers can be crosslinked. Alternatively, another crosslinking monomer can be added into the polymerization mixture to achieve a higher degree of crosslinking of the resulting polymer.

The fluorescent polymers described herein can have any molecular weight provided that said polymer is suitable for its intended purpose, e.g., water soluble, biocompatible, bioresorbable, etc. In some embodiments, the fluorescent polymer described herein have a molecular weight in the range of: from about 500 Da to about 1,000,000 Da; from 500 Da to about 900,00 Da; from about 500 Da to about 800,000 Da; from about 500 Da to about 700,000 Da; from about 500 Da to about 600,000; from about 500 Da to about 500,000; from about 500 Da to about 400,000; from about 500 Da to about 300,000 Da; from about 500 Da to about 200,000 Da; from about 500 Da to about 100,000 Da; from about 500 Da to about 90,000 Da; from about 500 Da to about 80,000 Da; from about 500 Da to about 70,000 Da; from about 500 Da to about 60,000; from about 500 Da to about 50,000; from about 500 Da to about 40,000; from about 500 Da to about 30,000 Da; from about 500 Da to about 20,000 Da; from about 500 Da to about 10,000 Da; from about 500 Da to about 9,000 Da; from about 500 Da to about 8,000 Da; from about 500 Da to about 7,000 Da; from about 500 Da to about 6,000; from about 500 Da to about 5,000; from about 500 Da to about 4,000; from about 500 Da to about 3,000 Da; from about 500 Da to about 2,000 Da; from about 500 Da to about 1,000 Da; from about 1,000 Da to about 1,000,000 Da; from 1,000 Da to about 900,00 Da; from about 1,000 Da to about 800,000 Da; from about 1,000 Da to about 700,000 Da; from about 1,000 Da to about 600,000; from about 1,000 Da to about 500,000; from about 1,000 Da to about 400,000; from about 1,000 Da to about 300,000 Da; from about 1,000 Da to about 200,000 Da; from about 1,000 Da to about 100,000 Da; from about 1,000 Da to about 90,000 Da; from about 1,000 Da to about 80,000 Da; from about 1,000 Da to about 70,000 Da; from about 1,000 Da to about 60,000; from about 1,000 Da to about 50,000; from about 1,000 Da to about 40,000; from about 1,000 Da to about 30,000 Da; from about 1,000 Da to about 20,000 Da; from about 1,000 Da to about 10,000 Da; from about 1,000 Da to about 9,000 Da; from about 1,000 Da to about 8,000 Da; from about 1,000 Da to about 7,000 Da; from about 1,000 Da to about 6,000; from about 1,000 Da to about 5,000; from about 1,000 Da to about 4,000; from about 1,000 Da to about 3,000 Da; from about 1,000 Da to about 2,000 Da, including all values and subranges therein.

In some embodiments, the polymers of the present disclosure are homopolymers, i.e., polymers prepared by polymerization of the near-IR fluorescent monomer of the present disclosure. In other embodiments, the polymers of the present disclosure are heteropolymers, i.e., polymers prepared by co-polymerization of monomer of the present disclosure with a suitable fluorescent or non-fluorescent monomer of a different structure. In some embodiments, the ratio of fluorescent monomers to non-fluorescent monomers in heteropolymers is in the range of from about 10,000:1 to about 1:10,000; or from about 5,000:1 to about 1:5,000; or from about 1000:1 to about 1:1000; or from about 900:1 to about 1:900; or from about 800:1 to about 1:800; or from about 700:1 to about 1:700; or from about 600:1 to about 1:600; or from about 500:1 to about 1:500; or from about 400:1 to about 1:400; or from about 300:1 to about 1:300; or from about 200:1 to about 1:200; or from about 100:1 to about 1:100; or from about 90:1 to about 1:90; or from about 80:1 to about 1:80; or from 70:1 to about 1:70; or from about 60:1 to about 1:60; or from about 50:1 to about 1:50; or from about 40:1 to about 1:40; or from about 30:1 to about 1:30; or from about 20:1 to about 1:20; or from about 1:10 to about 10:1; or from about 9:1 to about 1:9; or from about 8:1 to about 1:8; or from about 7:1 to about 1:7; or from about 6:1 to about 1:6; or from about 5:1 to about 1:5; or from about 4:1 to about 1:4; or from about 3:1 to about 1:3, or from about 1:2 or about 2:1, including all values and subranges therein. In some embodiments, the ratio of fluorescent monomers to non-fluorescent monomers is about 1:5,000 to about 1:100, including all values and subranges therein. In other embodiments, the ratio is about 1:1.

In some embodiments, the heteropolymers comprise as a weight percent of the polymerizable near-IR dyes: about 1% to about 99%; or about 1% to about 95%; or about 1% to about 90%; or about 1% to about 80%; or about 1% to about 70%; or about 1% to about 60%; or about 1% to about 60%; or about 1% to about 50%; or about 1% to about 40%; or about 1% to about 30%; or about 1% to about 20%; or about 1% to about 10%; or about 10% to about 90%; or about 10% to about 80%; or about 10% to about 70%; or about 10% to about 60%; or about 10% to about 50%; or about 10% to about 40%; or about 10% to about 30%; or about 10% to about 20%; or about 20% to about 80%; or about 20% to about 70%; or about 20% to about 60%; or about 20% to about 50%; or about 20% to about 40%; or about 20% to about 30%; or about 30% to about 80%; or about 20% to about 70%; or about 20% to about 60%; or about 20% to about 50%; or about 20% to about 40%; or about 30% to about 70%; or about 30% to about 60%; or about 30% to about 50%; or about 30% to about 40%; or about 40% to about 60%; or about 40% to about 50%.

Table 1 shows the spectral properties of a polymerizable near-IR dye and the corresponding spectral properties of a polymer comprising a monomer of said near-IR dye for the various near-IR dyes according to the present disclosure. In some embodiments, a polymer comprising a monomer of a near-IR dye of this disclosure exhibit absorption maxima in the range between about 500 nm and about 1000 nm, between about 600 nm and about 1000 nm, between about 700 nm and about 1000 nm, between about 600 nm and about 900 nm, between about 646 nm and about 814 nm, between about 646 nm and about 690 nm, or between about 780 nm and about 814 nm. In some embodiments, the polymerizable near-IR dyes this disclosure exhibit emission maxima in the range between about 600 nm and about 1000 nm, about 600 nm and about 950 nm, about 650 nm and about 900 nm, about 668 nm and about 842 nm, about 668 nm and about 712 nm, or about 796 nm and about 842 nm. In particular embodiments, the polymers of the present disclosure have spectral properties substantially similar to those of the fluorescent monomers. For example, a fluorescent polymer with an emission maximum substantially similar to that of the free fluorescent monomer has an emission maximum that is within about 5 nm, within about 10 nm, within about 20 nm, within about 50 nm, or within about 60 nm of the emission maximum of the un-polymerized (e.g., free) fluorescent monomer. In other embodiments, the spectral properties of the fluorescent monomers of the dyes of the present disclosure do not substantially change upon incorporation into a fluorescent polymer under the polymerization conditions used to prepare polymers with ethylenic backbone, e.g., free radical polymerization. In particular embodiments, the spectral characteristics of a monomeric polymerizable near-IR dye of the present disclosure as measured in organic solutions, e.g., absorption maximum and emission maximum, can be used to predict the spectral characteristics of the corresponding fluorescent near-IR polymer that comprises residues of the monomeric polymerizable near-IR dye (as demonstrated in the Table 1).

TABLE 1

Spectral properties of polymerizable near-IR dyes and the polymers comprising the dyes as monomers.

| Dye structure | Compound # | Compound Ref | Solution solvent | abs/ nm | em/ nm | 50% HEMA Hydrogel solvent | abs/ nm | em/ nm |
| --- | --- | --- | --- | --- | --- | --- | --- | --- |
| (structure) | 8 | Cy5-1SA-L1 | PBS DMSO | 638 650 | 660 678 | PBS | 646 | 668 |
| (structure) | 12 | Cy5-4SA-L1 | PBS DMSO | 646 658 | 666 686 | PBS | 654 | 678 |

TABLE 1-continued
Spectral properties of polymerizable near-IR dyes and the polymers comprising the dyes as monomers.
| Dye structure | Compound # | Compound Ref | Solution solvent | abs/ nm | em/ nm | 50% HEMA Hydrogel solvent | abs/ nm | em/ nm |
|---|---|---|---|---|---|---|---|---|
| 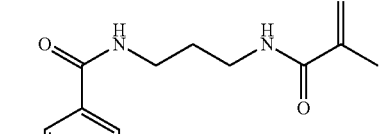 | 13 | Cy5-4SA-L2 | PBS DMSO | 648 658 | 668 684 | PBS | 654 | 682 |
| 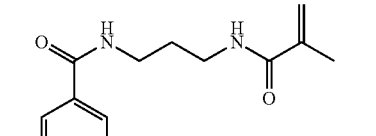 | 17 | Cy5.5-6SA-L1 | PBS | 676 | 700 | PBS | 680 | 706 |
| 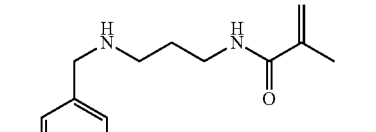 | 19 | Cy5.5-6SA-L2 | PBS | 676 | 696 | PBS | 682 | 706 |

TABLE 1-continued
Spectral properties of polymerizable near-IR dyes and the polymers comprising the dyes as monomers.
| Dye structure | Compound # | Compound Ref | Solution | | | 50% HEMA Hydrogel | | |
|---|---|---|---|---|---|---|---|---|
| | | | solvent | abs/nm | em/nm | solvent | abs/nm | em/nm |
| 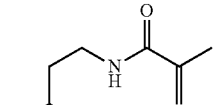 | 22 | Cy5.5-6SA-L3 | PBS | 684 | 706 | PBS | 690 | 712 |
| 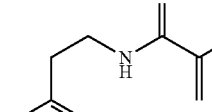 | 24 | Cy7-4SA-L1 | PBS | 772 | 796 | PBS | 780 | 802 |
| 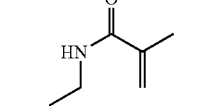 | 26 | Cy7.5-6SA-L1 | PBS | 816 | 848 | PBS | 808 | 832 |

TABLE 1-continued
Spectral properties of polymerizable near-IR dyes and the polymers comprising the dyes as monomers.
| Dye structure | Compound # | Compound Ref | Solution | | | 50% HEMA Hydrogel | | |
|---|---|---|---|---|---|---|---|---|
| | | | solvent | abs/nm | em/nm | solvent | abs/nm | em/nm |
| 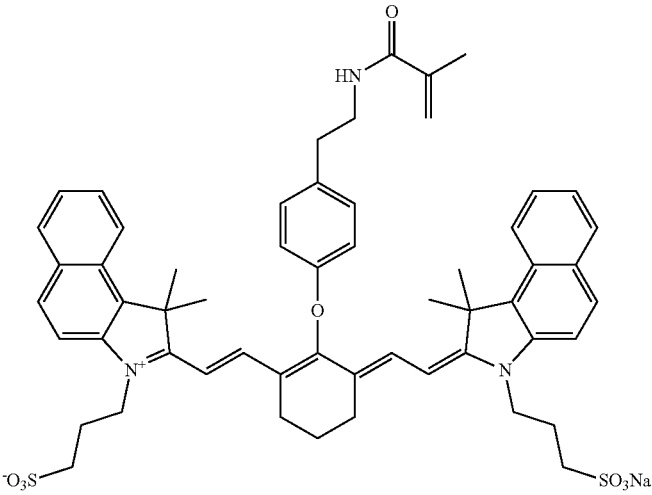 | 28 | Cy7.5-2SA-L1 | DMSO | 822 | 850 | PBS | 814 | 842 |
| 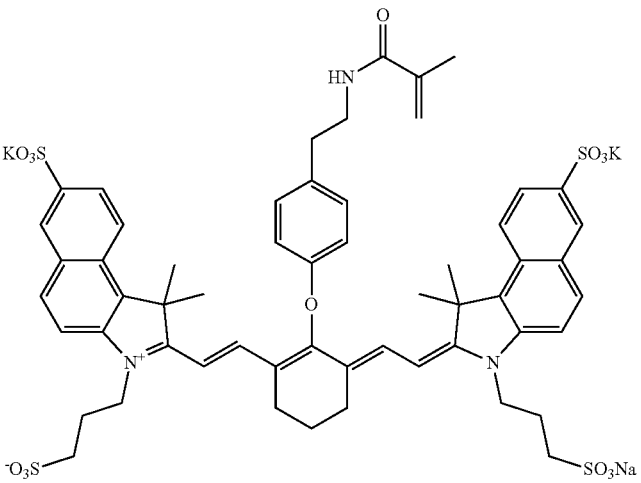 | 31 | Cy7.5-4SA-L1 | PBS | 802 | 830 | PBS | 814 | 842 |
| 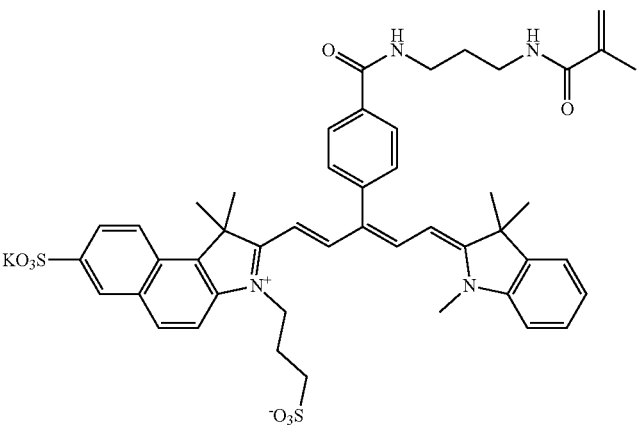 | 34 | Cy5.25-2SA-L1 | PBS | 656 | 680 | PBS | 666 | 688 |

TABLE 1-continued
Spectral properties of polymerizable near-IR dyes and the polymers comprising the dyes as monomers.
| Dye structure | Com-pound # | Com-pound Ref | Solution | | | 50% HEMA Hydrogel | | |
|---|---|---|---|---|---|---|---|---|
| | | | solvent | abs/ nm | em/ nm | solvent | abs/ nm | em/ nm |
| 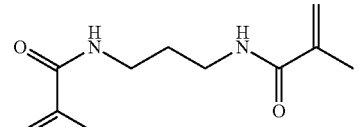 | 36 | Cy5.5-2SA-L1 | DMSO | 688 | 718 | PBS | 688 | 712 |
| 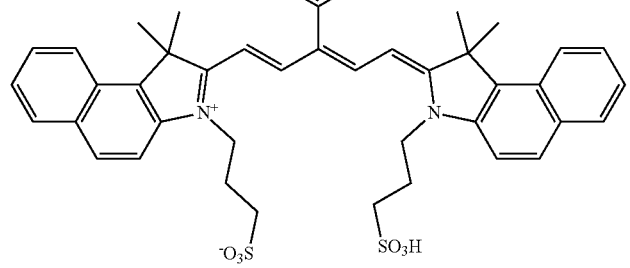 | 39 | Cy5-L1-BBA | DMSO | 647 | 680 | PBS | 654 | 688 |
| 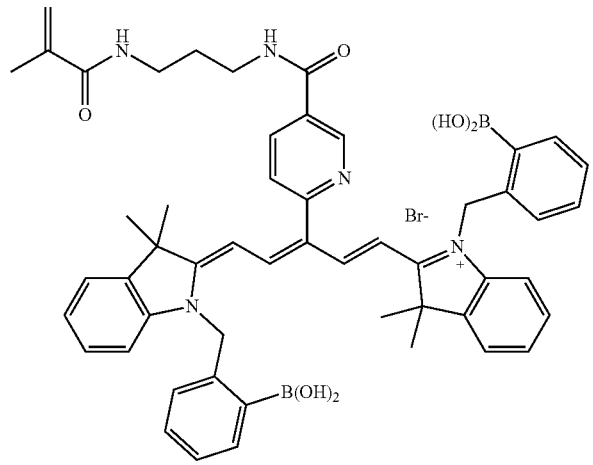 | 40 | Cy5-2SA-L1-BBA | DMSO | 659 | 690 | PBS | 661 | 692 |

TABLE 1-continued

Spectral properties of polymerizable near-IR dyes and the polymers comprising the dyes as monomers.

| Dye structure | Compound # | Compound Ref | Solution | | | 50% HEMA Hydrogel | | |
|---|---|---|---|---|---|---|---|---|
| | | | solvent | abs/ nm | em/ nm | solvent | abs/ nm | em/ nm |
| [structure] | 41 | Cy7-L1-BBA | DMSO | 785 | 818 | PBS | 775 | 806 |
| [structure] | 42 | Cy7-2SA-L1-BBA | DMSO | 794 | 830 | PBS | 780 | 816 |

Polymers described herein can be prepared in any suitable manner. Suitable synthetic methods used to produce the polymers provided herein include, by way of non-limiting example, cationic, anionic and free radical polymerization. In certain embodiments, polymer synthesis is performed neat or in any suitable solvent. Suitable solvents include, but are not limited to, pentane, hexane, dichloromethane, chloroform, water, ethylene glycol, propylene glycol, DMSO or dimethyl formamide (DMF). In certain embodiments, the polymer synthesis is performed at any suitable reaction temperature, including, e.g., from about −50° C. to about 100° C., or from about 0° C. to about 80° C. In particular embodiments, the polymer synthesis is performed at a reaction temperature of from about 5° C. to about 80° C.

In particular embodiments, the polymers are prepared by the means of a free radical polymerization. When a free radical polymerization process is used, (i) the monomer, (ii) optionally, the co-monomer(s), and (iii) an optional source of free radicals are provided to trigger a free radical polymerization process. In some embodiments, the source of free radicals is optional because some monomers may self-initiate polymerization upon heating at high temperature or irradiation. In certain instances, after forming the polymerization mixture, the mixture is subjected to polymerization conditions. Such conditions are optionally varied to any suitable level and include, by way of non-limiting example, temperature, pressure, light, atmosphere, ratios of starting components used in the polymerization mixture and reaction time. The polymerization is carried out in any suitable manner, including, e.g., in solution, dispersion, suspension, emulsion, or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a controlled (living) mode. In particular embodiments, controlled (living) polymerization processes include Reversible Addition-Fragmentation Chain Transfer (RAFT) polymerization processes and Atom Transfer Radical Polymerization (ATRP).

In certain embodiments, the polymer of the present disclosure is a hydrogel. A non-limiting example of a hydrogel is the hydrogel that can be prepared by reacting hydroxyethyl methacrylate (HEMA) to form poly (hydroxyethyl methacrylate), pHEMA. Furthermore, various comonomers can be used in combination to alter the hydrophilicity, mechanical and swelling properties of the hydrogel (e.g. PEG, NVP, MAA). Non-limiting examples of polymers include 2-hydroxyethyl methacrylate, polyacrylamide, N-vinylpyrrolidone, N,N-dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (of varying molecular weights), ethoxylated trimethylolpropane triacrylate, bisacrylamide and combinations thereof. Non-limiting examples of initiators include Irgacure Series (UV), Azobisisobutyronitrile (AIBN) (thermal), Ammonium Persulfate (APS) (thermal), and Ammonium persulfate/tetramethylethylenediamine (APS/TEMED) (redox).

In specific embodiments, the polymer is a fluorescent hydrogel prepared by copolymerization of HEMA and fluorescent dye Compound (I). In other embodiments, the hydrogels are prepared by copolymerization of various molar amounts of dye of formula (I), 2-hydroxyethyl methacrylate (HEMA) monomer, and tetraethylene glycol dimethacrylate (TEGDMA) crosslinker, in water with optional co-solvent, e.g., ethylene glycol, using 2,2'-Azobis[2-(2-imidazolin-2-yl)propane]dihydrochloride or other suitable polymerization initiator. In some embodiments, the hydrogels comprise 1 μM to 3 mM of the residues of the monomeric polymerizable near-IR dye. In other embodiments, the hydrogels comprise 1 μM to 1 mM of the residues of the monomeric polymerizable near-IR dye. In yet other embodiments, the hydrogels comprise 1 μM to 100 μM, 1 μM to 10 μm, or 1 μM to 5 μM of the residues of the monomeric polymerizable near-IR dye.

The polymers of the present disclosure may be degradable, either by the body (biodegradable) or by the application of an external initiator to start or speed up the degradation process (e.g. UV, ultrasonics, radio frequency, temperature, or other exogenous sources to initiate degradation.). In some instances, the polymer may be biodegradable or bioresorbable or may comprise any biodegradable or bioresorbable segments, including but not limited to degradable forms of alginates, poly(lactic acid), poly(vinyl alkohol), polyanhydrides, poly(glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328.

In certain embodiments, the fluorescent near-IR polymers provided herein have zwitterionic character, have ultra-low fouling in complex media, and are functionalizable, superhydrophilic, and biomimetic. Zwitterionic polymeric materials can be used to prevent the formation of a collagenous capsule when implanted, prolong the circulation time of nanoparticles used for drug/gene delivery and diagnostics, preserve protein bioactivity and cell viability, and enable long-lasting, nonfouling marine coatings.

In particular embodiments, the fluorescent near-IR polymers provided herein are biocompatible. In another embodiment of the disclosure, the polymers are biodegradable. Degradable hydrogels can be synthesized using Atom Transfer Radical Polymerization (ATRP) through co-polymerization of the HEMA with polymerizable fluorescent dyes of the present disclosure. Porous sensor scaffolds, based on non-degradable and degradable oxygen-sensing hydrogels, can be generated by using a sphere-templating fabrication technique. Degradable and non-degradable HEMA reagents and polymerizable dye will be polymerized over templating microspheres, which are subsequently dissolved away with solvent to generate desirable non-degradable and degradable scaffolds. Briefly, using controlled ATRP, HEMA will be polymerized in the presence of bi-functional degradable PCL-based ATRP initiator and cross-linker. In this synthesis scheme, pHEMA chains grow at the same rate from both sides of degradable initiator, resulting in degradation products with a MW that is half that of the parent polymer (as used herein, parent polymer refers to the polymer before degradation). By controlling the MW of the parent polymer and the PEG and PCL units in the initiator and/or cross-linker, the degradation rate of the polymers can be varied. For example, in some embodiments, limiting the MW of the parent polymer to about 10 kDa results in degradation products that can be cleared by the body while still preserving the parent polymer's mechanical strength. In some embodiments, limiting the MW of the parent polymer to about 10 kDa increases the degradation rate compared to polymers in which the MW of the parent polymer is greater than about 10 kDa.

In some embodiments, the degradation rate is about 12 months or less, about 6 months or less, or about 5 months or less, or about 4 months or less, or about 3 months or less, or about 2 months or less, or about 1 month or less. In particular embodiments, the degradation rate is less than about 1 month.

In certain embodiments the polymers provided herein are stimuli-responsive, e.g., temperature or pH-sensitive polymers. One non-limiting example of such a stimuli-responsive polymer is a temperature-sensitive polymer derived from co-polymerization of NIPAM. Such polymers are useful for implantation of the sensor comprising said polymers in a desired location within tissue by first dissolving the polymer in a suitable for injection media at a lower than body temperature and then injecting the resulting solution into the tissue and/or at desired location of the body. As the polymer is subjected to a higher (e.g., body) temperature, it precipitates in or near the site of the injection where monitoring of oxygen is required.

In some embodiments, the polymer of the present disclosure is incorporated into a sensor useful for detection of an analyte. The detection of the analyte can be in vitro or in vivo.

In one non-limiting example, the fluorescent near-IR polymer is incorporated into a sensor useful for monitoring pH, e.g., the pH of living tissues, cells, or cell compartments. "Cell compartment" typically is meant one or more of the cellular organelles suspended in the cell cytoplasm. The pH of a tissue, cell or cell compartment can be measured by introducing the polymerizable near-IR dye or the polymer of the present disclosure into said tissue, cell or cell compartment, irradiating the polymerizable near-IR dye or polymer with a suitable light source, and observing the intensity of fluorescence of the polymerizable near-IR dye or polymer. The observed fluorescence intensity can then be used to determine pH by a variety of methods known in the art. For instance, the observed fluorescence may be compared to a known standard, for example, a calibration curve of fluorescence intensity versus pH, or to fluorescence intensity measurements indicative of the total dye or complex present. Any conventional fluorimetric equipment can be used to irradiate the sample, and to measure the resulting fluorescent response.

The dyes and polymers of the present disclosure can provide more accurate determination of pH as compared to dyes known in the art because the $pK_a$s of the dyes and polymers of the present disclosure can, by design, be adjusted by substitution. Accuracy of pH measurement can be further increased by using a plurality of fluorescent dyes or polymers having different fluorescent responses. The intensity of fluorescence of each dye or polymer is then measured, and pH is determined by calculating the ratio.

In one embodiment, the polymerizable near-IR dyes that are copolymerized into the hydrogel are pH-sensitive, such as those dyes containing boronic acid moieties, and the fluorescence of the resulting hydrogel will change in response to the pH of the solution in which it resides. By monitoring the fluorescence intensity of the gel, with, for example, a fiber optic-based fluorimeter, a correlation between pH and fluorescence intensity can be determined.

In some embodiments, the polymers described herein are incorporated into a tissue-integrating scaffold to provide a tissue-integrating sensor (as described in the US patent application 2012/0265034, which is incorporated herein by reference). Preferably, the tissue-integrating scaffold of the disclosure is constructed with materials and/or micro-architecture such that the scaffold promotes tissue-integration and/or vascularization. For example, porous scaffolds provide tissue biomaterial anchoring and promote in-growth throughout the pores. The resulting "hallway" or "channel" pattern of tissue growth are healthy, space-filling masses that persist over time and promote host cell integration. Most or all of the pores of the biomaterials described herein are preferably interconnected (co-continuous). The co-continuous pore structure of the biomaterials promotes space-filling in-growth of cells in the implant, which in turn limits the foreign body response and leads to long-term (greater than one week and up to years) persistence of the implant's ability to act as a sensor. Alternative structures that provide tissue integrating scaffolds include fibers (e.g., 1 to 10 or more microns in diameter, such as 5, 6, 7, 8, 9, 10 or more microns), which may be arranged in non-random or random configuration. Tissue-integrating scaffolds (in any configuration) can also be formed by multiphoton polymerization techniques, such as those described by Kaehr et al. (2008) *Proc. Nat'l. Acad. Sci. USA* 105(26):8850-8854; Nielson et al. (2009) *Small* 1:120-125; Kasprzak, Doctoral Dissertation, Georgia Institute of Technology, May 2009, the disclosure of those is incorporated herein by reference.

The tissue-integrating scaffold of the disclosure may comprise any material, including but not limited to synthetic polymers, naturally-occurring substances, or mixtures thereof. Exemplary synthetic polymers include, but are not limited to polyethylene glycol (PEG), poly 2-hydroxyethyl methacrylate (HEMA), silicone rubber, polycaprolactone dimethylacrylate, polysulfone, (poly)methy methacrylate (PMMA), soluble Teflon-AF, (poly) ethyleneterephthalate (PET, Dacron), Nylon, polyvinyl alcohol, polyacrylamide, polyurethane, and mixtures thereof. Exemplary naturally-occurring materials include, but are not limited to, fibrous or globular proteins, complex carbohydrates, glycosaminoglycans, extracellular matrix, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, chitosan etc. Natural polymers may be used as the scaffold or as an additive.

In certain embodiments, the tissue-integrating scaffold comprises a hydrogel. Furthermore, various comonomers can be used in combination to alter the hydrophilicity, mechanical and swelling properties of the hydrogel (e.g. PEGMA, NVP, MAA). Non-limiting examples of monomers include 2-Hydroxyethyl methacrylate, acrylamide, N-vinylpyrrolidone, N,N-Dimethylacrylamide, poly(ethylene glycol) monomethacrylate (of varying molecular weights), diethylene glycol methacrylate, N-(2-hydroxypropyl)methacrylamide, glycerol monomethacrylate, 2,3-dihydroxypropyl methacrylate and combinations thereof. Non-limiting examples of cross-linkers include tetraethylene glycol dimethacrylate, poly(ethylene glycol) (n) diacrylate (of varying molecular weights), ethoxylated trimethylolpropane triacrylate, bisacrylamide and combinations thereof. Non-limiting examples of initiators include Bis(2,4,6-trimethylbenzoyl)-phenylphosphineoxide (UV), Azobisisobutyronitrile (AIBN) (thermal), Ammonium Persulfate (APS) (thermal).

The tissue-integrating scaffold may be a sphere-templated hydrogel, for instance an inverse colloid crystal, for example as described in U.S. Patent Publication No. 2008/0075752 to Ratner, et al. or other tissue integrating materials.

The scaffold may be degradable, either by the body (biodegradable) or by the application of an external initiator to start or speed up the degradation process (e.g. UV, ultrasonics, radio frequency, or other exogenous sources to initiate degradation.). For example, the tissue-integrating scaffold may be comprised of any biodegradable or bioresorbable polymers, including but not limited to degradable forms of alginates, poly(lactic acid), poly(vinyl alcohol), polyanhydrides, poly(glycolic acid), microporous polyesters, microporous polyethers and cross-linked collagen. One specific example is UV-photopolymerization of poly(ethylene glycol)-diacrylate and acrylated protease-degradable peptides and VEGF as described by Phelps, et al (2010) *Proc. Nat'l. Acad. Sci. USA* 107(8):3323-3328.

Other specific examples are polymers described by Kloxin et al (2009) *Science* 324:59-63 and U.S. Pat. No. 6,013,122 whose degradation is controlled through exposure to exogenous energy forms as well as Alexeev et al. (2003) *Anal. Chem.* 75:2316-2323; Badylak et al. (2008) *Seminars in Immunology* 20:109-116; Bridges et al. (2010) 94(1):252-258; Isenhath et al. (2007) *Research* 83A:915-922; Marshall et al. (2004) *Polymer Preprints, American Chemical Society, Division of Polymer Chemistry* 45:100-101; Phelps et al. (2010) *Proc Nat'l Acad Sci USA*. 107(8):3323-8; Ostendorf and Chichkov (2006) *Two Photon Polymerization: A New Approach to MicroMachining, Photonics Spectra*; Ozdemir et al. (2005) *Experimental and Clinical Research, Plast. Reconstr. Surg.* 115:183; U.S. Patent Publication No. 20080075752; Sanders et al. (2003) *Journal of Biomedical Materials Research* Part A 67A(4):1181-1187; Sanders et al. (2002) *Journal of Biomedical Materials Research* 62(2): 222-227; Sanders et al. (2003) *Journal of Biomedical Materials Research* 65(4):462-467; Sanders et al. (2005) *Biomaterials* 26:813-818; Sanders et al. (2005) *Journal of Biomedical Materials Research* Part A 72(3):335-342; Sanders (2003) *Journal of Biomedical Materials Research* 67(4): 1412-1416; Sanders et al. (2000) *Journal of Biomedical Materials Research* 52(1):231-237; and Young Min Ju et al. (2008) *J Biomed Mater Res* 87A: 136-146.

In certain embodiments, the tissue-integrating scaffold is constructed such that tissue response modifiers are released from the scaffold material to promote or enhance tissue-integration and vascularization.

In addition, the tissue-integrating scaffold may be constructed such that it has conduits, pores or pockets that are hollow or filled with degradable, angiogenic, or other substances (e.g. stem cells). As noted above, once in the body, the biodegradation of the material filling the conduits, pores or pockets, creates space for tissue, including capillaries to integrate with the material. The degradable material that initially fills the conduits, pores, or pockets may enhance vessel growth or tissue growth within the scaffold. This architecture promotes new vessel formation and maintains healthy viable tissue within and around the implant. In certain embodiments, the tissue-integrating scaffold is incorporated into a chemosensor and is constructed such that it is permeable to analytes of interest.

EXAMPLES

Example 1: Synthesis of a Polymerizable Near-IR Fluorescent Dye

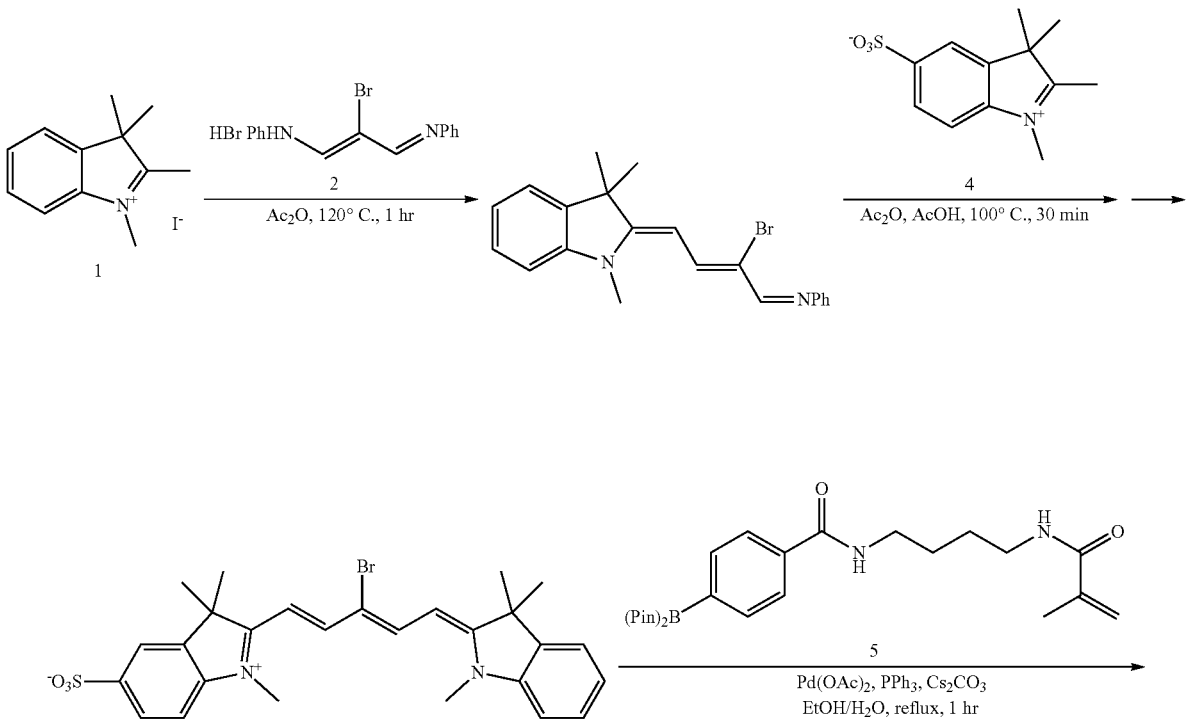

Scheme 1. Synthesis of Cy5-1SA-L1 (8)

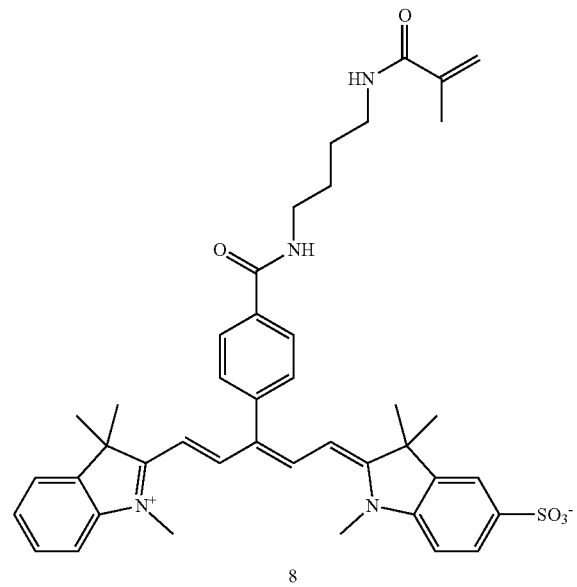

8

Compound 1 was synthesized according to literature procedure (Gu, Jiamin et al. *Bioorganic & Medicinal Chemistry Letters,* 22(24), 7667-7671; 2012). Compound 2 was prepared according to a literature procedure (Simonis, H. *Ber. Deut. Chem. Ges.* 1901, 34, 509; U.S. Pat. No. 6,747,159). Compound 4 was prepared according to literature procedure (Park, Jin Woo et al. *Bioconjugate Chemistry,* 23(3), 350-362; 2012.)

Preparation of N-(3-methacrylamidopropyl)-4-(4,4,5,5-tetramethyl-1,3,2-dioxaborolan-2-yl)benzamide (5)

In a 250 ml flask were combined 4-carboxy-phenylboronic acid pinacol ester (2 g, 8.06 mmol), 1-Ethyl-3-(3-dimethylaminopropyl)carbodiimide (EDC) (3.09 g, 16.12 mmol), hydroxybenzotriazole (HOBT) (2.19 g, 16.12 mmol), triethylamine (5.8 ml, 40.3 mmol) in 100 ml dichloromethane. The mixture was stirred for 15 minutes at RT, and then aminopropylmethacrylamide hydrochloride (1.73 g, 9.67 mmol) was added. The resulting clear solution was stirred at RT for 45 min, then transferred to a separatory funnel and extracted 3× with H2O, 1× with 0.1M HCl, and lastly, with brine. The organic portion was dried over $Mg_2SO_4$, and concentrated in vacuo to yield product 5 as an opaque solid (1.6 g, 52%).

Preparation of 2-((1E,3Z,5E)-3-bromo-5-(phenylimino)penta-1,3-dienyl)-1,3,3-trimethyl-3H-indolium-5-sulfonate (6)

Compounds 1 (500 mg, 1.66 mmol) and 2 (1.25 g, 3.32 mmol) were combined in 30 ml glacial AcOH in a 100 ml pressure bottle, and stirred at 120° C. under argon. After 1 hour the brown solution was concentrated in vacuo and purified via silica gel chromatography, eluting with 0 to 10% gradient of methanol/dichloromethane. Pure product fractions were combined and concentrated, yielding compound 6 as a gray residue (100 mg, 11%).

Preparation of 2-((1E,3Z,5E)-3-bromo-5-(1,3,3-trimethylindolin-2-ylidene)penta-1,3-dienyl)-1,3,3-trimethyl-3H-indolium-5-sulfonate (7)

Compounds 6 (100 mg, 0.196 mmol) and 4 (164 mg, 0.39 mmol) were combined in 10 ml of 1:10 mixture of pyridine/acetic anhydride and stirred at 100° C. under argon. After 30 minutes the dark blue solution was concentrated to dryness, and purified via silica gel chromatography, eluting with 0 to 15% methanol/dichloromethane gradient. Pure product fractions were combined and concentrated in vacuo to a dark blue residue (145 mg, quant).

Preparation of (E)-2-((2Z,4E)-3-(4-(3-methacrylamido propylcarbamoyl)phenyl)-5-(1,3,3-trimethyl-3H-indolium-2-yl)penta-2,4-dienylidene)-1,3,3-trimethylindoline-5-sulfonate (Cy5-1SA-L1) (8)

To a 100 ml 3-neck flask equipped with reflux condenser and stir bar was added 6 (145 mg, 0.269 mmol), 5 (200 mg, 0.54 mmol), and cesium carbonate (175 mg, 0.539), followed by 50 ml of 2:3 H2O/EtOH. The flask was heated to 100° C. with argon bubbling through the reaction mixture. After 15 minutes of argon purging, triphenylphospine (24 mg, 0.107 mmol) and palladium(II) acetate (12 mg, 0.053 mmol) were added to the reaction mixture. The dark blue solution was stirred at 100° C. with continuous argon bubbling. After 1 hour, reaction was concentrated dryness, and the residue was purified via silica gel chromatography (0 to 5% MeOH/DCM), to yield 135 mg of compound 8 as a dark blue residue (71%). LCMS (ESI+) m/z calcd for $C_{41}H_{47}N_4O_5S^+$, 707.3262 [M+1H], found 707.359 0 [M+1H]. Ex/Em (DMSO): $\lambda_{max}$ 650 nm, $\lambda_{em}$ 678 nm.

Scheme 2. Synthesis of Cy5-4SA-L1 (12) and Cy5-4SA-L2 (13)

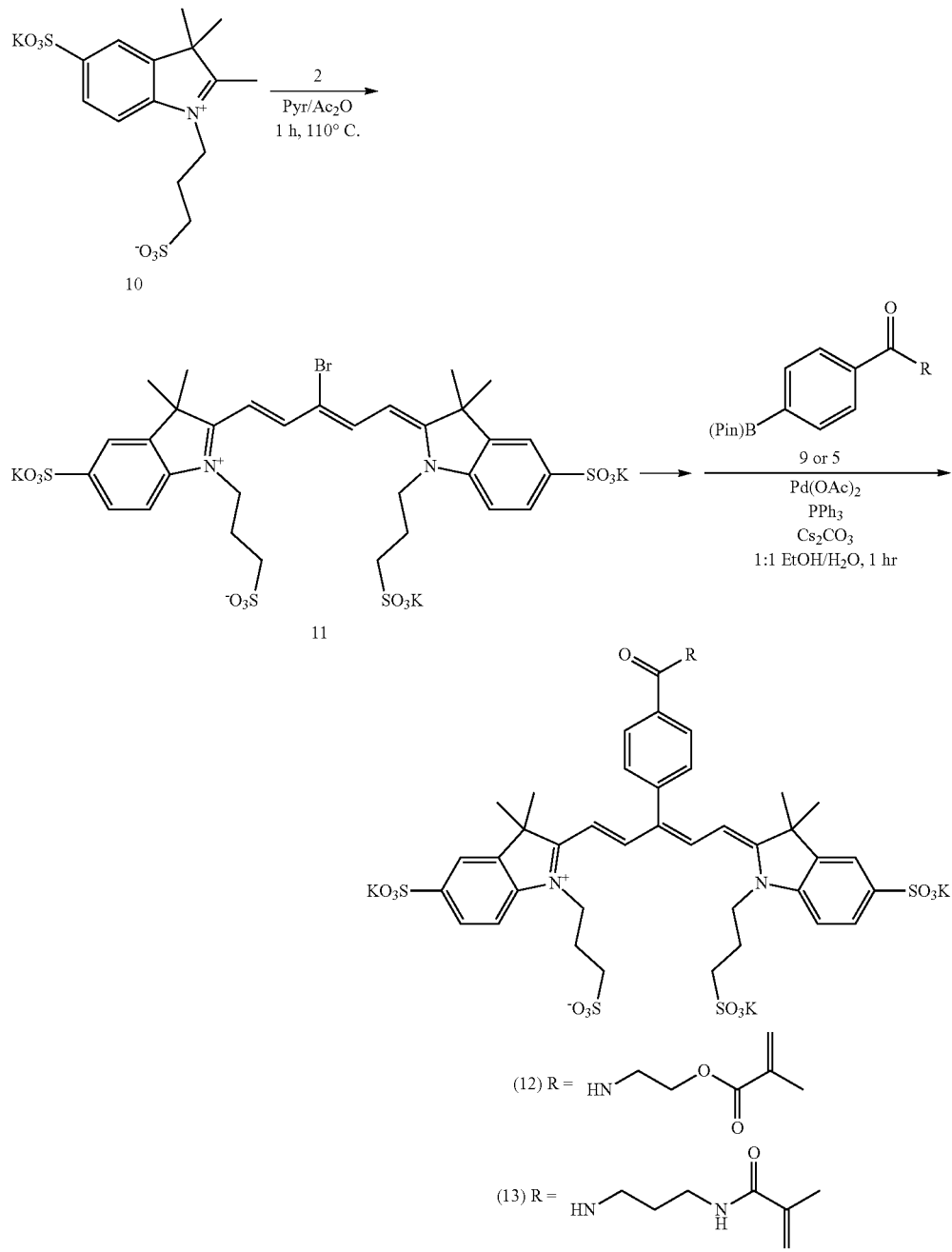

Preparation of 2-methacrylamidoethyl 4-(4,4,5,5-tetramethyl-1,3,2-dioxaborolan-2-yl)benzoate (9)

In a 250 ml flask were combined 4-carboxy-phenylboronic acid pinacol ester (4 g, 16.13 mmol), 1-Ethyl-3-(3-dimethylaminopropyl)carbodiimide (EDC) (6.2, 32.36 mmol), hydroxybenzotriazole (HOBT) (5.4 g, 32.36 mmol), and triethylamine (11.6, 80.06 mmol) in 100 ml dichloromethane. The mixture was stirred for 15 minutes at RT, and then 2-aminoethylacrylate hydrochloride (3.22 g, 19.35 mmol) was added. The resulting clear solution was stirred at RT for 45 min, then transferred to a separatory funnel and extracted 3× with H2O, 1× with 0.1M HCl, and lastly, with brine. The organic portion was dried over $Mg_2SO_4$, and concentrated in vacuo to yield product 9 as white solid (3.35 g, 58%).

Preparation of 2-((1E,3Z,5Z)-3-bromo-5-(3,3-dimethyl-5-sulfonato-1-(3-sulfonatopropyl)indolin-2-ylidene)penta-1,3-dienyl)-3,3-dimethyl-1-(3-sulfonatopropyl)-3H-indolium-5-sulfonate potassium salt (11)

Compound 10 was prepared according to literature procedure (Richard, Jean-Alexandre et al. Organic Letters, 10 (19), 4175-4178; 2008.

Compound 2 (278 mg, 0.68 mmol) and compound 10 (66 mg, 0.17 mmol) were combined in a 50 ml flask, to which was then added 20 ml of 1:10 Pyridine/acetic anhydride. The mixture was stirred at 100° C. under argon, and after 2 hours the dark blue mixture was diluted with 50 ml ether, and the resulting precipitate was collected by filtration. The solid was purified on reverse phase $C_{18}$ silica, eluting with 0 to 10% acetonitrile/water gradient to yield compound 11 as dark blue solid after concentration of product-containing fractions (100 mg, 61%).

Preparation of 2-((1E,3Z,5Z)-5-(3,3-dimethyl-5-sulfonato-1-(3-sulfonatopropyl)indolin-2-ylidene)-3-(4-(2-(methacryloyloxy)ethylcarbamoyl) phenyl) penta-1,3-dienyl)-3,3-dimethyl-1-(3-sulfonatopropyl)-3H-indolium-5-sulfonate potassium salt (Cy5-4SA-L1) (12)

Compound 11 (80 mg, 0.087 mmol), compound 9 (125 mg, 0.35 mmol), and cesium carbonate (20 mg, 0.061 mmol) were dissolved in 12 ml of 1:1 EtOH/H2O in a 50 ml flask. The mixture was heated to reflux with stirring with argon bubbling through the reaction mixture. After 15 minutes, palladium(II)acetate (2 mg, 0.009 mmol) and triphenylphosphine (8 mg, 0.035 mmol) were added the reaction mixture. Argon was continuously bubbled through the reaction solution, and after 3 hours the reaction solution was concentrated using rotary evaporation to remove ethanol. The remaining solution was purified on reverse phase C18 silica column eluting with 0-30% acetonitrile/water. Pure fractions were combined and concentrated to yield 12 as a dark blue solid (25 mg, 26%). %). $^1$H NMR (400 MHz, D2O) δ ppm 1.48 (s, 12H) 1.72 (s, 3H) 1.79 (m, 4H) 2.51 (t, J=7.2 Hz, 4H) 3.56 (t, J=5.6, 2H) 3.63 (t, J=7.6, 4H) 4.21 (t, J=5.6 Hz, 2H) 5.45 (d, J=14.0 Hz, 2H) 5.52 (t, J=1.5, 1H) 5.94 (t, J=1.0, 1H) 7.07 (d, J=8.2, 2H) 7.13 (d, J=8.2, 2H) 7.59 (dd, J=8.2 Hz, J=1.9 Hz, 2H) 7.66 (d, J=1.8 Hz, 2H) 7.72 (d, J=8.2 Hz, 2H) 8.02 (d, J=14.0, 2H). Ex/Em (DMSO): $\lambda_{max}$ 658 nm, $\lambda_{em}$ 686 nm Preparation of 2-((1E,3Z,5Z)-5-(3,3-dimethyl-5-sulfonato-1-(3-sulfonatopropyl)indolin-2-ylidene)-3-(4-(3-methacrylamidopropylcarbamoyl)phenyl) penta-1,3-dienyl)-3,3-dimethyl-1-(3-sulfonatopropyl)-3H-indolium-5-sulfonate potassium salt Cy5-4SA-L2 (13)

Compound 13 was synthesized analogously to compound 12, except compound 5 was used in place of 9. Blue solid was obtained (20 mg, 16%). LCMS (ESI+) m/z calcd for $C_{45}H_{55}N_4O_{14}S_4^+$: 1003.2592 [M+4H-3K], found 1003.5409 [M+4H-3K]. Ex/Em (DMSO): $\lambda_{max}$ 658 nm, $\lambda_{em}$ 684 nm.

Scheme 4. Synthesis of Cy5.5-6SA-L1 (17) and Cy5.5-6SA-L2 (19).

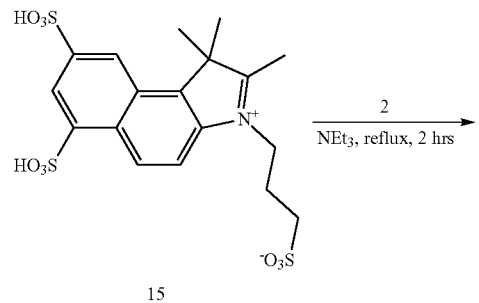

15

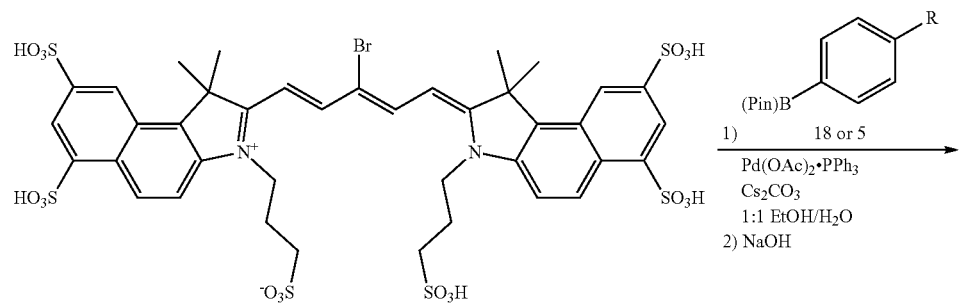

16

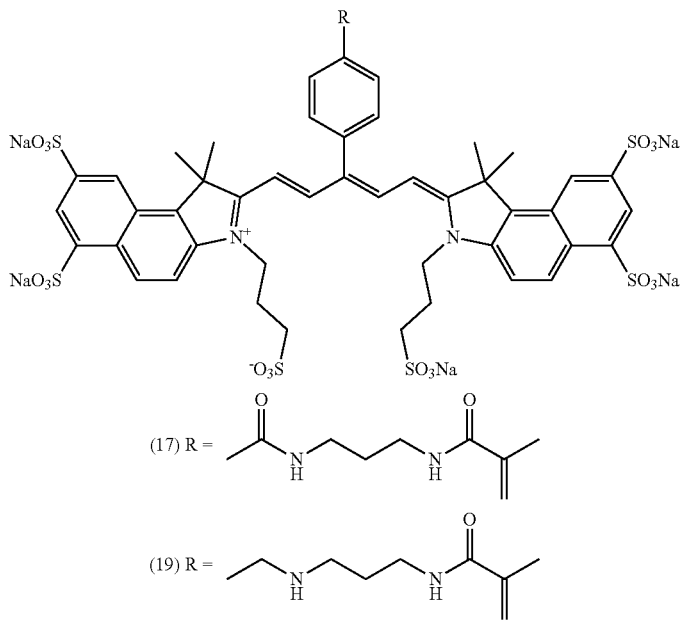

Preparation of 3-(2-((1E,3Z,5Z)-3-bromo-5-(1,1-dimethyl-6,8-disulfo-3-(3-sulfopropyl)-1H-benzo[e]indol-2(3H)-ylidene)penta-1,3-dienyl)-1,1-dimethyl-6,8-disulfo-1H-benzo[e]indolium-3-yl)propane-1-sulfonate potassium salt (16)

Compound 15 was prepared according to a literature procedure (Narayanan, Narasimhachari et al. PCT Int. Appl., 2007028037, 8 Mar. 2007) and obtained a red solid residue (2.09 g, 15%).

Compound 2 (4.7 g, 12.4 mmol) and compound 15 (12.1 g, 24.7 mmol) were combined in a 1000 ml flask, to which was then added 200 ml of triethylamine. The mixture was stirred at reflux under argon, and after 2 hours the solvent was decanted. The remaining dark blue solid was dissolved in H2O, and purified on reverse phase c18 silica, eluting with 0 to 10% acetonitrile/water gradient. The pure product fractions were combined and concentrated in vacuo, yielding compound 16 as a dark blue solid (2.09 g, 15%).

Preparation of 2-((1E,3Z,5Z)-5-(1,1-dimethyl-6,8-disulfonato-3-(3-sulfonatopropyl)-1H-benzo[e]indol-2(3H)-ylidene)-3-(4-(3-methacrylamidopropylcarbamoyl)phenyl)penta-1,3-dienyl)-1,1-dimethyl-3-(3-sulfonatopropyl)-1H-benzo[e]indolium-6,8-disulfonate sodium salt (Cy5.5-6SA-L1) (17)

Compound 16 (2.05 g 2.5 mmol), compound 5 (1.86 g, 5 mmol), and cesium carbonate (1.63 g, 5 mmol), were dissolved in 200 ml of 1:1 EtOH/H2O. The mixture heated to reflux with argon bubbling through the dark blue solution. After 15 min, palladium acetate (56 mg, 0.25 mmol) and triphenylphosphine (226 mg, 1 mmol) were added to, and the mixture reflux with argon bubbling for 2 hours. Reaction mixture concentrated to ~100 ml, and extracted 2× with DCM. To the aqueous portion was added sodium hydroxide (730 mg, 25 mmol) as a solution in 5 ml H2O, and stirred briefly. The aqueous portion was purified via reverse phase silica gel chromatography to yield product 17 as a dark blue solid (1.52 g, 44%). 1H NMR (400 MHz, DMSO-d6) δ ppm 1.68 (m, 2H) 1.80 (m, 2H) 1.82 (s, 3H) 2.12 (s, 12H) 2.38 (m, 4H) 2.59 (m, 2H) 3.09-3.24 (m, 4H) 3.81 (br. s., 2H) 3.87-4.10 (m, 4H) 5.26 (s, 1H) 5.56 (d, J=14.0 Hz, 2H) 5.66 (s, 1H) 7.20 (d, J=7.4 Hz, 2H) 7.53 (d, J=8.2 Hz, 2H) 7.73 (d, J=8.6 Hz, 2H) 8.09 (s, 2H) 8.08 (d, J=8.6, 2H) 8.54 (d, J=14.04 Hz, 2H) 8.87 (s, 2H). Ex/Em (DMSO): $\lambda_{max}$ 684 nm, $\lambda_{em}$ 712 nm.

Preparation of N-(3-(4-(4,4,5,5-tetramethyl-1,3,2-dioxaborolan-2-yl)benzylamino)propyl)methacrylamide (18)

In a 100 ml flask were combined 4-formyl-phenyl boronic acid pinacol ester (1 g, 4.3 mmol) and 3-aminopropylmethacrylamide hydrochloride (924 mg, 5.17 mmol) in 25 ml dichloromethane. Triethylamine (1.25 ml, 8.6 mmol) was added, and the mixture was stirred at 0° C. for 30 minutes. To the clear solution was then added sodium triacetoxyborohydride (1.8 g, 8.6 mmol), and the cloudy solution was stirred for 20 hrs under argon. The mixture was then transferred to a separatory funnel and extracted 3× with 0.05M HCl. Aqueous portions were combined and neutralized to pH ~8 with concentrated ammonia. The cloudy solution was extracted with dichloromethane (3×75 ml), organic portions combined, dried over Mg2SO4, and concentrated in vacuo to yield compound 18 as a clear oil (739 mg, 48%).

Preparation of 2-((1E,3Z,5Z)-5-(1,1-dimethyl-6,8-disulfonato-3-(3-sulfonatopropyl)-1H-benzo[e]indol-2(3H)-ylidene)-3-(4-((3-methacrylamidopropylamino)methyl)phenyl)penta-1,3-dienyl)-1,1-dimethyl-3-(3-sulfonatopropyl)-1H-benzo[e]indolium-6,8-disulfonate sodium salt (Cy5.5-6SA-L2) (19)

Compound 19 was prepared analogously to compound 17, except compound 18 was used instead of 5, to yield a dark blue solid (90 mg, 63%). $^1$H NMR (400 MHz, DMSO-d$_6$) δ ppm 1.73 (m, J=13.0, 6.58 Hz, 2H) 1.78-1.90 (m, 4H) 1.86 (s, 3H), 2.14 (s, 12H), 2.39 (t, J=7.2 Hz, 4H) 2.55 (m, 2H) 3.13-3.25 (m, 2H) 3.88-4.00 (m, 4H) 5.30 (t, J=1.37 Hz, 1H) 5.54 (d, J=14.0 Hz, 2H) 5.71 (s, 1H) 7.33 (d, J=8.2 Hz, 2H) 7.75 (d, J=9.0 Hz, 2H) 7.99 (d, J=8.2 Hz, 2H) 7.99 (d, J=8.2 Hz, 2H) 8.10 (s, 2H) 8.08 (d, J=16.1 Hz, 2H) 8.56 (d, J=14.0 Hz, 2H) 8.73 (t, J=5.7 Hz, 1H) 8.88 (d, J=1.9 Hz, 2H). LCMS (ESI+) m/z calcd for $C_{53}H_{59}N_4O_2OS_6^+$: 1263.2041 [M+6H-5Na], found 1263.2983 [M+6H-5Na]. Ex/Em (DMSO): $\lambda_{max}$ 684 nm, $\lambda_{em}$ 710 nm.

Scheme 6. Synthesis of Cy5.5-6SA-L3 (22).

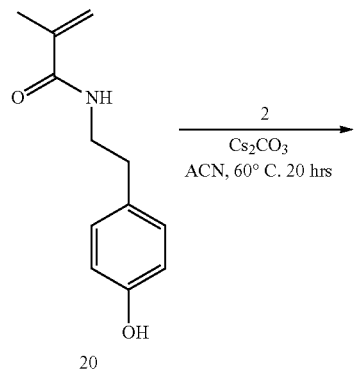

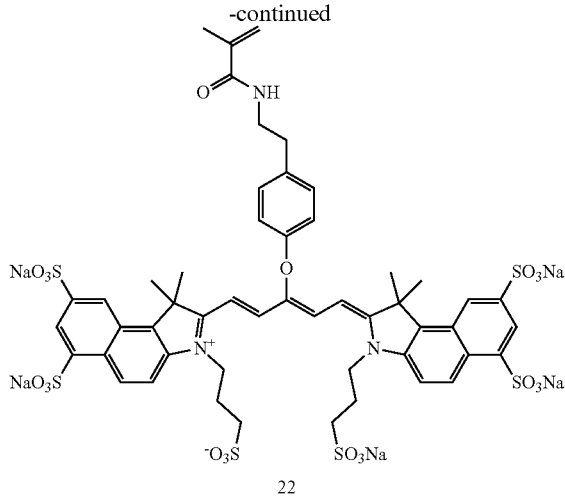

22

Preparation of N-(4-hydroxyphenethyl)methacrylamide (20)

Tyramine (10 g, 72.9 mmol) was suspended in 300 ml DCM in a 500 ml flask. The suspension was cooled to 0° C. via ice bath with stirring. Methacrylic anhydride (11.9 ml, 80.2 mmol) was added dropwise over the course of 15 minutes, and then the slightly cloudy mixture was stirred at room temperature for 1 hour, then placed into the freezer for several hours. The resulting precipitate was collected by filtration, washed with cold dichloromethane, and dried in high vacuum to yield compound 20 as a white powder (14 g, 93%).

Preparation of N-(4-((1Z)-1-(phenylamino)-3-(phenylimino)prop-1-en-2-yloxy)phenethyl)methacrylamide (21)

Compound 2 (1.42 g, 3.74 mmol), compound 20 (920 mg, 4.5 mmol), and cesium carbonate (1.82 g, 5.61 mmol) were suspended in 100 ml dry acetonitrile, and the mixture was stirred under argon at 50° C. After 18 hours, the mixture was filtered and concentrated in vacuo to yield orange oil. This crude product was purified using silica gel chromatography to yield compound 21 as an orange residue (950 mg, 60%).

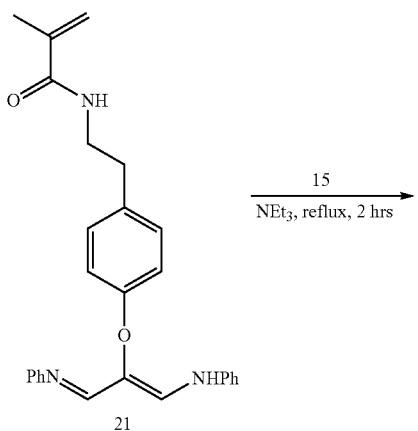

Preparation of 2-((1E,3Z,5Z)-5-(1,1-dimethyl-6,8-disulfonato-3-(3-sulfonatopropyl)-1H-benzo[e]indol-2(3H)-ylidene)-3-(4-(2-methacrylamidoethyl)phenoxy)penta-1,3-dienyl)-1,1-dimethyl-3-(3-sulfonatopropyl)-1H-benzo[e]indolium-6,8-disulfonate sodium salt (Cy5.5-6SA-L3) (22)

Compound 22 was prepared analogously to compound 16, except 21 was used in place of 2. Compound 22 was obtained as dark solid after purification (25 mg, 15%). $^1$H NMR (400 MHz, DMSO-d6) δ ppm 1.75 (s, 3H) 1.77 (m, 4H) 2.10 (s, 12H) 2.41 (t, J=6.6 Hz, 2H) 2.68 (t, J=6.6 Hz, 2H) 3.05 (m, 4H) 4.07-4.20 (m, 4H) 5.2 (s, 1H) 5.5 (s, 1H) 5.89 (d, J=14.8 Hz, 2H) 6.99 (d, J=7.8 Hz, 2H) 7.13 (d, J=7.8 Hz, 2H) 7.78 (d, J=9.0 Hz, 2H) 8.11 (s, 2H) 8.09 (d, J=9.0 Hz, 2H) 8.33 (d, J=14.8 Hz, 2H) 8.87 (s, 2H). Ex/Em (DMSO): $\lambda_{max}$ 690 nm, $\lambda_{em}$ 718 nm Scheme 7. Synthesis of Cy7-4SA-L1 (24).

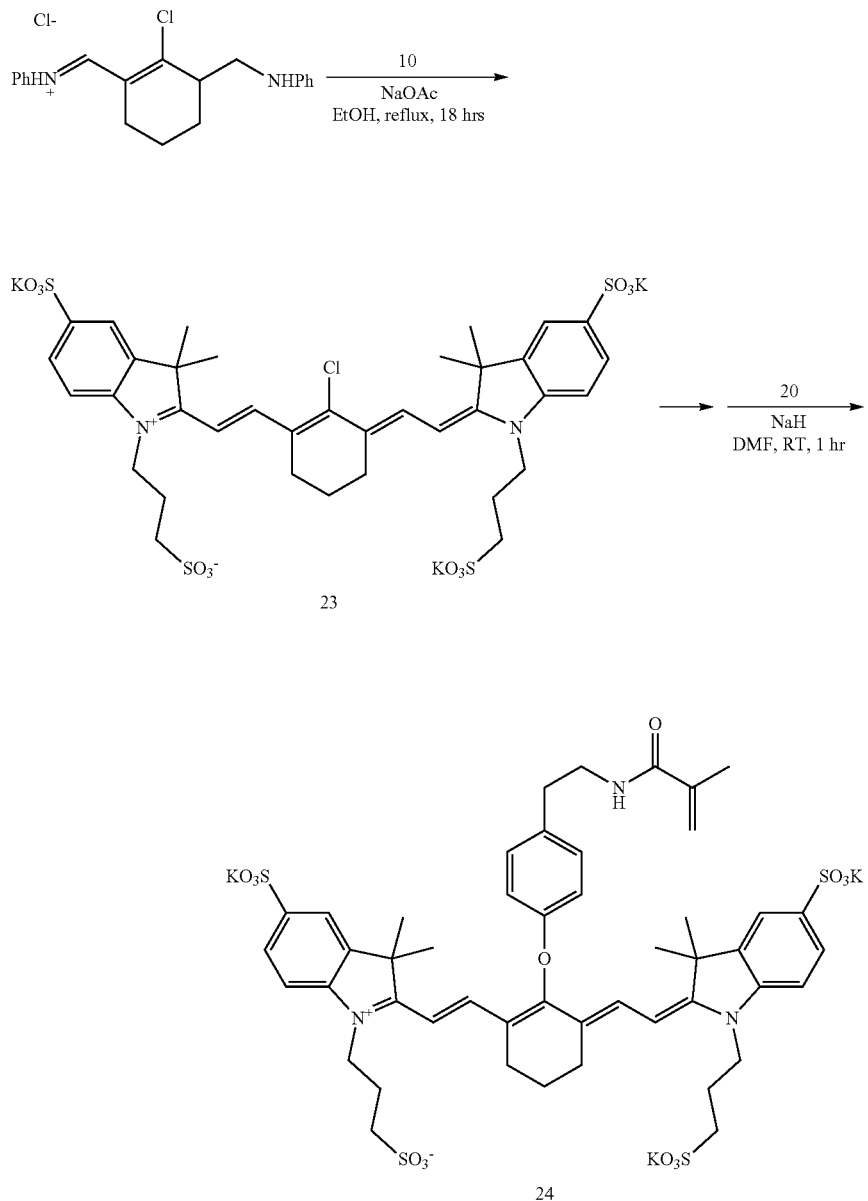

Preparation of 2-((E)-2-((E)-2-chloro-3-((E)-2-(3,3-dimethyl-5-sulfonato-1-(3-sulfonatopropyl)indolin-2-ylidene)ethylidene)cyclohex-1-enyl)vinyl)-3,3-dimethyl-1-(3-sulfonatopropyl)-3H-indolium-5-sulfonate potassium salt (24)

Compound 10 (921 mg, 2.31 mmol), N-(((E)-2-chloro-3-((phenylamino)methylene)cyclohex-1-enyl)methylene)benzenaminium monohydrochloride (414 mg, 1.15 mmol), and sodium acetate (208 mg, 2.54 mmol) were suspended in ethanol (25 ml) and stirred at reflux under argon. After 18 hrs solvent was removed in vacuo, and the green residue was purified via reverse phase silica gel chromatography, eluting with 0 to 10% acetonitrile/water. Pure product fractions were combined and concentrated to yield compound 23 as a dark green solid (358 mg, 33%).

Preparation of 2-((E)-2-((E)-3-((E)-2-(3,3-dimethyl-5-sulfonato-1-(3-sulfonatopropyl)indolin-2-ylidene)ethylidene)-2-(4-(2-methacrylamidoethyl)-phenoxy)cyclohex-1-enyl)vinyl)-3,3-dimethyl-1-(3-sulfonatopropyl)-3H-indolium-5-sulfonate potassium salt (Cy7-4SA-L1) (24)

To a dry 50 ml 3-neck flask containing sodium hydride (60% w/w in mineral oil) (80 mg, 2.0 mmol) and compound 20 (410 mg, 2.0 mmol) was added anhydrous dimethylformamide (1 ml), and the slurry was stirred for 10 minutes under argon. To the reaction was then added of 22 (100 mg, 0.1 mmol) as a solution in 1 ml anhydrous DMF, and the green mixture was stirred at room temperature for 1 hr. The mixture was diluted into 25 ml acetone, centrifuged, and the resulting green pellet was purified by reverse phase silica gel chromatography, eluting with 0 to 10% acetonitrile/water to yield compound 24 as a green solid (70 mg, 61%). $^1$H NMR (400 MHz, DMSO-d6) δ ppm 1.21 (s, 12H) 1.73 (s, 3H) 1.86 (m, 2H) 1.92 (t, J=7.0, 4H) 2.52 (t, J=6.6, 4H) 2.62-2.73 (m, 4H) 3.15-3.24 (m, 2H) 4.23 (t, J=7.4 Hz, 4H) 5.22 (t, J=1.6 Hz, 2H) 5.52 (s, 2H) 6.33 (d, J=14.0 Hz, 2H) 7.03 (d, J=8.6 Hz, 2H) 7.19 (d, J=8.6 Hz, 2H) 7.31 (d, J=8.2 Hz, 2H) 7.54 (d, J=8.2 Hz, 2H) 7.56 (s, 2H) 7.76 (d, J=14.0 Hz, 2H) 7.82 (t, J=5.7 Hz, 1H). Ex/Em (DMSO): $\lambda_{max}$ 792 nm, $\lambda_{em}$ 822 nm.

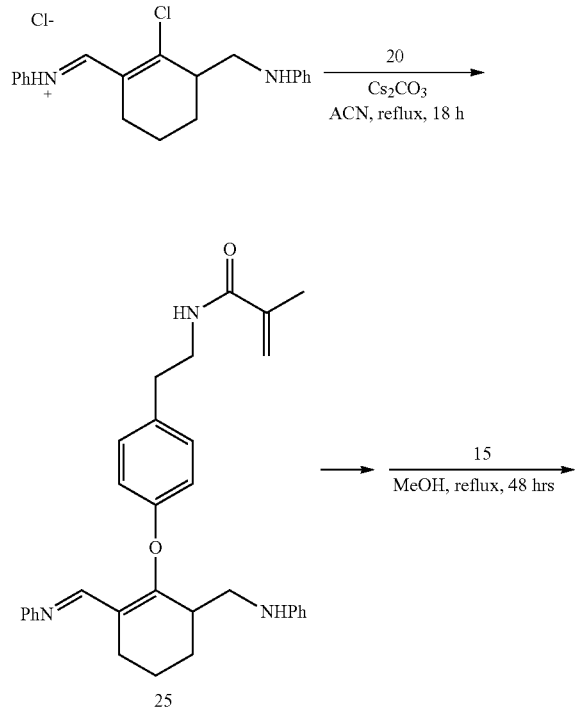

Scheme 8. Synthesis of Cy7.5-6SA-L1 (26).

Preparation of N-(4-(((6E)-6-((phenylamino)methylene)-2-((phenylimino)methyl)cyclohex-1-enyloxy)phenethyl)methacrylamide (25)

N-(((E)-2-chloro-3-((phenylamino)methylene)cyclohex-1-enyl)methylene)benzenaminium monohydrochloride (1 g, 2.8 mmol), cesium carbonate (3.2 g, 10 mmol), and compound 20 (850 mg, 4.2 mmol), were combined in 85 ml dry acetonitrile and heated to reflux under argon. After 18 hrs the mixture was filtered, the filtrate was evaporated to dryness. The orange-red residue was dissolved in 50 ml dichloromethane acidified with several drops of trifluoroacetic acid. The acidified solution was passed through a short silica gel column, eluting with 5% methanol/dichloromethane with 0.1% trifluoroacetic acid, followed by 5% methanol/dichloromethane with 1% triethylamine. Product fractions were combined and concentrated to yield crude compound 25 as a sticky red residue (2.17 g).

Preparation of 2-((E)-2-((E)-3-((E)-2-(1,1-dimethyl-6,8-disulfonato-3-(3-sulfonatopropyl)-1H-benzo[e]indol-2(3H)-ylidene)ethylidene)-2-(4-(2-methacrylamidoethyl)phenoxy)cyclohex-1-enyl)vinyl)-1,1-dimethyl-3-(3-sulfonatopropyl)-1H-benzo[e]indolium-6,8-disulfonate sodium salt (Cy7.5-6SA-L1) (26)

Compound 25 (276 mg, 0.625 mmol), compound 15 (1.1 g, 2.24 mmol), and sodium acetate (410 mg, 5 mmol) were dissolved in 50 ml methanol, and the mixture was heated to reflux under argon. After 72 hrs, reaction mixture was concentrated in vacuo, and the dark green residue was purified via reverse phase silica gel chromatography, eluting with 0 to 15% acetonitrile/water gradient. Pure fractions were combined and concentrated to yield compound 26 as a green residue (150 mg, 17%). $^1$H NMR (400 MHz, DMSO-d6) δ ppm 1.61 (s, 3H) 1.72 (s, 12H) 1.84 (m, 4H) 1.98 (m, 4H) 2.59-2.70 (m, 8H) 3.19 (t, J=7.0 Hz, 2H) 4.29 (m, 4H) 5.05 (s, 1H) 5.44 (s, 1H) 6.09 (d, J=14.0 Hz, 2H) 7.00 (d, J=8.6 Hz, 2H) 7.16 (d, J=8.6 Hz, 2H) 7.88 (d, J=14.0 Hz, 2H) 8.05 (d, J=9.0 Hz, 2H) 8.10 (d, J=1.9 Hz, 2H) 8.78 (d, J=1.6 Hz, 2H). Ex/Em (DMSO): $\lambda_{max}$ 800 nm, $\lambda_{em}$ 828 nm.

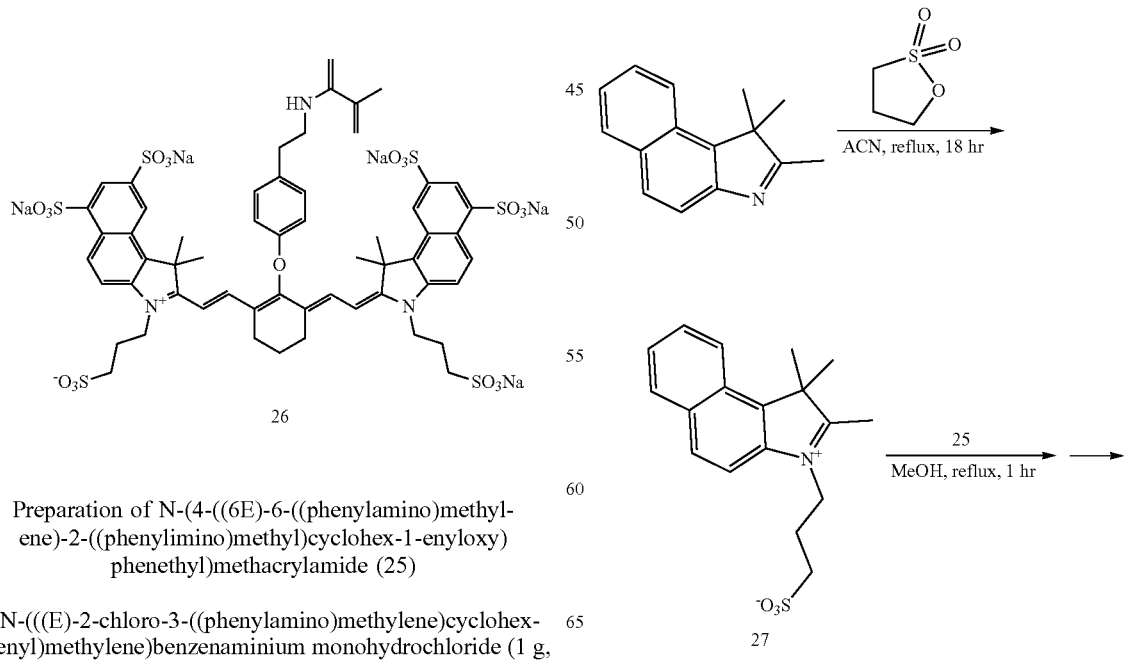

Scheme 9. Synthesis of Cy7.5-2SA-L1 (28).

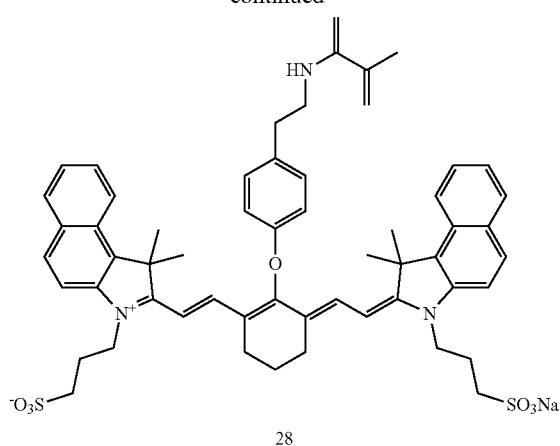

28

Preparation of 3-(1,1,2-trimethyl-1H-benzo[e]indolium-3-yl)propane-1-sulfonate (27)

Compound 27 was prepared analogously to compound 1, except compound 1,1,2-trimethyl-1H-benzo[e]indole was used as starting material. Compound 27 was obtained as a white powder (640 mg, 81%).

Preparation of sodium 3-(2-((E)-2-((E)-3-((E)-2-(1,1-dimethyl-3-(3-sulfonatopropyl)-1H-benzo[e]indol-2(3H)-ylidene)ethylidene)-2-(4-(2-methacrylamidoethyl)phenoxy)cyclohex-1-enyl)vinyl)-1,1-dimethyl-1H-benzo[e]indolium-3-yl)propane-1-sulfonate sodium salt (Cy7.5-2SA-L1) (28)

Compound 28 was prepared analogously to compound 26, except compound 27 was used in place of 15. Reverse phase purification eluted with 15 to 40% methanol/water gradient. Product 28 was obtained as a green solid (50 mg, 26%). $^1$H NMR (400 MHz, DMSO-d$_6$) δ ppm 1.55 (s, 12H) 1.66 (s, 3H) 1.92 (br. t, 2H) 1.96-2.05 (m, 4H) 2.56 (t, J=6.9 Hz, 2H) 2.68 (t, J=7.4 Hz, 2H) 2.75 (br. t, 4H) 3.21 (m, 4H) 4.39 (t, J=7.0 Hz, 4H) 5.11 (s, 1H) 5.49 (s, 1H) 6.38 (d, J=14.4 Hz, 2H) 7.13 (d, J=8.6 Hz, 2H) 7.26 (d, J=8.6 Hz, 2H) 7.43 (t, J=7.4 Hz, 2H) 7.56 (t, J=8.0 Hz, 2H) 7.76 (d, J=9.0 Hz, 2H) 7.84 (s, 2H) 7.93 (d, J=14.0 Hz, 2H) 7.96-8.02 (m, 2H) 8.10 (d, J=8.6 Hz, 2H). Ex/Em (DMSO): λ$_{max}$ 822 nm, λ$_{em}$ 850 nm.

Scheme 10. Synthesis of Cy7.5-4SA-L1 (31).

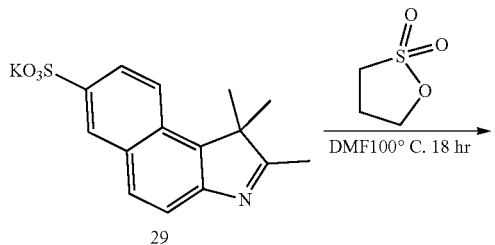

29

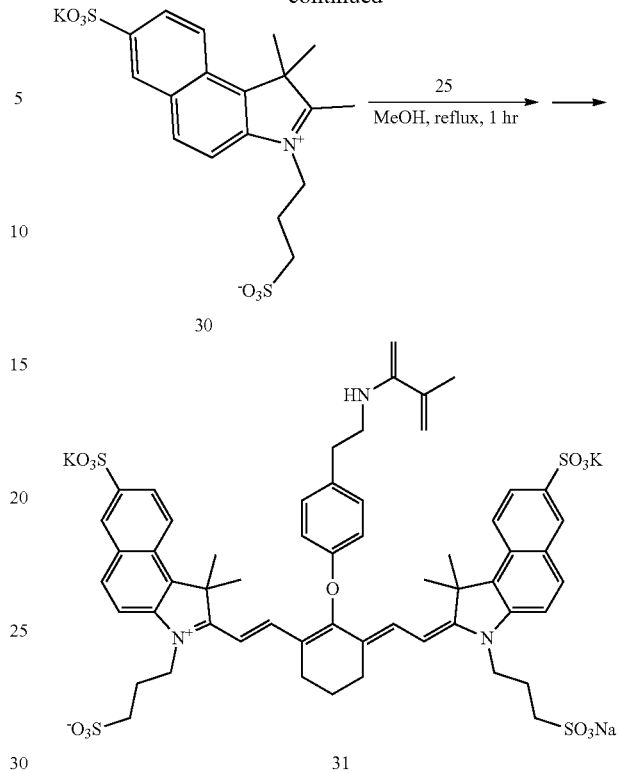

Preparation of 1,1,2-trimethyl-1H-benzo[e]indole-7-sulfonate potassium salt (29)

Compound 29 was prepared analogously to compound 14, except 6-amino-2-naphthalenesulfonic acid monohydrate is used in place of 7-amino-1,3-napthalenedisulfonic acid. Compound 29 in crude form was obtained as a tan solid (14.0 g, 95%) and used without further purification in the next step.

Preparation of 1,1,2-trimethyl-3-(3-sulfonatopropyl)-1H-benzo[e]indolium-7-sulfonate potassium salt (30)

A dry 1 liter flask containing crude 29 (14 g, 42 mmol) was filled with anhydrous DMF (300 ml) under argon. To the suspension was then added propanesultone (18 ml, 147 mmol) via syringe. The mixture was stirred at 100° C. under argon for 18 hrs, resulting in a dark purple solution. The mixture was diluted into acetone (500 ml) and the resulting precipitate isolated by filtration. The dark solid was washed with acetone (400 ml), dried in high vacuum, yielding a purple powder (15 g). This solid was dissolved in 50 ml H$_2$O and purified via reverse phase silica gel chromatography, eluting with water. Pure fractions combined and concentrated to yield compound 30 as an amber foam (3.1 g, 16%).

Preparation of 2-((E)-2-((E)-3-((E)-2-(1,1-dimethyl-7-sulfonato-3-(3-sulfonatopropyl)-1H-benzo[e]indol-2(3H)-ylidene)ethylidene)-2-(4-(2-methacrylamidoethyl)phenoxy)cyclohex-1-enyl)vinyl)-1,1-dimethyl-3-(3-sulfonatopropyl)-1H-benzo[e]indolium-7-sulfonate dipotassium sodium salt (Cy7.5-4SA-L1) (31)

Compound 31 was prepared analogously to compound 28, except compound 30 was used in place of 27. Product 31 was obtained as a green solid (50 mg, 10%). $^1$H NMR (400 MHz, DMSO-$d_6$) δ ppm 1.55 (s, 12H) 1.67 (s, 3H) 1.92 (m, 2H) 2.00 (m, 4H) 2.56 (t, J=6.63 Hz, 4H) 2.69 (t, J=6.6, 2H) 2.76 (m, 4H) 3.17-3.25 (m, 2H) 4.39 (br. t., 4H) 5.11 (d, J=1.6 Hz, 1H) 5.49 (s, 1H) 6.39 (d, J=14.4 Hz, 1H) 7.13 (d, J=8.2 Hz, 2H) 7.26 (d, J=8.2 Hz, 2H) 7.76 (d, J=9.0 Hz, 2H) 7.83 (t, J=5.5 Hz, 1H) 7.93 (d, J=14.4 Hz, 2H) 8.07 (d, J=9.0 Hz, 4H) 8.19 (s, 2H). Ex/Em (DMSO): $\lambda_{max}$ 826 nm, $\lambda_{em}$ 850 nm.

Preparation potassium 2-((1E,3Z)-3-bromo-4-(phenylamino)buta-1,3-dienyl)-1,1-dimethyl-3-(3-sulfonatopropyl)-1H-benzo[e]indolium-7-sulfonate (32)

Compound 30 (100 mg, 0.278 mmol) and compound 2 (217 mg, 0.557 mmol) were combined in 10 ml of 1:9 Pyridine/acetic anhydride. The mixture was stirred at 100° C. under argon, and after 2 hours the red mixture was

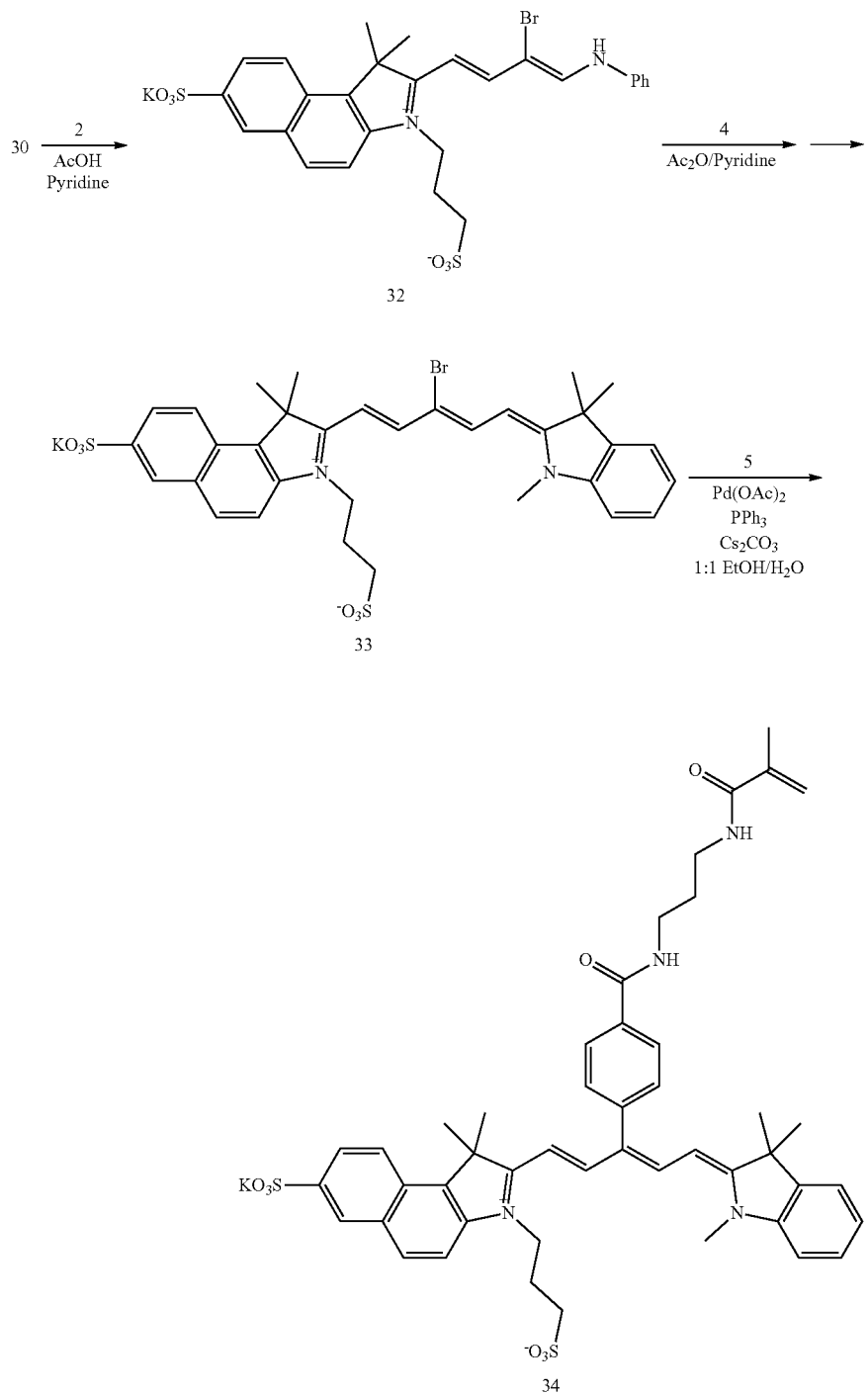

concentrated in vacuo. The solid residue was purified on normal phase silica, eluting with 10% to 90% methanol-dichloromethane gradient. The pure product fractions were combined and concentrated in vacuo, yielding a red residue (63 mg, 34%).

Preparation potassium 2-((1E,3Z,5Z)-3-bromo-5-(1,3,3-trimethylindolin-2-ylidene)penta-1,3-dienyl)-1,1-dimethyl-3-(3-sulfonatopropyl)-1H-benzo[e]indolium-7-sulfonate (33)

Compound 33 was prepared analogously to compound 7, except 32 was used in place of 6. Obtained was a blue solid residue (74 mg, quant.)

Preparation of potassium 2-((1E,3Z,5Z)-3-(4-(3-methacrylamidopropylcarbamoyl)phenyl)-5-(1,3,3-trimethylindolin-2-ylidene)penta-1,3-dienyl)-1,1-dimethyl-3-(3-sulfonatopropyl)-1H-benzo[e]indolium-7-sulfonate (Cy5.25-2SA-L1) (34)

Compound 34 was prepared analogously to compound 17, except 33 was used in place of 16. The product was obtained a blue solid residue (27 mg, 25%). LCMS (ESI+) m/z calcd for $C_{47}H_{53}N_4O_8S_2^+$: 865.3299 [M+2H−1K], found 865.5239 [M+2H-1K]. Ex/Em (DMSO): $\lambda_{max}$ 670 nm, $\lambda_{em}$ 702 nm.

Scheme 12. Synthesis of Cy5.25-2SA-L1 (36).

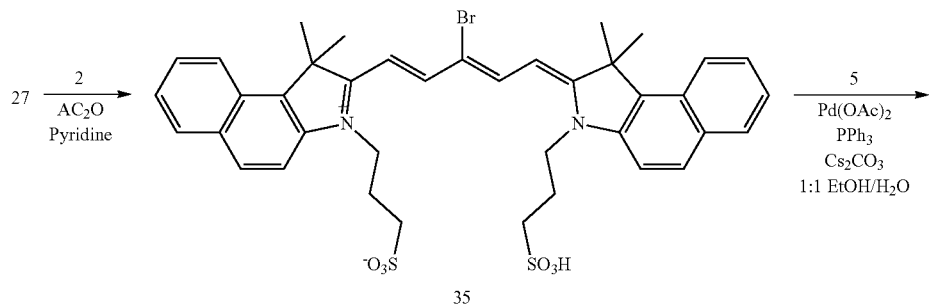

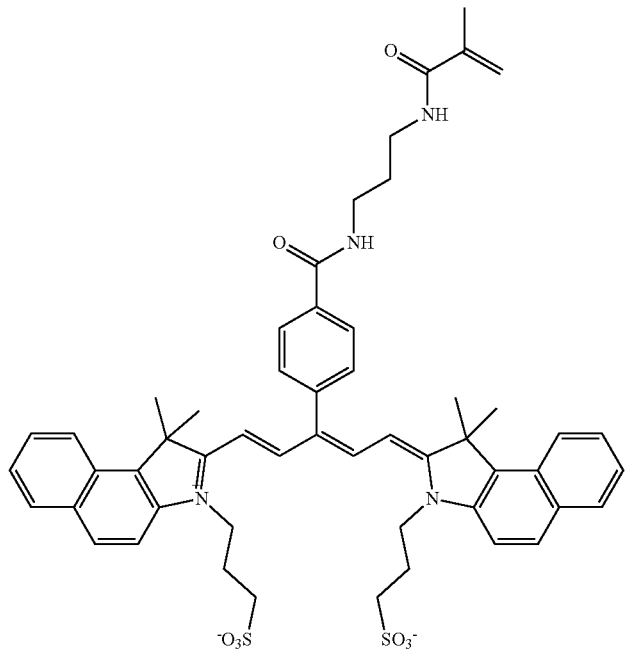

Preparation of 3-(2-((1E,3Z,5Z)-5-(1,1-dimethyl-3-(3-sulfonatopropyl)-1H-benzo[e]indol-2(3H)-ylidene)-3-(4-(3-methacrylamidopropylcarbamoyl)phenyl)penta-1,3-dienyl)-1,1-dimethyl-1H-benzo[e]indolium-3-yl)propane-1-sulfonate (36) (Cy5.5-2SA-L1)

Compound 36 was prepared analogously to compound 13, except compound 27 was used in place of 10, and 35 in place of 11. Obtained was 165 mg of blue solid (70%, 2-step yield). $^1$H NMR (400 MHz, DMSO-d$_6$) δ ppm 1.64-1.70 (m, 2H) 1.70-1.77 (m, 4H) 1.86 (s, J=0.78 Hz, 3H) 1.93 (br. s., 12H) 2.60 (t, J=7.0 Hz, 2H) 3.15 (t, J=5.0, 2H) 3.22 (m, 4H) 4.07 (m, 4H) 5.30 (s, 1H) 5.70 (s, 1H) 5.72 (d, J=14.3, 2H) 7.37 (d, J=7.8 Hz, 2H) 7.48 (t, J=7.4 Hz, 2H) 7.65 (t, J=7.6 Hz, 2H) 7.78 (d, J=9.0 Hz, 2H) 7.92 (d, J=7.6 Hz, 2H) 7.99-8.12 (m, 4H) 8.19 (d, J=8.6 Hz, 2H) 8.53 (t, J=5.5, 1H) 8.67 (d, J=14.3 Hz, 2H) 8.74 (t, J=5.6, 1H). Ex/Em (DMSO): $\lambda_{max}$ 688 nm, $\lambda_{em}$ 718 nm.

Scheme 14. Synthesis of Cy5-L1-BBA (39) and Cy5-2SA-L1-BBA (40).

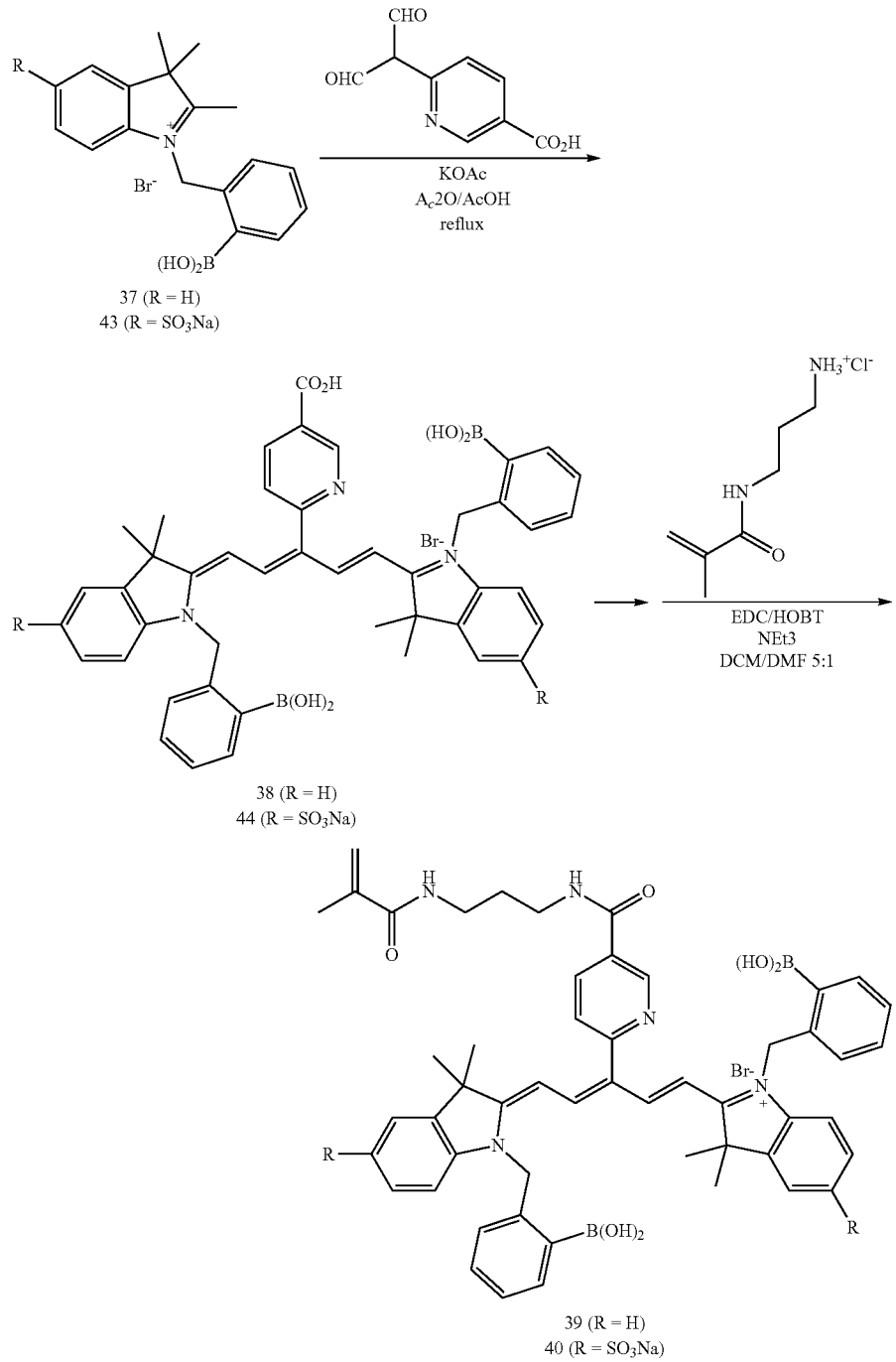

Compounds 37 and 43 were prepared according to literature procedure (Kukrer, B. and Akkaya, E. U., *Tet. Lett.*, 1999, 40, 9125-9128. LCMS (ESI+) m/z calculated for $C_{41}H_{47}N_4O_8S_2^+$: 787.2830 [M+2H-2K], found 787.5043 [M+2H-2K]. Ex/Em (DMSO): $\lambda_{max}$ 655 nm, $\lambda_{em}$ 687 nm.

Preparation 1-(2-boronobenzyl)-2-((1E,3Z,5Z)-5-(1-(2-boronobenzyl)-3,3-dimethylindolin-2-ylidene)-3-(5-carboxypyridin-2-yl)penta-1,3-dienyl)-3,3-dimethyl-3H-indolium bromide (38)

To a 50-mL round bottom flask equipped with magnetic stir bar and fitted with reflux condenser was added compound 37 (0.397 g, 1.06 mmol), 2-(3-Hydroxycarbonyl-6-pyridyl) malondialdehyde (0.100 g, 0.517 mmol), potassium acetate (0.254 g, 2.59 mmol) followed by 4 ml of 1:1 Ac$_2$O/AcOH. The reaction mixture was then heated to reflux at 130° C., and after 30 minutes concentrated to dryness in vacuo. The crude blue residue was purified by column chromatography (0-20% methanol/DCM gradient with 0.1% TFA) to yield 38 as a blue solid 38% yield (162 mg).

Preparation of 1-(2-boronobenzyl)-2-((1E,3Z,5Z)-5-(1-(2-boronobenzyl)-3,3-dimethylindolin-2-ylidene)-3-(5-(3-methacrylamidopropylcarbamoyl)pyridin-2-yl)penta-1,3-dienyl)-3,3-dimethyl-3H-indolium bromide (Cy5-L1-BBA) (39)

Compound 38 (87 mg, 0.105 mmol), N-(3-Dimethylaminopropyl)-N'-ethylcarbodiimide hydrochloride (EDC) (61 mg, 0.315 mmol), 1-Hydroxybenzotriazole hydrate (HOBT) (43 mg, 0.315 mmol), triethylamine (140 uL, 1.05 mmol) combined in 5 ml of dichloromethane with 1 ml DMF. After 30 minutes stirring at room temperature APMA (23 mg, 0.126 mmol was added. After 24 hrs the reaction mixture was diluted with DCM and water, extracted with DCM (2×50 mL). The DCM layer was washed with water (5×50 mL) followed by HCl (1 M, 25 mL) and brine (50 mL). Combined organic phases were dried over magnesium and then purified by column chromatography (0-10% methanol/DCM with 0.1% TFA). Compound 39 was obtained as a dark blue solid (54 mg, 59%). LCMS (ESI+) m/z calcd $C_{52}H_{56}B_2N_5O_6^+$: 868.4411 [M-Br], found 868.5292 [M-Br]. Ex/Em (DMSO): $\lambda_{max}$ 647 nm, $\lambda_{em}$ 680 nm.

Preparation of sodium 1-(2-boronobenzyl)-2-((1E, 3Z,5Z)-5-(1-(2-boronobenzyl)-3,3-dimethyl-5-sulfonatoindolin-2-ylidene)-3-(5-(3-methacrylamidopropylcarbamoyl)pyridin-2-yl)penta-1,3-dienyl)-3,3-dimethyl-3H-indolium-6-sulfonate bromide (40)

Compound 40 was prepared analogously to 39, except 3 was used in place of 2,3,3-trimethyl-3H-indole, and purification was conducted using reverse phase (Acetonitrile/water). The product was obtained a dark blue solid (52 mg, 84%). LCMS (ESI+) m/z calcd $C_{52}H_{56}B_2N_5O_{12}S_2^+$: 1028.3548 [M+2H-2K], found 1028.5675 [M+2H-2K]. Ex/Em (DMSO): $\lambda_{max}$ 659 nm, $\lambda_{em}$ 690 nm.

Scheme 15. Synthesis of Cy7-L1-BBA (41) and Cy7-2SA-L1-BBA (42).

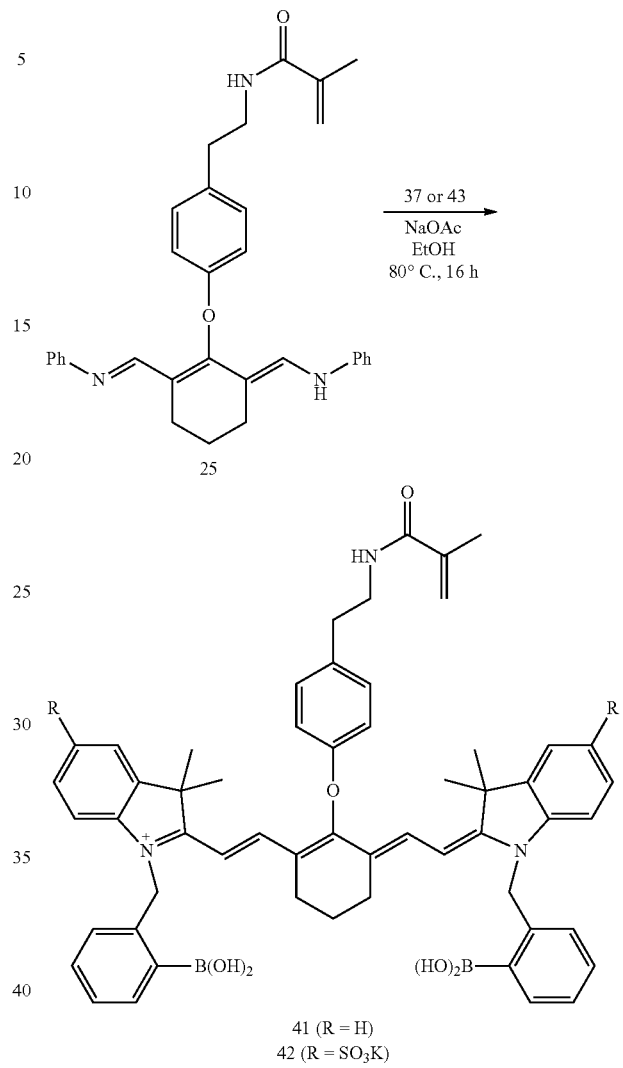

41 (R = H)
42 (R = SO$_3$K)

Preparation of 1-(2-boronobenzyl)-2-((E)-2-((E)-3-((E)-2-(1-(2-boronobenzyl)-3,3-dimethylindolin-2-ylidene)ethylidene)-2-(4-(2-methacrylamidoethyl)phenoxy)cyclohex-1-enyl)vinyl)-3,3-dimethyl-3H-indolium bromide (Cy7-L1-BBA) (41)

Compound 41 was prepared analogously to compound 28, except compound 37 was used in place of 27, and purification was conducted with MeOH/DCM+0.1% TFA as eluent. Obtained dark green solid (138 mg, 56%). LCMS (ESI+) m/z calcd $C_{56}H_{60}B_2N_3O_6^+$: 892.4663 [M-Br], found 892.4863 [M-Br]. Ex/Em (DMSO): $\lambda_{max}$ 785 nm, $\lambda_{em}$ 818 nm.

Preparation of sodium 1-(2-boronobenzyl)-2-((1E, 3Z,5Z)-5-(1-(2-boronobenzyl)-3,3-dimethyl-5-sulfonatoindolin-2-ylidene)-3-(5-(3-methacrylamidopropylcarbamoyl)pyridin-2-yl)penta-1,3-dienyl)-3,3-dimethyl-3H-indolium-6-sulfonate bromide (Cy7-2SA-L1-BBA) (42)

Compound 42 was prepared analogously to 41, except 3 was used in place of 2,3,3-trimethyl-3H-indole, and final purification was conducted using reverse phase (acetonitrile/water). The product was obtained as a dark green solid (50 mg, 60%). LCMS (ESI+) m/z calcd $C_{56}H_{60}B_2N_3O_{12}S_2^+$: 1052.3799 [M+2H-2K], found 1052.6185 [M+2H-2K]. Ex/Em (DMSO): $\lambda_{max}$ 794 nm, $\lambda_{em}$ 830 nm.

Synthesis of Hydrogels

HEMA (2-hydroxyethyl methacrylate) (50 Wt %), TEGDMA (triethyleneglycol-dimethacrylate) (1 Wt %1), ethylene glycol (20 Wt %), water (25.5 Wt %), 2,2'-Azobis[2-(2-imidazolin-2-yl)propane]dihydrochloride (1 Wt %) and acrylated dye (0.3 mM) were mixed together and purged with nitrogen for 1 minute. The solution was injected in between two glass plates separated by a 0.03" thick Teflon spacer. The filled plates were heated in a nitrogen purged oven for 3 hours. The resulting hydrogel was removed from the glass and stored in pH 7.4 PBS for spectral analysis.

Synthesis of Fluorescent Hydrogels

HEMA (2-hydroxyethyl methacrylate) (50 Wt %), TEGDMA (triethyleneglycol-dimethacrylate) (1 Wt %), ethylene glycol (20 Wt %), water (25.5 Wt %), 2,2'-Azobis[2-(2-imidazolin-2-yl)propane]dihydrochloride (1 Wt %) and acrylated dye (0.3 mM) were mixed together and purged with nitrogen for 1 minute. The solution was injected in between two glass plates separated by a 0.03" thick Teflon spacer. The filled plates were heated in a nitrogen purged oven at 45 C for 3 hours. The resulting hydrogel was removed from the glass and stored in pH 7.4 PBS for spectral analysis. 5 mm discs were cut out of the gel slab and placed into a 96-well plate containing 200 uL of PBS. Absorbance and emission scans were taken of gel discs to characterize spectra.

Synthesis of pH-Sensitive Hydrogel and its Use

N,N-Dimethyacrylamide (10 Wt %), N,N'-methylenebisacrylamide (0.2 Wt %), DMSO (10 Wt %), water (80 Wt %), 2,2'-Azobis[2-(2-imidazolin-2-yl)propane]dihydrochloride (0.5 Wt %) and Cy5-2SA-L1-BBA (compound 40, 3 mM) were mixed together and purged with nitrogen for 1 minute. The solution was injected in between two glass plates separated by a 0.03" thick Teflon spacer. The filled plates were heated in a nitrogen purged oven at 45 C for 3 hours. The resulting hydrogel was removed from the glass and stored in pH 7.4 PBS.

5 mm Discs were cut out of the gel slab and placed into a custom-made flow-cell. Phosphate buffers at different pH levels were pumped through the cell while the fluorescence of the gel was monitored using a custom-built spectrofluorimeter which provided excitation light at 630 nm, and collected the gel's emission at 650 nm. If the acrylated dyes co-polymerized into the hydrogel are pH-sensitive, such as those containing boronic acid moieties, the fluorescence of the resulting hydrogel will change in response to the pH of the solution in which it resides. By monitoring the fluorescence intensity of the gel, with, for example, a fiber optic-based fluorimeter, a correlation between pH and fluorescence intensity can be determined.

Figure 3:
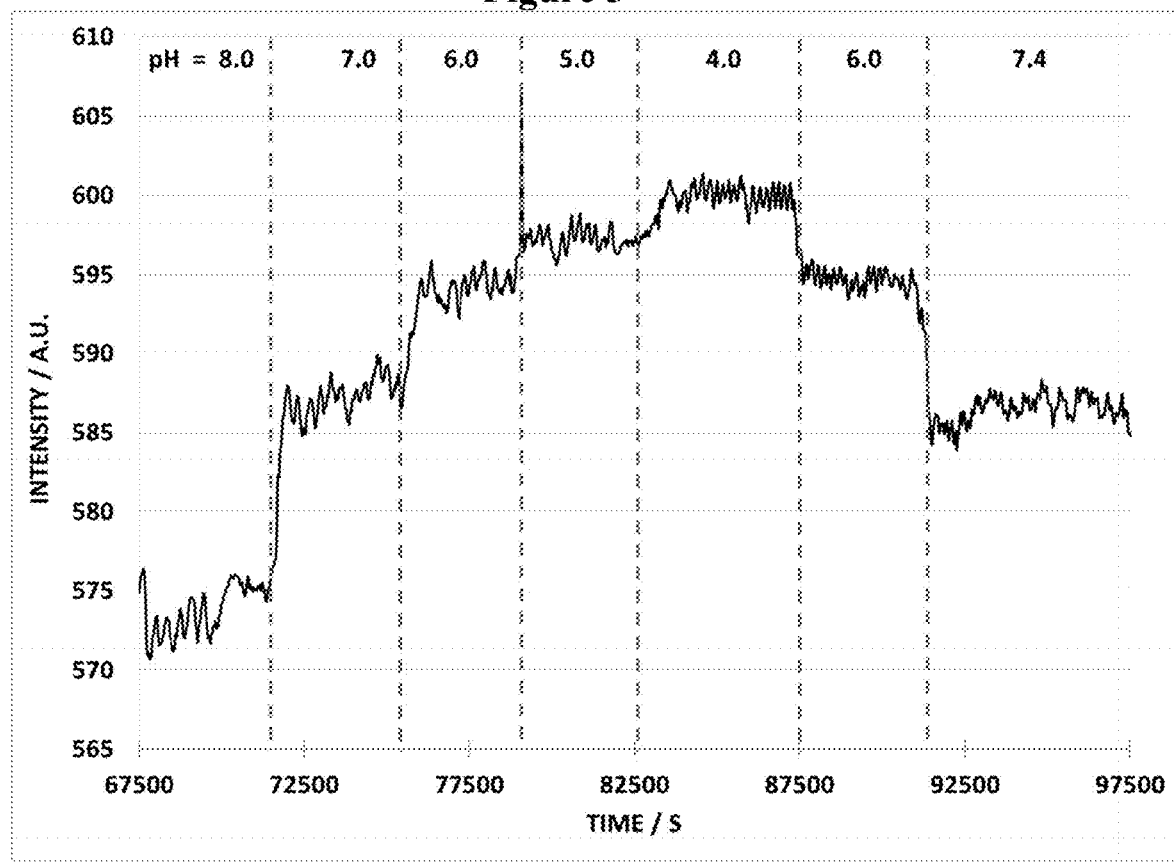
FIG. 3 depicts pH Sensitivity of hydrogel containing boronic acid-functionalized dye (compound 40; Cy5-2SA-L1-BBA).

The intensity of the hydrogel emission at 650 nm changed in response to the following pH levels: 8.0, 7.4, 7.0, 6.0, 5.0, 4.0. The response profile is shown in FIG. 3.
Absorbance/Emission Spectra of a Polymerizable Near-IR Dye Compared to a Hydrogel Cy5.5-2SA-L1 (Compound 36), is insoluble in aqueous media. To utilize this dye in an aqueous system, the near-IR dye was co-polymerized with pHEMA as described above to form a hydrophilic hydrogel, which is then swollen in water or PBS.

The maximum absorbance (nm) and emission (nm) for Cy5.5-2SA-L1 (Compound 36) and for the hydrogel were measured. Cy5.5-2SA-L1 (Compound 36) has an absorbance of 688 nm and emission of 718 nm in DMSO. See FIG. 1. The hydrogel comprising Cy5.5-2SA-L1 (Compound 36) and pHEMA has an absorbance of 688 nm and emission of 712 nm in PBS.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A polymerizable near-IR dye having a structure according to formula (I):

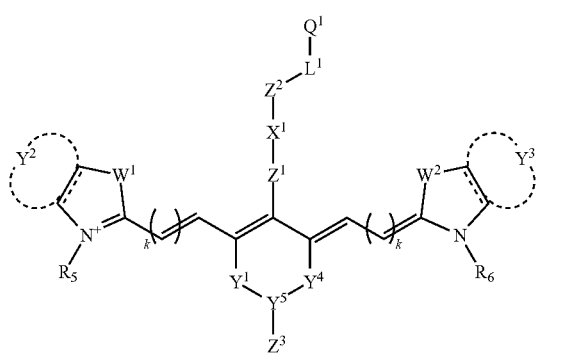

(I)

or a tautomer, salt, hydrate, or solvate thereof,
wherein:
 $Z^1$ is absent, O, $NR^{Z1}$, or S;
 $R^{Z1}$ is H, optionally substituted $C_1$-$C_{10}$ alkyl, or optionally substituted $C_2$-$C_{10}$ heteroalkyl;
 $X^1$ is absent, optionally substituted $C_6$-$C_{10}$ arylene, or optionally substituted $C_1$-$C_{10}$ heteroarylene;
 $Z^2$ is absent, $NR^{X1}$, O, S, $NR^{X2}C(O)$, $OC(O)$, $SC(O)$, $C(O)O$, $C(O)NR^{X3}$, $C(S)O$, or $C(O)S$;
 $Z^3$ is absent or H;

$R^{X1}$, $R^{X2}$, and $R^{X3}$ are each independently H, optionally substituted $C_1$-$C_{10}$ alkyl, or optionally substituted $C_1$-$C_{10}$ heteroalkyl;

$L^1$ is absent, optionally substituted $C_1$-$C_{30}$ alkylene, or optionally substituted $C_1$-$C_{30}$ heteroalkylene;

$Q^1$ is $NR^{Z3}C(O)C(R^{Q1})CH_2$, $OC(O)C(R^{Q1})CH_2$, or $SC(O)C(R^{Q1})CH_2$;

$R^{Z3}$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

$R^{Q1}$ is H, Me, Et, or n-Pr;

each of $Y^1$ and $Y^4$, independently, is absent or optionally substituted $C_1$-$C_4$ alkylene or optionally substituted $C_2$-$C_4$ heteroalkylene;

each of $Y^2$ and $Y^3$, independently, is absent or, together with the carbon atoms to which each is attached, form optionally substituted $C_6$-$C_{10}$ aryl or optionally substituted $C_2$-$C_{10}$ heteroaryl;

$Y^5$ is absent or N or $CR^7$;

$R^7$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

each of $W^1$ and $W^2$, independently, is $NR^2$, S, O, Se, or $CR^3R^4$;

$R^2$, $R^3$, and $R^4$ are independently H, optionally substituted $C_1$-$C_{30}$ alkyl, optionally substituted $C_1$-$C_{30}$ heteroalkyl, or $-L^2$-$Q^2$;

$L^2$ is optionally substituted $C_1$-$C_{30}$ alkylene or optionally substituted $C_1$-$C_{30}$ heteroalkylene;

$Q^2$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$;

each of $R^5$ and $R^6$, independently, is $-L^3$-$Q^3$, optionally substituted $C_1$-$C_{30}$ alkyl, or optionally substituted $C_6$-$C_{10}$ aryl;

$L^3$ is optionally substituted $C_1$-$C_{30}$ alkylene or optionally substituted $C_1$-$C_{30}$ heteroalkylene;

$Q^3$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$; and each k is independently 0 or 1.

2. The polymerizable near-IR dye of claim 1 wherein $Z^1$ is O.

3. The polymerizable near-IR dye of claim 1, wherein the polymerizable near-IR dye has a structure according to formula (IA):

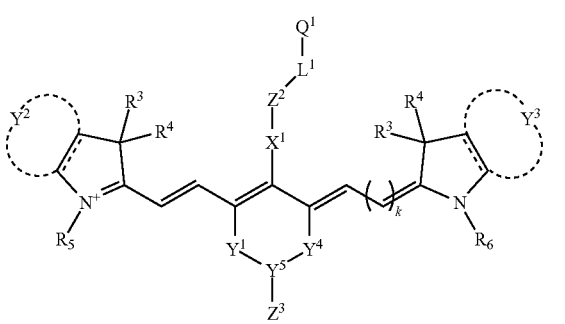

(IA)

or a tautomer, salt, hydrate, or solvate thereof,
wherein
each $R^3$ is H, optionally substituted $C_1$-$C_{30}$ alkyl, or optionally substituted $C_1$-$C_{30}$ heteroalkyl; and each $R^4$ is H, optionally substituted $C_1$-$C_{30}$ alkyl, or optionally substituted $C_1$-$C_{30}$ heteroalkyl.

4. The polymerizable near-IR dye of claim 3, wherein each $R^3$ and $R^4$ is, independently, $C_1$-$C_5$ alkyl optionally substituted with $SO_3H$ or $B(OH)_2$.

5. The polymerizable near-IR dye of claim 1, wherein the polymerizable near-IR dye has a structure according to formula (IB):

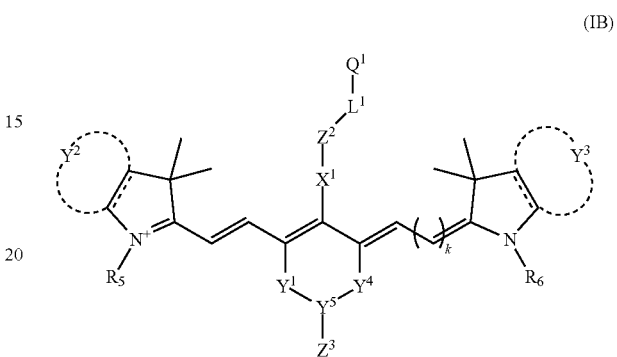

(IB)

or a tautomer, salt, hydrate, or solvate thereof,
wherein
$Y^2$, together with the carbon atoms to which it is attached, form optionally substituted $C_6$-$C_{10}$ arylene or optionally substituted $C_2$-$C_{10}$ heteroarylene; and $Y^3$, together with the carbon atoms to which it is attached, form optionally substituted $C_6$-$C_{10}$ arylene or optionally substituted $C_2$-$C_{10}$ heteroarylene.

6. The polymerizable near-IR dye of claim 1, wherein the polymerizable near-IR dye has a structure according to formula (IC):

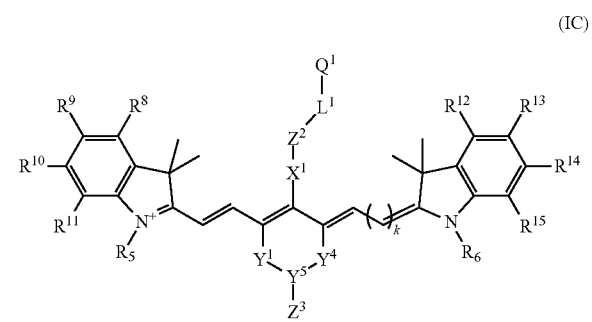

(IC)

or a tautomer, salt, hydrate, or solvate thereof,
wherein each of $R^8$-$R^{15}$ is, independently, H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, hydroxy; or, any two $R^8$-$R^{15}$ in the ortho position to each other, together with the carbon atoms to which each is attached, form an optionally substituted phenyl ring.

7. The polymerizable near-IR dye of claim 6, wherein the polymerizable near-IR dye has a structure according to formula (ID):

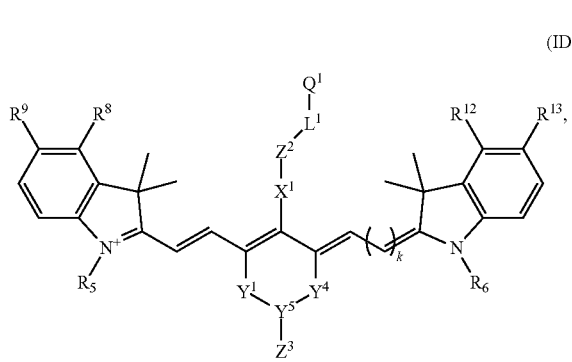

or a tautomer, salt, hydrate, or solvate thereof.

8. The polymerizable near-IR dye of claim 6, wherein the polymerizable near-IR dye has a structure according to formula (IE):

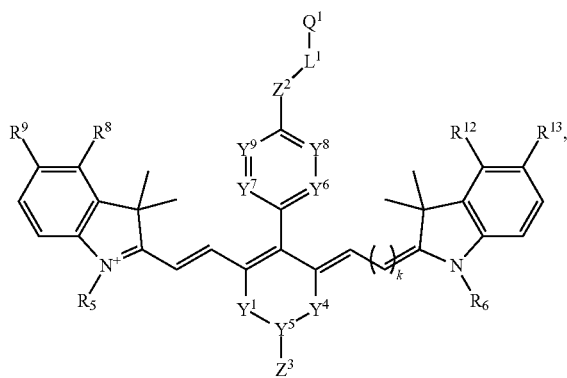

or a tautomer, salt, hydrate, or solvate thereof,
wherein:
  each of $Y^6$, $Y^7$, $Y^8$, and $Y^9$, is, independently, N or $CR^{16}$; and
  $R^{16}$ is H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, or hydroxy.

9. The polymerizable near-IR dye of claim 6, wherein the polymerizable near-IR dye has a structure according to formula (IF):

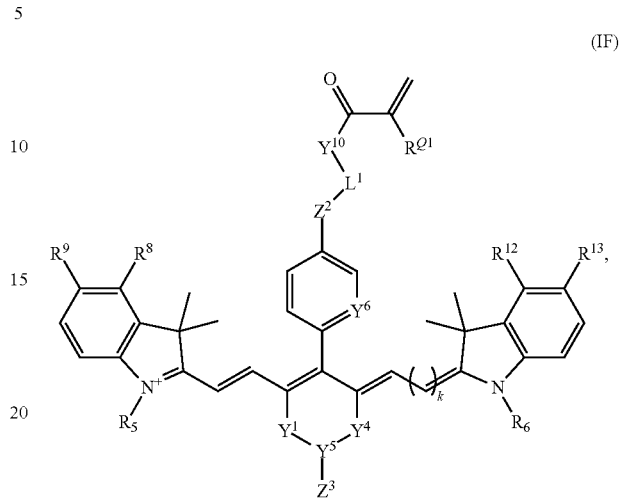

or a tautomer, salt, hydrate, or solvate thereof,
wherein:
  $Y^{10}$ is O, S, or $NR^{Z3}$,
  $Y^6$ is N or $CR^{16}$; and
  $R^{16}$ is H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, or hydroxy.

10. The polymerizable near-IR dye of claim 6, wherein the polymerizable near-IR dye has a structure according to formula (IG):

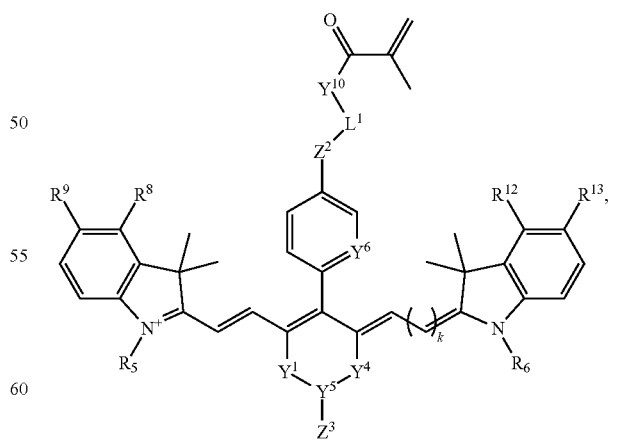

or a tautomer, salt, hydrate, or solvate thereof,
wherein:
  $Y^{10}$ is O, S, or $NR^{Z3}$,
  $Y^6$ is N or $CR^{16}$; and R[16] is H, SO$_3$H, B(OH)$_2$, optionally substituted amino, optionally substituted C$_1$-C$_{10}$ alkyl, optionally substituted C$_6$-C$_{10}$ aryl, optionally substituted ester, optionally substituted C$_1$-C$_{10}$ alkoxy, optionally substituted C$_6$-C$_{10}$ aryloxy, optionally substituted C$_6$-C$_{10}$ thioalkyl, optionally substituted C$_6$-C$_{10}$ thioaryl, optionally substituted C$_1$-C$_{10}$ heteroalkyl, optionally substituted C$_2$-C$_{10}$ heteroaryl, optionally substituted C$_2$-C$_{10}$ heteroalkoxy, optionally substituted C$_2$-C$_{10}$ heteroaryloxy, nitro, azido, carboxy, or hydroxy.

11. The polymerizable near-IR dye of claim 1, wherein the polymerizable near-IR dye is:

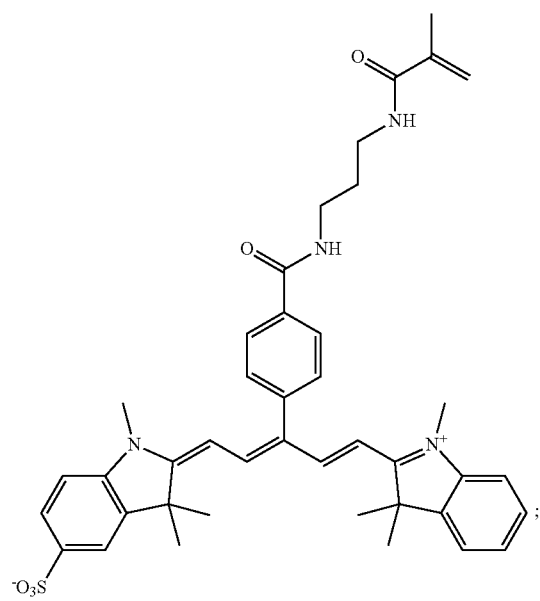

8

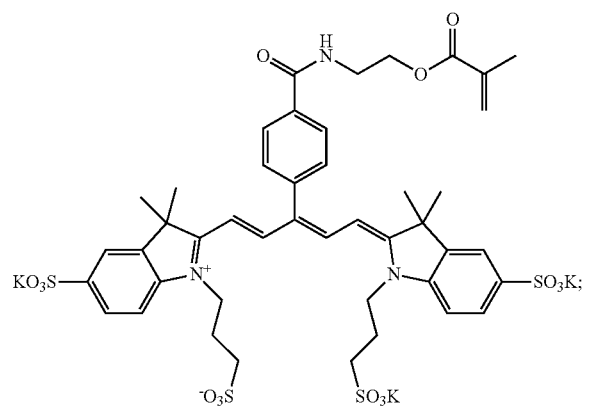

12

-continued

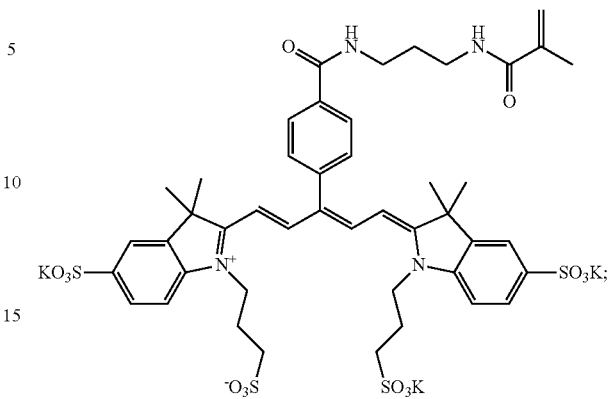

13

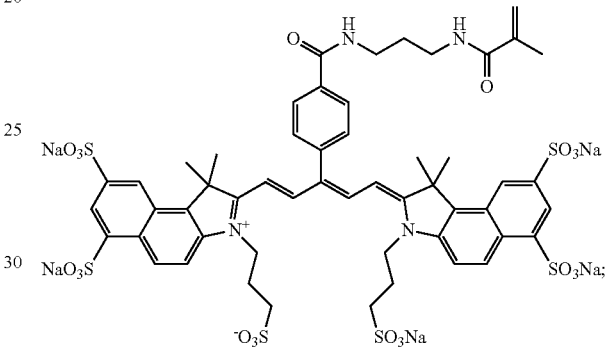

17

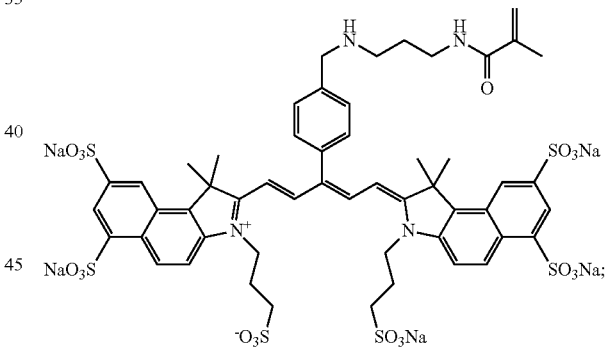

19

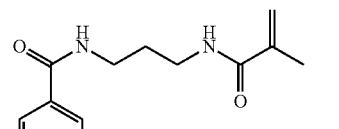

22

67
-continued
24
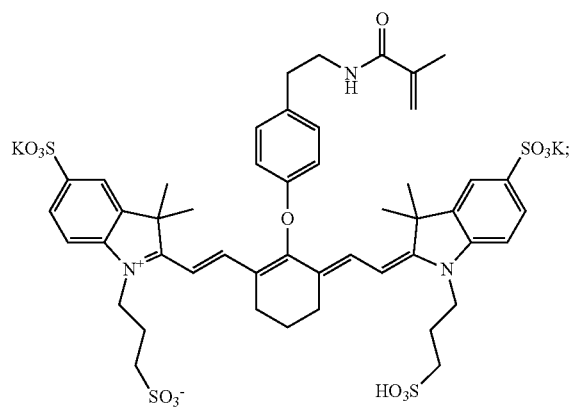
26
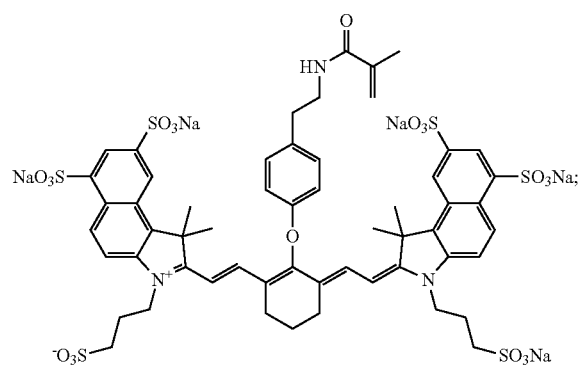
28
68
-continued
31
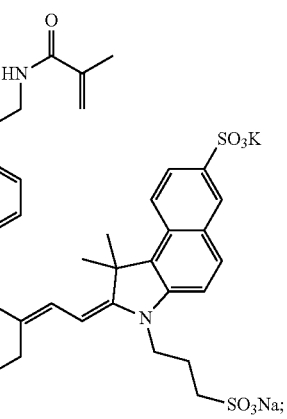
34
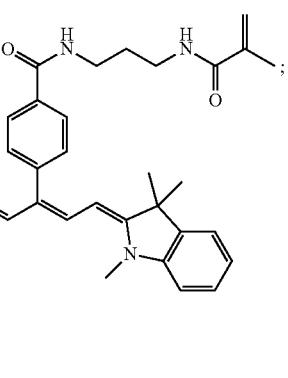
36
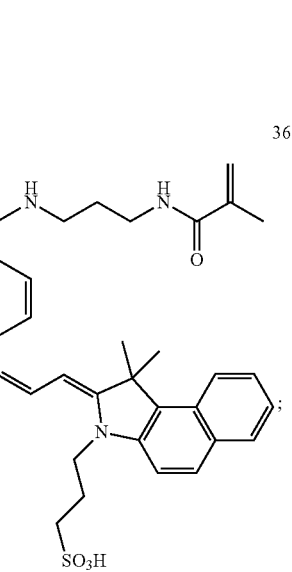

-continued

39

40

41

42

12. A polymer having a structure according to formula (II):

(II)

or a tautomer, salt, hydrate, or solvate thereof,
the polymer comprising a polymerizable near-IR dye and a monomer;
wherein:
$Z^1$ is absent, O, $NR^{Z1}$, or S;
$R^{Z1}$ is H, optionally substituted $C_1$-$C_{10}$ alkyl, or optionally substituted $C_2$-$C_{10}$ heteroalkyl;
$X^1$ is absent, optionally substituted $C_6$-$C_{10}$ arylene, or optionally substituted $C_1$-$C_{10}$ heteroarylene;
$Z^2$ is absent, $NR^{X1}$, O, S, $NR^{X2}C(O)$, OC(O), SC(O), C(O)O, $C(O)NR^{X3}$, C(S)O, or C(O)S;
$Z^3$ is absent or H;
$R^{X1}$, $R^{X2}$, and $R^{X3}$ are each independently H, optionally substituted $C_1$-$C_{10}$ alkyl, or optionally substituted $C_1$-$C_{10}$ heteroalkyl;
$L^1$ is absent, optionally substituted $C_1$-$C_{30}$ alkylene, or optionally substituted $C_1$-$C_{30}$ heteroalkylene;
$Q^1$ is $NR^{Z3}C(O)C(R^{Q1})CH_2$, $OC(O)C(R^{Q1})CH_2$, or $SC(O)C(R^{Q1})CH_2$;
$R^{Z3}$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;
$R^{Q1}$ is H, Me, Et, or n-Pr;
each of $Y^1$ and $Y^4$, independently, is absent or optionally substituted $C_1$-$C_4$ alkylene or optionally substituted $C_2$-$C_4$ heteroalkylene;

each of $Y^2$ and $Y^3$, independently, is absent or, together with the carbon atoms to which each is attached, form optionally substituted $C_6$-$C_{10}$ aryl or optionally substituted $C_2$-$C_{10}$ heteroaryl;

$Y^5$ is absent or N or $CR^7$;

$R^7$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;

each of $W^1$ and $W^2$, independently, is $NR^2$, S, O, Se, or $CR^3R^4$;

$R^2$, $R^3$, and $R^4$ are independently H, optionally substituted $C_1$-$C_{30}$ alkyl, optionally substituted $C_1$-$C_{30}$ heteroalkyl, or -$L^2$-$Q^2$;

$L^2$ is optionally substituted $C_1$-$C_{30}$ alkylene or optionally substituted $C_1$-$C_{30}$ heteroalkylene;

$Q^2$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$;

each of $R^5$ and $R^6$, independently, is -$L^3$-$Q^3$, optionally substituted $C_1$-$C_{30}$ alkyl, or optionally substituted $C_6$-$C_{10}$ aryl;

$L^3$ is optionally substituted $C_1$-$C_{30}$ alkylene or optionally substituted $C_1$-$C_{30}$ heteroalkylene;

$Q^3$ is H, $C(R^{Q1})CH_2$, $C_6H_4CHCH_2$, $NR^{Z3}C(O)C(R^{Q1})CH_2$, $OC(O)C(R^{Q1})CH_2$, or $SC(O)C(R^{Q1})CH_2$; and each k is independently 0 or 1;

wherein, the group $Q^1$ is linked to a group J, and

J is at least one monomer comprising HEMA (hydroxyethyl methacrylate), DMA (N,N-Dimethylacrylamide), HPA (Hydroxypropyl acrylate), methyl methacrylate, acrylamide, PEGMA (polyethyleneglycol methacrylate), methacrylic acid, hydroxyethyl acrylate, N-vinyl pyrrolidone, methacryloylaminopropyl trimethylammonium chloride, diallyl dimethyl ammonium chloride, vinyl benzyl trimethyl ammonium chloride, or sodium sulfopropyl methacrylate.

13. The polymer claim 12, wherein the polymer has a structure according to formula (IIA):

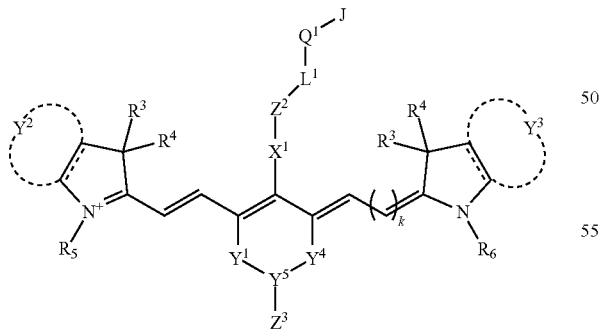

(IIA)

or a tautomer, salt, hydrate, or solvate thereof,
wherein
each $R^3$ is H, optionally substituted $C_1$-$C_{30}$ alkyl, or optionally substituted $C_1$-$C_{30}$ heteroalkyl; and each $R^4$ is H, optionally substituted $C_1$-$C_{30}$ alkyl, or optionally substituted $C_1$-$C_{30}$ heteroalkyl.

14. The polymer of claim 12, wherein the polymer has a structure according to formula (IIB):

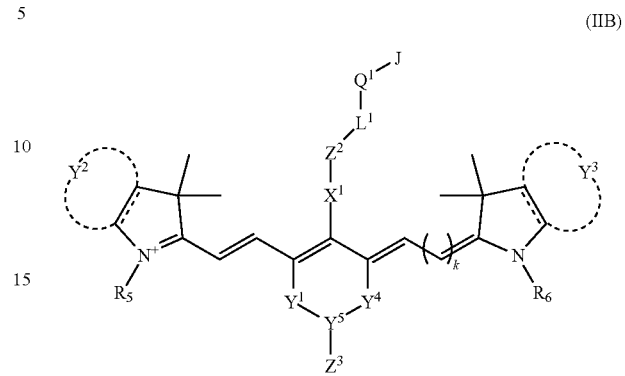

(IIB)

or a tautomer, salt, hydrate, or solvate thereof,
wherein $Y^2$, together with the carbon atoms to which it is attached, form optionally substituted $C_6$-$C_{10}$ arylene or optionally substituted $C_2$-$C_{10}$ heteroarylene; and $Y^3$, together with the carbon atoms to which it is attached, form optionally substituted $C_6$-$C_{10}$ arylene or optionally substituted $C_2$-$C_{10}$ heteroarylene.

15. The polymer of claim 12, wherein the polymerizable near-IR dye has a structure according to formula (IID):

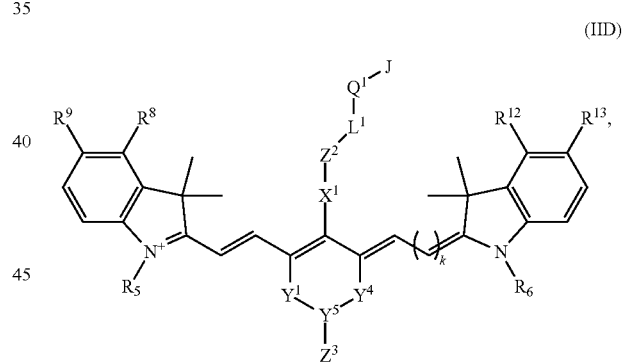

(IID)

or a tautomer, salt, hydrate, or solvate thereof,
wherein each of $R^1$, $R^9$, $R^{12}$, and $R^{13}$ is, independently, H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, hydroxy; or, $R^8$ and $R^9$ or $R^{12}$ and $R^{13}$ are, independently, together with the carbon atoms to which each is attached, form an optionally substituted phenyl ring.

16. The polymer of claim 15, wherein the polymer has a structure according to formula (IIE):

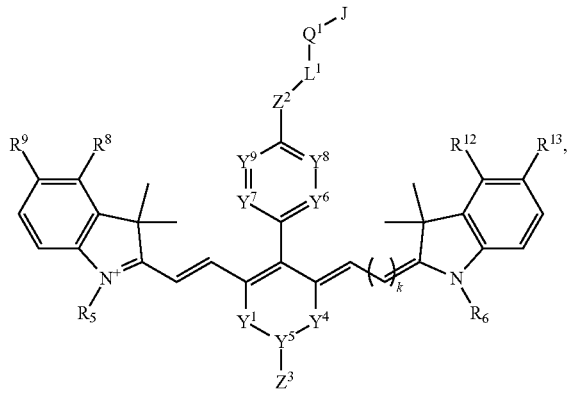

(IIE)

or a tautomer, salt, hydrate, or solvate thereof,
wherein:
  each of $Y^6$, $Y^7$, $Y^8$, and $Y^9$ is, independently, N or $CR^{16}$; and
  $R^{16}$ is H, $SO_3H$, $B(OH)_2$, optionally substituted amino, optionally substituted $C_1$-$C_{10}$ alkyl, optionally substituted $C_6$-$C_{10}$ aryl, optionally substituted ester, optionally substituted $C_1$-$C_{10}$ alkoxy, optionally substituted $C_6$-$C_{10}$ aryloxy, optionally substituted $C_6$-$C_{10}$ thioalkyl, optionally substituted $C_6$-$C_{10}$ thioaryl, optionally substituted $C_1$-$C_{10}$ heteroalkyl, optionally substituted $C_2$-$C_{10}$ heteroaryl, optionally substituted $C_2$-$C_{10}$ heteroalkoxy, optionally substituted $C_2$-$C_{10}$ heteroaryloxy, nitro, azido, carboxy, or hydroxy.

17. The polymer of claim 16, wherein the polymer has a structure according to formula (IIF):

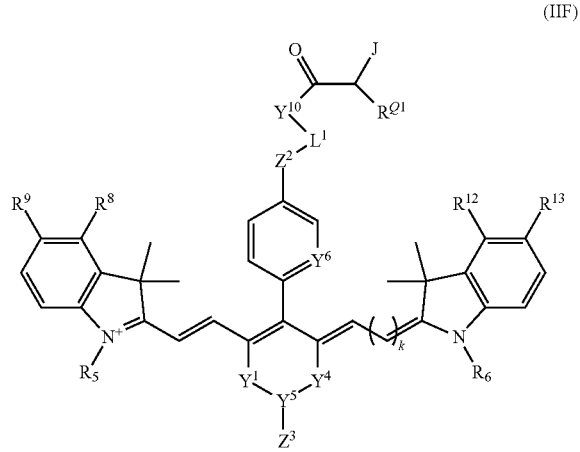

(IIF)

or a tautomer, salt, hydrate, or solvate thereof,
wherein:
  $Y^6$ is $CR^{16}$;
  $Y^{10}$ is O, S, or $NR^{Z3}$; and
  $R^{16}$ is H.

18. The polymer of claim 17, wherein $R^{Q1}$ is methyl.

19. A polymer comprising a polymerizable near-IR dye and a monomer, said polymer having a repeating unit according to formula (III):

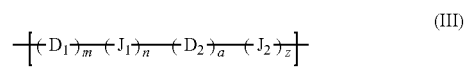

(III)

wherein:
  each $D_1$ and $D_2$ is independently a residue of a polymerizable near-IR dye, wherein said polymerizable near-IR dye has a structure according to formula (I):

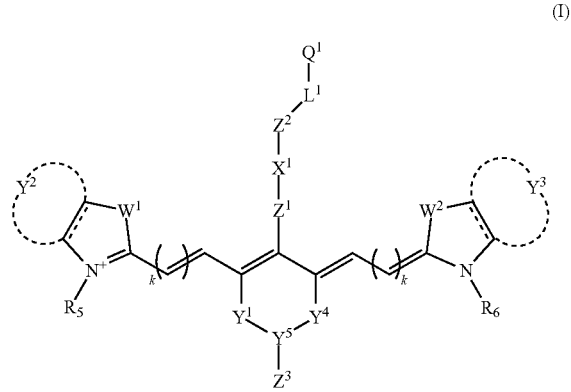

(I)

or a tautomer, salt, hydrate, or solvate thereof,
wherein:
  $Z^1$ is absent, O, $NR^{Z1}$, or S;
  $R^{Z1}$ is H, optionally substituted $C_1$-$C_{10}$ alkyl, or optionally substituted $C_2$-$C_{10}$ heteroalkyl;
  $X^1$ is absent, optionally substituted $C_6$-$C_{10}$ arylene, or optionally substituted $C_1$-$C_{10}$ heteroarylene;
  $Z^2$ is absent, $NR^{X1}$, O, S, $NR^{X2}C(O)$, $OC(O)$, $SC(O)$, $C(O)O$, $C(O)NR^{X3}$, $C(S)O$, or $C(O)S$;
  $Z^3$ is absent or H;
  $R^{X1}$, $R^{X2}$, and $R^{X3}$ are each independently H, optionally substituted $C_1$-$C_{10}$ alkyl, or optionally substituted $C_1$-$C_{10}$ heteroalkyl;
  $L^1$ is absent, optionally substituted $C_1$-$C_{30}$ alkylene, or optionally substituted $C_1$-$C_{30}$ heteroalkylene;
  $Q^1$ is $NR^{Z3}C(O)C(R^{Q1})CH_2$, $OC(O)C(R^{Q1})CH_2$, or $SC(O)C(R^{Q1})CH_2$;
  $R^{Z3}$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;
  $R^{Q1}$ is H, Me, Et, or n-Pr;
  each of $Y^1$ and $Y^4$, independently, is absent or optionally substituted $C_1$-$C_4$ alkylene or optionally substituted $C_2$-$C_4$ heteroalkylene;
  each of $Y^2$ and $Y^3$, independently, is absent or, together with the carbon atoms to which each is attached, form optionally substituted $C_6$-$C_{10}$ aryl or optionally substituted $C_2$-$C_{10}$ heteroaryl;
  $Y^5$ is absent or N or $CR^7$;
  $R^7$ is H, optionally substituted $C_1$-$C_{10}$ alkyl, optionally substituted $C_3$-$C_{10}$ cycloalkyl, optionally substituted $C_1$-$C_{10}$ heteroalkyl, or optionally substituted $C_1$-$C_{10}$ cycloheteroalkyl;
  each of $W^1$ and $W^2$, independently, is $NR^2$, S, O, Se, or $CR^3R^4$;

$R^2$, $R^3$, and $R^4$ are independently H, optionally substituted $C_1$-$C_{30}$ alkyl, optionally substituted $C_1$-$C_{30}$ heteroalkyl, or -$L^2$-$Q^2$;

$L^2$ is optionally substituted $C_1$-$C_{30}$ alkylene or optionally substituted $C_1$-$C_{30}$ heteroalkylene;

$Q^2$ is H, C($R^{Q1}$)$CH_2$, $C_6H_4$CHCH$_2$, NR$^{Z3}$C(O)C($R^{Q1}$)$CH_2$, OC(O)C($R^{Q1}$)$CH_2$, or SC(O)C($R^{Q1}$)$CH_2$;

each of $R^5$ and $R^6$, independently, is -$L^3$-$Q^3$, optionally substituted $C_1$-$C_{30}$ alkyl, or optionally substituted $C_6$-$C_{10}$ aryl;

$L^3$ is optionally substituted $C_1$-$C_{30}$ alkylene or optionally substituted $C_1$-$C_{30}$ heteroalkylene;

$Q^3$ is H, C($R^{Q1}$)$CH_2$, $C_6H_4$CHCH$_2$, NR$^{Z3}$C(O)C($R^{Q1}$)$CH_2$, OC(O)C($R^{Q1}$)$CH_2$, or SC(O)C($R^{Q1}$)$CH_2$; and each k is independently 0 or 1;

with the proviso that each $J_1$ and $J_2$ is a residue of HEMA (hydroxyethyl methacrylate), DMA (N,N-Dimethylacrylamide), HPA (Hydroxypropyl acrylate), methyl methacrylate, acrylamide, PEGMA (polyethyleneglycol methacrylate), methacrylic acid, hydroxyethyl acrylate, N-vinyl pyrrolidone, methacryloylaminopropyl trimethylammonium chloride, diallyl dimethyl ammonium chloride, vinyl benzyl trimethyl ammonium chloride, or sodium sulfopropyl methacrylate, wherein:

$D_1$ and $D_2$ can be the same or different;

$J_1$ and $J_2$ can be the same or different;

m is an integer from 1 to 100;

n is an integer from 0 to 100;

a is an integer from 0 to 100; and z is an integer from 0 to 100.

20. The polymer of claim 19 wherein the polymerizable near-IR dye is:

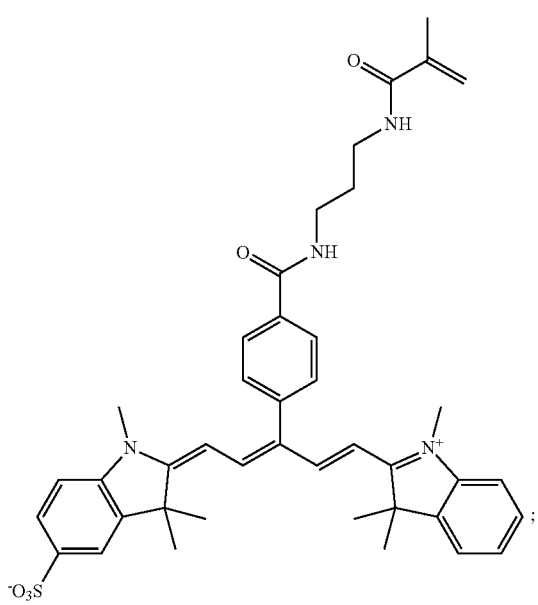

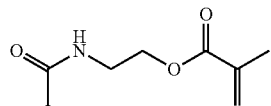

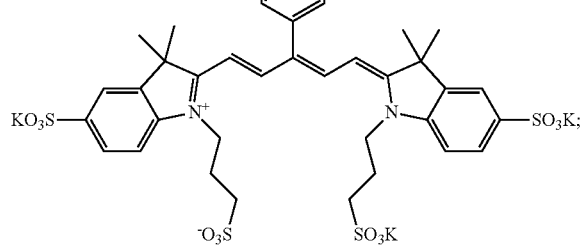

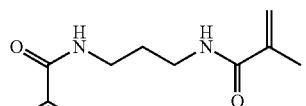

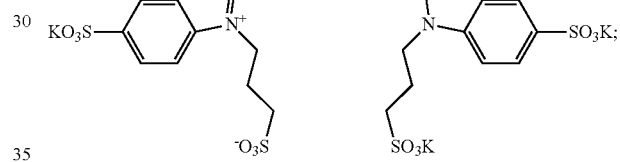

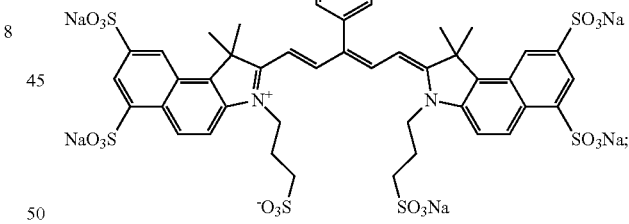

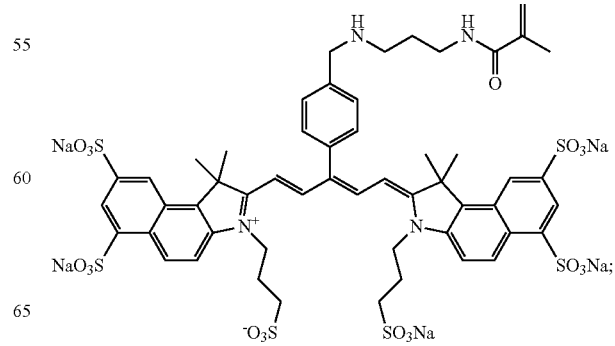

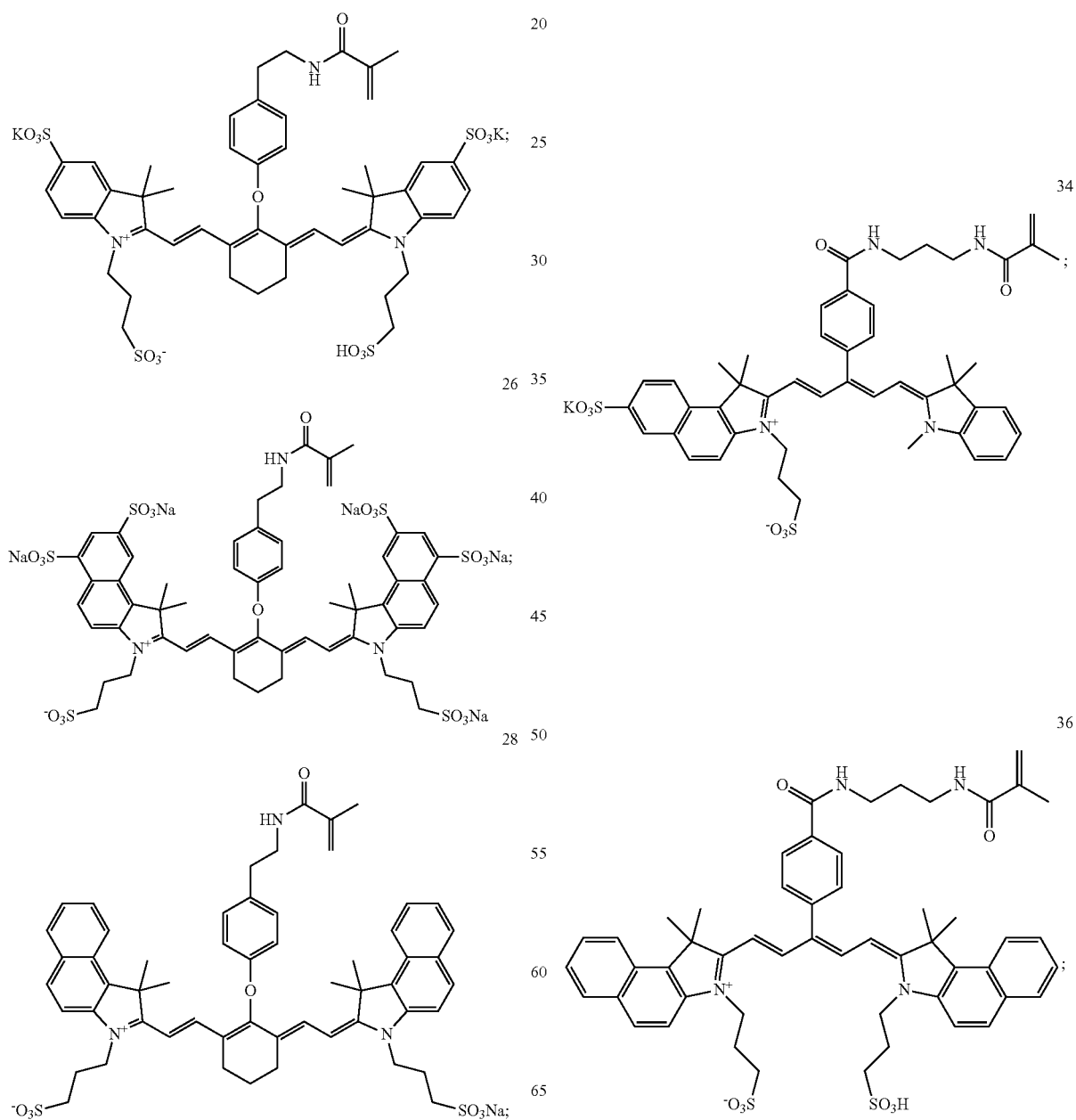

39
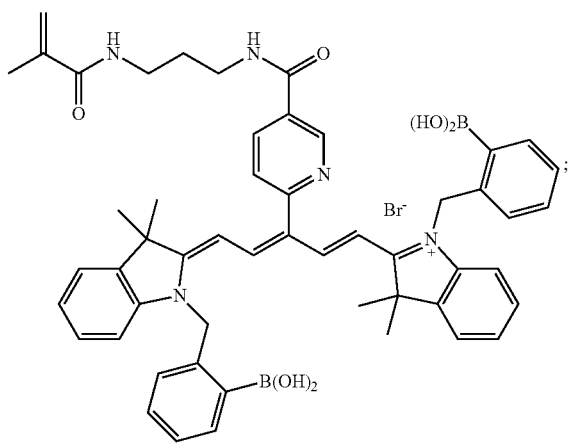
40
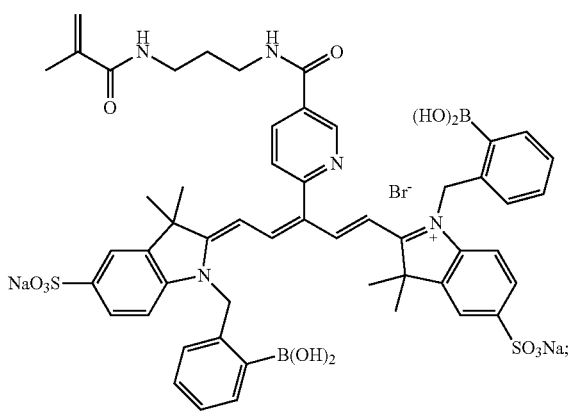
41
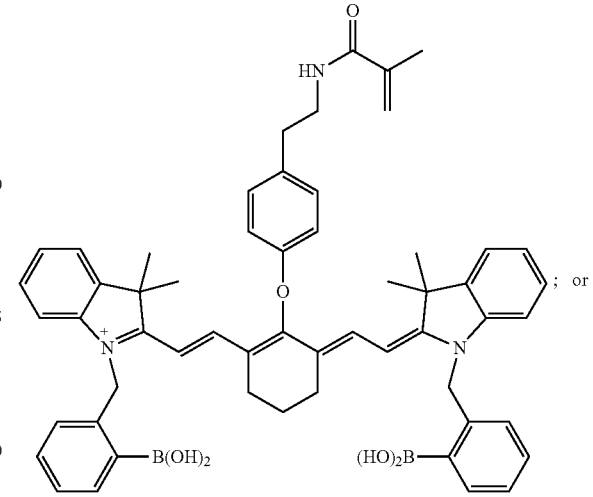
42
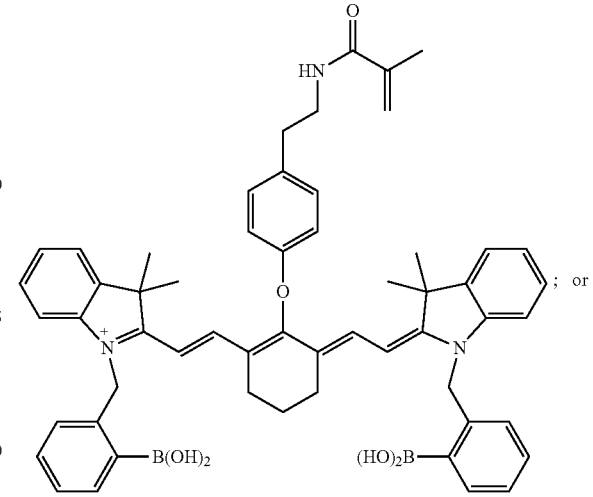
* * * * *